US011643689B2

(12) United States Patent
Dobak, III et al.

(10) Patent No.: US 11,643,689 B2
(45) Date of Patent: May 9, 2023

(54) METHODS FOR DIAGNOSING ATOPIC DERMATITIS USING GENE CLASSIFIERS

(71) Applicant: DermTech, Inc., La Jolla, CA (US)

(72) Inventors: John Daniel Dobak, III, La Jolla, CA (US); Burkhard Jansen, La Jolla, CA (US); Zuxu Yao, San Diego, CA (US)

(73) Assignee: DERMTECH, INC., La Jolla, CA (US)

( * ) Notice: Subject to any disclaimer, the term of this patent is extended or adjusted under 35 U.S.C. 154(b) by 0 days.

(21) Appl. No.: 17/214,675

(22) Filed: Mar. 26, 2021

(65) Prior Publication Data

US 2021/0222246 A1 Jul. 22, 2021

Related U.S. Application Data

(63) Continuation of application No. 16/874,473, filed on May 14, 2020, which is a continuation of application No. PCT/US2019/031203, filed on May 7, 2019.

(60) Provisional application No. 62/669,297, filed on May 9, 2018.

(51) Int. Cl.
C12Q 1/6883 (2018.01)
(52) U.S. Cl.
CPC ..... *C12Q 1/6883* (2013.01); *C12Q 2600/158* (2013.01)
(58) Field of Classification Search
None
See application file for complete search history.

(56) References Cited

U.S. PATENT DOCUMENTS

| | | | |
|---|---|---|---|
| 7,771,950 B2 | 8/2010 | Wohlgemuth et al. | |
| 10,852,307 B2 | 12/2020 | Leung et al. | |
| 2003/0228617 A1 | 12/2003 | Aune et al. | |
| 2007/0202540 A1 | 8/2007 | Benson | |
| 2009/0246768 A1 | 10/2009 | Sawalha et al. | |
| 2009/0263792 A1 | 10/2009 | Miyata et al. | |
| 2009/0298060 A1 | 12/2009 | Lal et al. | |
| 2010/0267033 A1 | 10/2010 | Abbas et al. | |
| 2011/0212099 A1 | 9/2011 | Liang et al. | |
| 2014/0065147 A1 | 3/2014 | Kastelein et al. | |
| 2017/0176455 A1 | 6/2017 | Leung et al. | |
| 2020/0308649 A1 | 10/2020 | Dobak et al. | |
| 2021/0198749 A1 | 7/2021 | Chang | |
| 2021/0222258 A1 | 7/2021 | Chang | |
| 2021/0246514 A1 | 8/2021 | Chang | |
| 2021/0324480 A1 | 10/2021 | Dobak et al. | |

FOREIGN PATENT DOCUMENTS

| | | | |
|---|---|---|---|
| WO | WO-0010579 A1 | 3/2000 | |
| WO | WO-03001985 A2 | 1/2003 | |
| WO | WO-2004047728 A2 | 6/2004 | |
| WO | WO-2005100603 A2 | 10/2005 | |
| WO | WO-2005108616 A1 | 11/2005 | |
| WO | WO-2007124072 A2 | 11/2007 | |
| WO | WO-2008137772 A1 | 11/2008 | |
| WO | WO-2009140550 A2 | 11/2009 | |
| WO | WO-2010025341 A2 | 3/2010 | |
| WO | WO-2013057241 A1 | 4/2013 | |
| WO | WO-2014176446 A1 | 10/2014 | |
| WO | WO-2014208645 A1 | 12/2014 | |
| WO | WO-2014210467 A1 | 12/2014 | |
| WO | WO-2016014705 A1 | 1/2016 | |
| WO | WO-2016179043 A1 | 11/2016 | |
| WO | WO-2017165199 A1 | 9/2017 | |
| WO | WO-2018191268 A1 | 10/2018 | |
| WO | WO-2019161126 A1 | 8/2019 | |
| WO | WO-2019183620 A1 | 9/2019 | |
| WO | WO-2019217478 A1 | 11/2019 | |
| WO | WO-2020008192 A2 | 1/2020 | |
| WO | WO-2020035707 A1 | 2/2020 | |
| WO | WO-2020198229 A1 | 10/2020 | |
| WO | WO-2020206085 A1 | 10/2020 | |

OTHER PUBLICATIONS

Sonokoly et al. J Allergy Clin Immunol. 2006. 117:411-417 (Year: 2006).*
Homey et al. J. Immunol. 2000. 164: 3465-3470 (Year: 2000).*
Seibold et al J Allergy Clin Immunol. Feb. 1, 2017. vol. 139. Issue 2, Supplement, Abstract 856, p. AB273 (Year: 2017).*
Dyjack et al J Allergy Clin Immunol. Jan. 6, 2018. 141: 1298-13-9 and Supplemental Table 4 (Year: 2018).*
Kim et al J Allergy Clin Immunol. Feb. 2015 vol. 135, Issue 2, Supplement AB261 (Year: 2015).*
Lund et al J Immunology. 2007. 178: 3648-3660 (Year: 2007).*
Pedicini et al PLoS Comput Biol. 2010. 6(12): e1001032, pp. 1-8 (Year: 2010).*
Thijs et al J Allergy Clin Immunol. Apr. 2017. 140: 730-737 (Year: 2017).*
Zhou et al J. Allergy Clin Immunol. Online Jan. 24, 2019, 144: 144-156 and Supplementary Material, total of 27 pages (Year: 2019).*
Ruzicka et al NEJM. 2017. 376)9):826-835) (Year: 2017).*
Affymetrix NetAffxTM Analysis Center (available via URL: https://www.affynnetrix.conn/analysis/netaffx/showresults.affx. printed on Oct. 21, 2020 (2020).
Chen et al. Type I interferon suppresses memory Th2 cell cytokine secretion from allergic subjects. Allergy 75(3):695-698 (2020).
Co-pending U.S. Appl. No. 17/214,695, inventors Dobak; John Daniel et al., filed Mar. 26, 2021.
Crow. Type I interferon in the pathogenesis of lupus. Immunol 192:5459-5468 (2014).
Itoh et al. Generation of 3D skin equivalents fully reconstituted from human induced pluripotent stem cells (iPSCs). PLoS One 8(10):e77673 (2013).

(Continued)

*Primary Examiner* — Carla J Myers
(74) *Attorney, Agent, or Firm* — Wilson Sonsini Goodrich & Rosati

(57) ABSTRACT

Disclosed herein are methods of detecting an altered gene expression levels in a subject suspected of having atopic dermatitis. Further described herein are methods of treating atopic dermatitis in a subject having an exhibiting an altered gene expression level.

16 Claims, 28 Drawing Sheets

(1 of 28 Drawing Sheet(s) Filed in Color)

(56) References Cited

OTHER PUBLICATIONS

Liu et al. Epidermal Genetic Information Retrieval is a non-invasive method of evaluating message (mRNA) profiles of lesional versus non-lesional skin of psoriatic subjects before and after initiations of therapy. J Investigative Dermatology. 122:A54 Abstract 323 (2004).
Liu et al. Inhibition of p38 MAPK signaling augments skin tumorigenesis via NOX2 driven ROS generation. PLoS One 9(5):e97245 (2014).
Merola et al. Non-invasive tape sampling reveals a type I interferon RNA signature in cutaneous lupus erythematosus that distinguishes affected from unaffected and healthy volunteer skin. J Investigative Dermatology 138(5): Abstract 1096 (2018).
Mok. The Jakinibs in systemic lupus erythematosus: progress and prospects. Expert Opin Investig Drugs. 28(1):85-92 (2019).
Neagu et al. miRNAs in the Diagnosis and Prognosis of Skin Cancer. Front Cell Dev Biol 8:71 (2020 ).
PCT/US2019/031203 International Invitation to Pay Additional Fees dated Jul. 11, 2019.
PCT/US2019/031203 International Search Report and Written Opinion dated Aug. 29, 2019.
Roberson et al., Psoriasis genetics: breaking the barrier. Trends in Genetics 26(9):415-423 (2010).
Schauberger et al. Development of a non-invasive method of RNA collection in children with atopic dermatitis. J Allergy Clin Immunol. 139(2):AB239, No. 751 (2017).
Shen et al., Epigenetic and genetic dissections of UV-induced global gene dysregulation in skin cells through multi-omics analyses. Scientific Reports 7:42646 (2017).
Shen et al., Transcriptome analysis identifies the dysregulation of ultraviolet target genes in human skin cancers. PLoS One 11(9):e0163054 [1-14] (2016).
Stevens et al. Disease-associated KIF3A variants alter gene methylation and expression impacting skin barrier and atopic dermatitis risk. Nature Communications 11:4092 (2020).
Torres et al. MicroRNA Ratios Distinguish Melanomas from Nevi. J Invest Dermatol. 140(1):164-173.e7 (2020).
U.S. Appl. No. 16/874,473 Office Action dated Oct. 26, 2020.
U.S. Appl. No. 16/874,473 Office Action dated Feb. 5, 2021.
Wong et al. Analysis of RNA recovery and gene expression in the epidermis using non-invasive tape stripping. J Dermatol Science 44:81-92 (2006).
Yao et al. An Adhesive Patch-Based Skin Biopsy Device for Non-invasive Gene Expression Analysis in Dermatology. DermTech, Mar. 2017, available via URL: dernntech.conn/wp-content/uploads/2017/03/Skin-Biopsy-Device-1.pdf (2017).
Zaba et al. Effective treatment of psoriasis with etanercept is linked to suppression of IL-17 signaling, not immediate response TNF genes. J Allergy Clin Immunol 124:1022 (2009).
Co-pending U.S. Appl. No. 17/315,199, inventors Dobak; John Daniel et al., filed May 7, 2021.
Co-pending U.S. Appl. No. 17/354,899, inventors Dobak; John Daniel et al., filed Jun. 22, 2021.
Co-pending U.S. Appl. No. 29/796,477, inventor Dobak; John, filed Jun. 24, 2021.
Dobbeling et al. Method for simultaneous RNA and DNA isolation from biopsy material, culture cells, plants and bacteria. Biotechniques 22:88-90 (1997).
Enderle et al. Monitoring therapy response and resistance mutations in circulating RNA and DNA of plasma from melanoma patients. Obtained from http://cpnr-cw7w.accessdomain.com/sites/default/files/2014_11_14_longitudinal_poster_final3_website.pdf on Aug. 23, 2021 (2014).
Hennig et al. Automated extraction of DNA and RNA from a single formalin-fixed paraffin-embedded tissue section for analysis of both single-nucleotide polymorphisms and mRNA expression. Clinical Chemistry 56:1845-1853 (2010).
Krueger et al. Non-invasive gene expression analysis for psoriasis. Available via URL: dermtech.com/wp-content/uploads/2017/03/Psoriasis.pdf (2017).
U.S. Appl. No. 16/874,473 Office Action dated Aug. 6, 2021.
U.S. Appl. No. 17/214,695 Office Action dated Jul. 27, 2021.
Wang et al. Simultaneous Extraction of DNA and RNA from Hepatocellular Carcinoma (Hep G2) Based on Silica-Coated Magnetic Nanoparticles. J. Nanosci. Nanotechnol. 17:802-806 (2017).
Bissonnette et al. Palmoplantar pustular psoriasis (PPPP) is characterized by activation of the IL-17A pathway. J Dermatol Science 85(1):20-26 (2016).
U.S. Appl. No. 16/874,473 Office Action dated Jan. 24, 2022.
Capone et al. Systems analysis of human T helper17 cell differentiation uncovers distinct time-regulated transcriptional modules. iScience. 24:102492 (2021).
Pan et al. Expression profiles of Th17 pathway related genes in human systemic lupus erythematosus. Mol Biol Rep. 40:391-399 (2013).
U.S. Appl. No. 17/214,695 Office Action dated Nov. 29, 2021.
Bogaczewicz et al. Medium-dose ultraviolet AI phototherapy and mRNA expression of TSLP, TARC, IL-5, and IL-13 in acute skin lesions in atopic dermatitis. Int'l J Derm 55(8):856-863 (2015).
Meng et al. New mechanism underlying IL-31-induced atopic dermatitis. J Allergy Clin Immunol 141(5):1677-1689 (2018).
Nobbe et al. IL-31 Expression by Inflammatory Cells is Preferentially Elevated in Atopic Dermatitis. Acta Derm Venereol 92(1):24-8 (2012).
U.S. Appl. No. 16/874,473 Office Action dated Jun. 7, 2022.
U.S. Appl. No. 17/214,695 Office Action dated Apr. 5, 2022.
U.S. Appl. No. 17/214,695 Office Action dated Sep. 23, 2022.
Yao et al. An adhesive patch-based skin biopsy device for molecular diagnostics and skin microbiome studies. J Drugs Dermatol 16:979-986 (2017).

* cited by examiner

Phase III Data 16 week endpoint

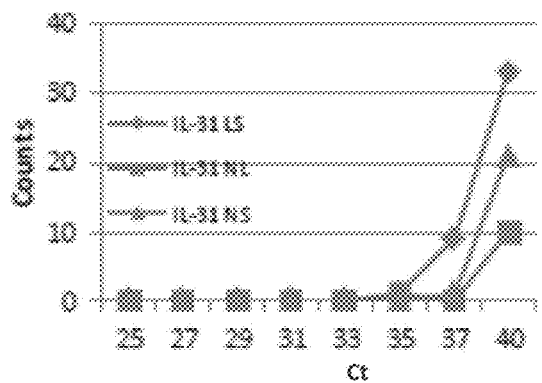
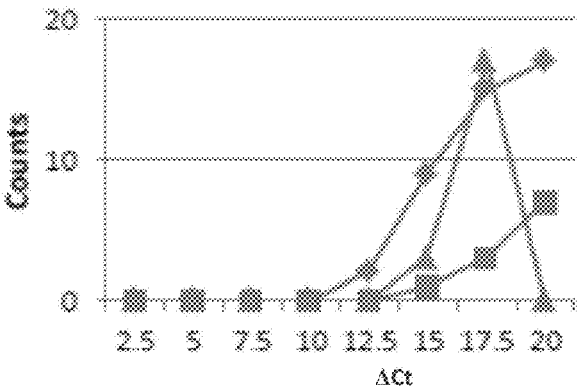
FIG. 16A
FIG. 16B
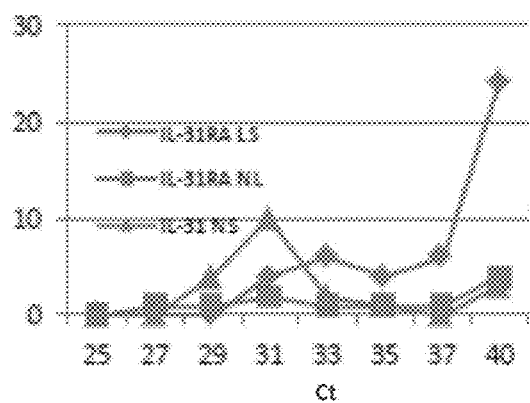
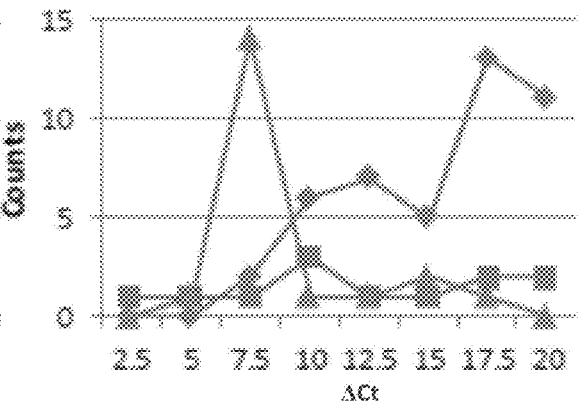
FIG. 17A
FIG. 17B
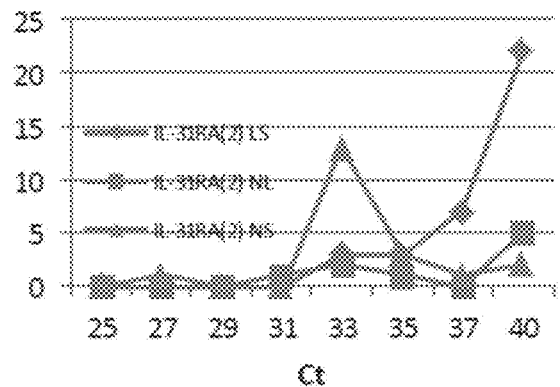
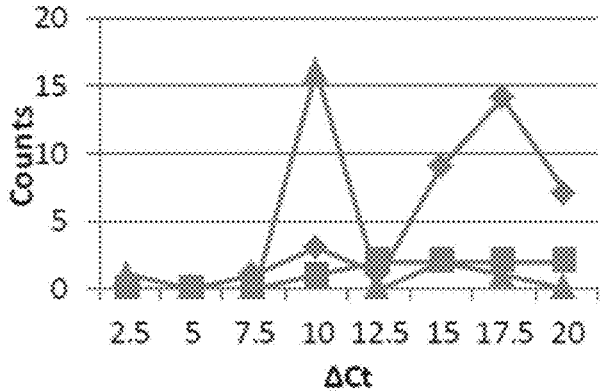
FIG. 18A
FIG. 18B

METHODS FOR DIAGNOSING ATOPIC DERMATITIS USING GENE CLASSIFIERS

CROSS-REFERENCE

This application a continuation of U.S. application Ser. No. 16/874,473 filed May 14, 2020, which is a continuation of International Application No. PCT/US19/31203 filed May 7, 2019 which claims the benefit of U.S. Provisional Application No. 62/669,297 filed May 9, 2018, each of which is incorporated herein by reference in its entirety.

BACKGROUND OF THE DISCLOSURE

Skin diseases are some of the most common human illnesses and represent an important global burden in healthcare. Three skin diseases are in the top ten most prevalent diseases worldwide, and eight fall into the top 50. When considered collectively, skin conditions range from being the second to the 11th leading causes of years lived with disability.

SUMMARY OF THE DISCLOSURE

Disclosed herein, in certain embodiments, is a method of detecting the presence of an autoimmune disease based on molecular risk factors. In some instances, described herein is a method of detecting the presence of psoriasis, lupus, or atopic dermatitis based on the molecular risk factors. In some instances, also described herein is a method of monitoring the progression of an autoimmune disease, e.g., psoriasis, lupus, or atopic dermatitis, based on the molecular risk factors.

Disclosed herein, in certain embodiments, is a method of detecting gene expression levels of at least two of IL-17A, IL-17F, IL-8, CXCL5, S100A9, and DEFB4A in a subject suspected of having psoriasis, comprising: (a) isolating nucleic acids from a skin sample obtained from the subject, where the skin sample comprises cells from the stratum corneum; and (b) detecting the expression levels of at least two of IL-17A, IL-17F, IL-8, CXCL5, S100A9, and DEFB4A by contacting the isolated nucleic acids with a set of probes that recognizes at least two of IL-17A, IL-17F, IL-8, CXCL5, S100A9, and DEFB4A, and detect binding between at least two of IL-17A, IL-17F, IL-8, CXCL5, S100A9, and DEFB4A and the set of probes.

Disclosed herein, in certain embodiments, is a method of detecting gene expression levels from a first gene classifier and a second gene classifier in a subject suspected of having psoriasis, comprising: (a) isolating nucleic acids from a skin sample obtained from the subject, wherein the skin sample comprises cells from the stratum corneum; (b) detecting the expression levels of one or more genes from the first gene classifier: IL-17A, IL-17F, IL-8, CXCL5, S100A9, and DEFB4A, by contacting the isolated nucleic acids with a set of probes that recognizes one or more genes from the first gene classifier, and detects binding between one or more genes from the first gene classifier and the set of probes; and (c) detecting the expression levels of one or more genes from the second gene classifier: IL-17C, S100A7, IL-17RA, IL-17RC, IL-23A, IL-22, IL-26, IL-24, IL-6, CXCL1, IFN-gamma, IL-31, IL-33, TNFα, LCN2, CCL20, and TNFRSF1A, by contacting the isolated nucleic acids with an additional set of probes that recognizes one or more genes from the second gene classifier, and detects binding between one or more genes from the second gene classifier and the additional set of probes.

Disclosed herein, in certain embodiments, is a method of treating a subject with an inhibitor of TNFα, IL-17A, or IL-23, wherein the subject has psoriasis, the method comprising the steps of: determining whether the subject has an altered gene expression level by: isolating nucleic acids from a skin sample comprising cells from the stratum corneum; and performing or having performed an expression analysis on the skin sample by contacting the isolated nucleic acids with a set of probes that recognizes at least two of IL-17A, IL-17F, IL-8, CXCL5, S100A9, and DEFB4A, and detect binding between at least two of IL-17A, IL-17F, IL-8, CXCL5, S100A9, and DEFB4A and the set of probes; and if the subject has an altered gene expression level of at least two of IL-17A, IL-17F, IL-8, CXCL5, S100A9, and DEFB4A, then administer to the subject an inhibitor of TNFα, IL-17A, or IL-23 or increase the level of the treatment with the inhibitor, and if the subject does not have an altered gene expression level of at least two of IL-17A, IL-17F, IL-8, CXCL5, S100A9, and DEFB4A, then does not administer the inhibitor or discontinue the treatment with the inhibitor.

Disclosed herein, in certain embodiments, is a method of detecting gene expression levels of at least two of IL-13, IL-31, and TSLP in a subject suspected of having atopic dermatitis, comprising: (a) isolating nucleic acids from a skin sample obtained from the subject, where the skin sample comprises cells from the stratum corneum; and (b) detecting the expression levels of at least two of IL-13, IL-31, and TSLP by contacting the isolated nucleic acids with a set of probes that recognizes at least two of IL-13, IL-31, and TSLP, and detect binding between at least two of IL-13, IL-31, and TSLP and the set of probes.

Disclosed herein, in certain embodiments, is a method of detecting gene expression levels from a first gene classifier and a second gene classifier in a subject suspected of having atopic dermatitis, comprising: (a) isolating nucleic acids from a skin sample obtained from the subject, wherein the skin sample comprises cells from the stratum corneum; (b) detecting the expression levels of one or more genes from the first gene classifier: IL-13, IL-31, and TSLP, by contacting the isolated nucleic acids with a set of probes that recognizes one or more genes from the first gene classifier, and detects binding between one or more genes from the first gene classifier and the set of probes; and (c) detecting the expression levels of one or more genes from the second gene classifier: IL-13R, IL-4R, IL-17, IL-22, CXCL9, CXCL10, CXCL11, S100A7, S100A8, S100A9, CCL17, CCL18, CCL19, CCL26, CCL27, and NOS2, by contacting the isolated nucleic acids with an additional set of probes that recognizes one or more genes from the second gene classifier, and detects binding between one or more genes from the second gene classifier and the additional set of probes.

Disclosed herein, in certain embodiments, is a method of treating a subject with an antibody that specifically binds to interleukin-13 (IL-13) or interleukin-13 receptor (IL-13R), wherein the subject has atopic dermatitis, the method comprising the steps of: determining whether the subject has an altered gene expression level by: obtaining or having obtained isolating nucleic acids from a skin sample comprising cells from the stratum corneum; and performing or having performed an expression analysis on the skin sample by contacting the isolated nucleic acids with a set of probes that recognizes at least two of IL-13, IL-31, and TSLP, and detect binding between at least two of IL-13, IL-31, and TSLP, and the set of probes; and if the subject has an altered gene expression level of at least two of IL-13, IL-31, and TSLP, then administer to the subject an antibody that specifically binds to IL-13 or IL-13R, and if the subject does not have an altered gene expression level of at least two of IL-13, IL-31, and TSLP, then do not administer the antibody that specifically binds to IL-13 or IL-13R.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

The patent or application file contains at least one drawing executed in color. Copies of this patent or patent application publication with color drawing(s) will be provided by the Office upon request and payment of the necessary fee.

FIG. 16A shows expression of IL-31 in lesion and non-lesion skins compared to healthy normal skin.

FIG. 16B normalized gene expression change of IL-31 in lesion and non-lesion skins compared to healthy normal skin.

FIG. 17A shows expression of IL-31RA(1) in lesion and non-lesion skins compared to healthy normal skin.

FIG. 17B shows normalized gene expression change of IL-31RA(1) in lesion and non-lesion skins compared to healthy normal skin.

FIG. 18A shows expression of IL-31RA(2) in lesion and non-lesion skins compared to healthy normal skin.

FIG. 18B shows normalized gene expression change of IL-31RA(2) in lesion and non-lesion skins compared to healthy normal skin.

DETAILED DESCRIPTION OF THE DISCLOSURE

Figure 1:
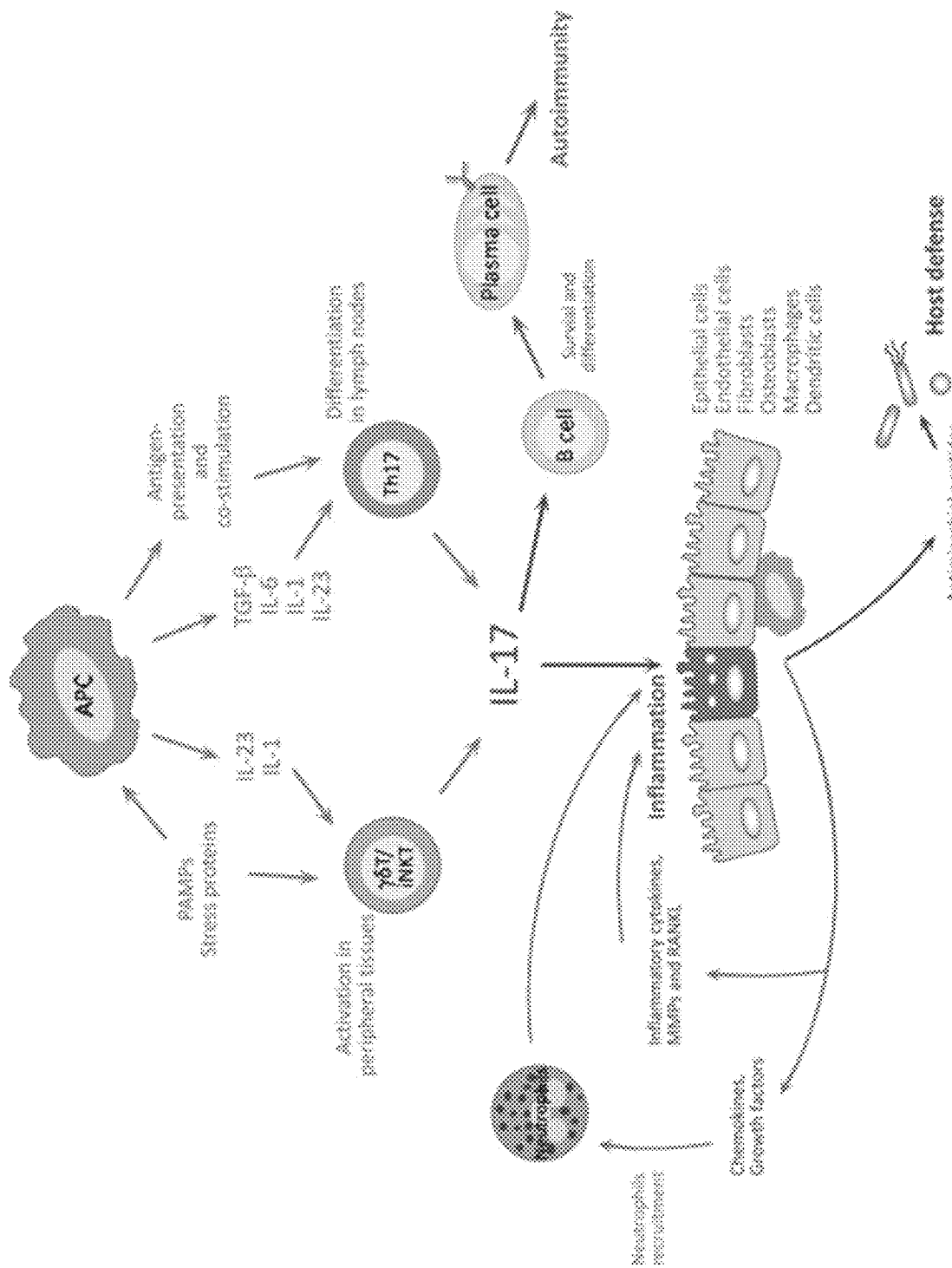
FIG. 1 shows the Th17 cytokine pathway
Figure 2:
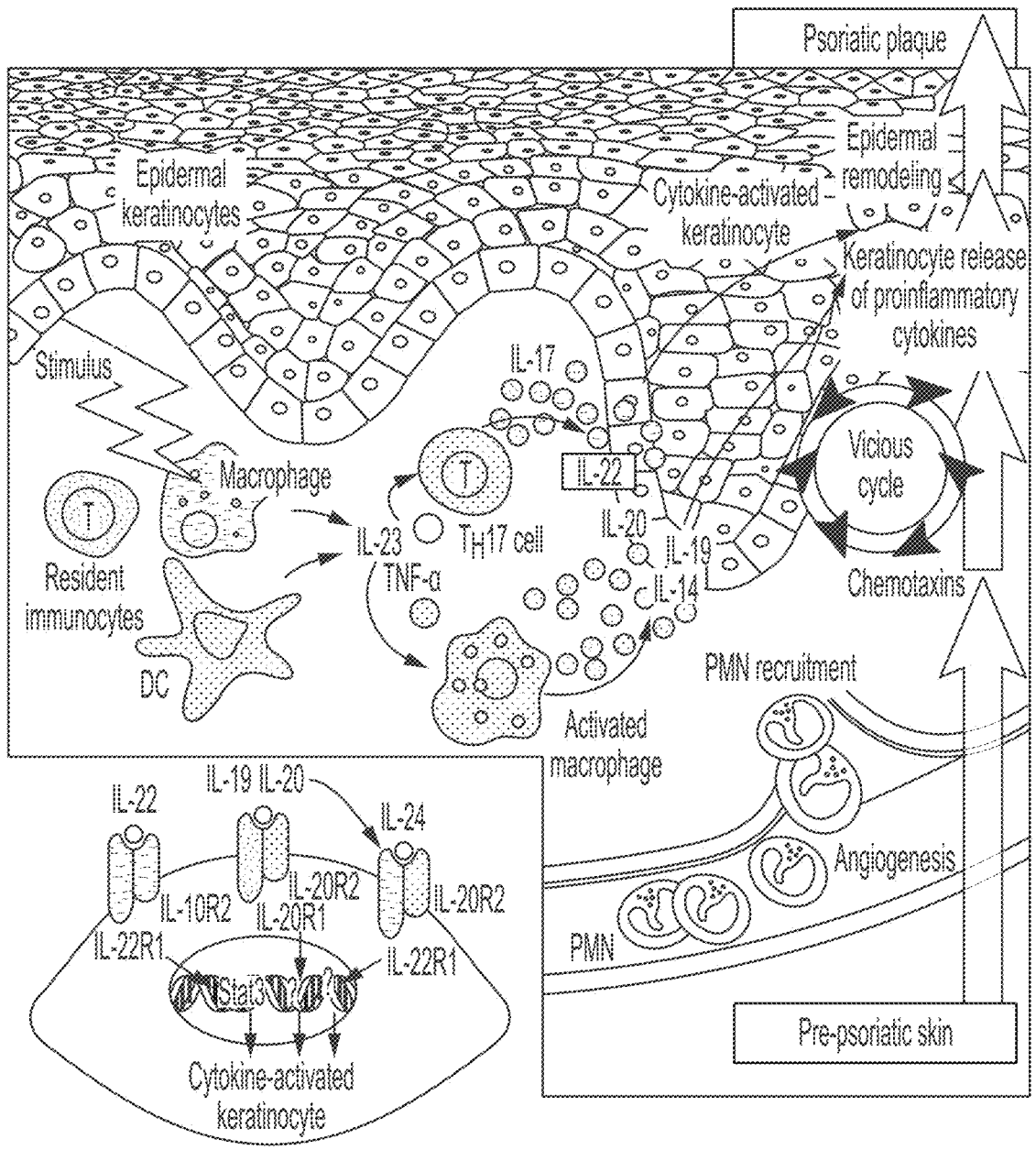
FIG. 2 shows the activation cycle in the skin from the IL-23/17 pathway, resulting in diseases such as psoriasis and atopic dermatitis.
Figure 3:
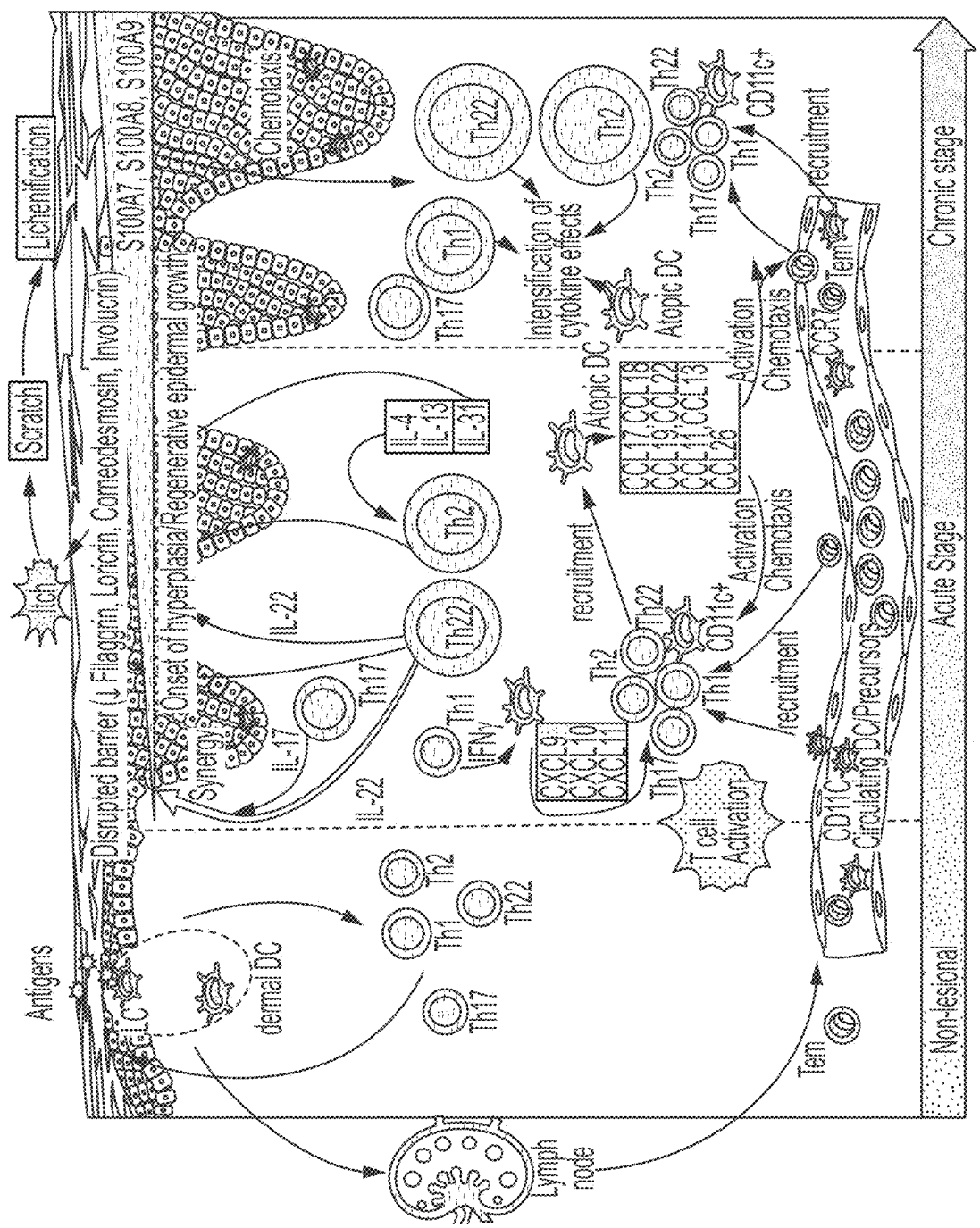
FIG. 3 shows the multiple inflammatory pathways elevated in chronic atopic dermatitis, including Th1, Th2, Th17, and Th22.
Figure 4:
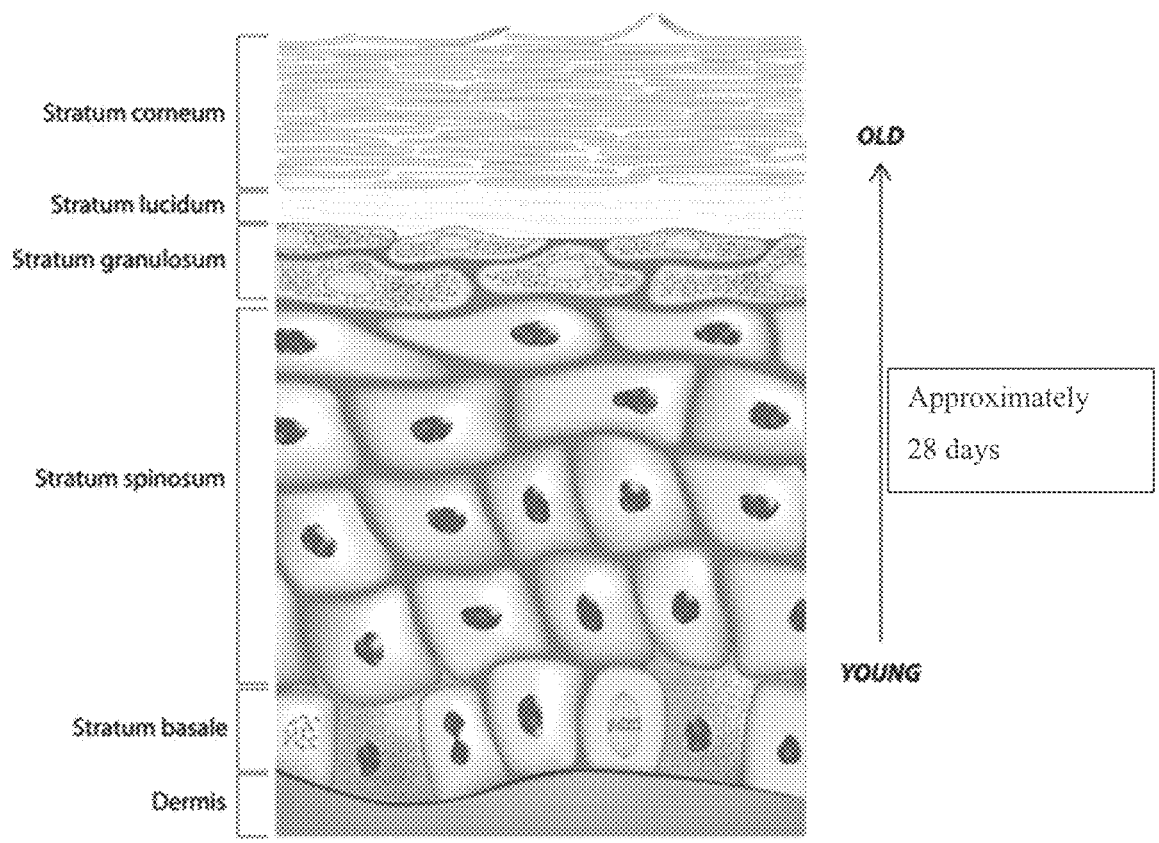
FIG. 4 shows the structure of the epidermis with the elapsed time for cells to progress from the dermal layer to the stratum corneum being approximately 28 days.

Autoimmune skin disorders occur when a person's own immune systems mistakenly attacks healthy cells. Exemplary skin disorders comprise, but are not limited to, psoriasis, lupus, and atopic dermatitis. Psoriasis is a persistent and chronic skin condition that can change the life cycle of skin cells. Psoriasis can cause cells to build up rapidly on the surface of the skin. The extra skin cells can form thick, silvery scales and itchy, dry, red patches that are sometimes painful.

Atopic dermatitis is a chronic disease that affects the skin. In atopic dermatitis, the skin becomes extremely itchy. Scratching leads to redness, swelling, cracking, "weeping" clear fluid, and finally, crusting and scaling. In most cases, there are periods of exacerbations followed by periods of remissions. Although it is difficult to identify exactly how many people are affected by atopic dermatitis, an estimated 20% of infants and young children experience symptoms of the disease. Approximately 60% of these infants continue to have one or more symptoms of atopic dermatitis in adulthood. Thus, more than 15 million people in the United States have symptoms of the disease. The "lesion area" is the region of the skin affected by atopic dermatitis. Generally a lesion is characterized by skin dryness (xerosis), redness, blisters, scabs, or any combination. A non-lesion area is not affected by atopic dermatitis or any other skin pathology.

Lupus, also known as lupus erythematosus, is an autoimmune disease, which affects multiple organs and systems in the body. An individual's own immune system attacks various cells causing a wide variety of signs and symptoms. With regards to the skin, there are lupus-specific skin lesions and non-specific skin lesions. In some instances, lupus comprises a spectrum of indications comprising cutaneous lupus erythematosus (CLE) on one end and systemic lupus erythematosus (SLE) (affecting other organs and systems) on the other end. In some cases, cutaneous lupus is categorized into three main entities: chronic cutaneous lupus (CCLE), subacute cutaneous lupus (SCLE) and acute cutaneous lupus (ACLE).

Systemic lupus erythematosus (SLE), is an autoimmune disease in which the body's immune system mistakenly attacks healthy tissue in many parts of the body. Symptoms vary between people and may be mild to severe. Common symptoms include painful and swollen joints, fever, chest pain, hair loss, mouth ulcers, swollen lymph nodes, feeling tired, and a red rash which is most commonly on the face. Often there are periods of illness, called flares, and periods of remission during which there are few symptoms.

In some embodiments, disclosed herein is a method of utilizing the expression level of genes in a gene classifier to determine the presence of an autoimmune skin disorder (e.g., psoriasis, atopic dermatitis, or lupus). In some instances, also described herein is a method of treating a subject determined to have an autoimmune skin disorder (e.g., psoriasis, atopic dermatitis, or lupus), based on the expression level of genes in a gene classifier.

Psoriasis Gene Classifiers and Methods of Use

In some embodiments, disclosed herein is a method of detecting the expression level of a gene from a gene classifier, which is associated with psoriasis. In some instances, the method comprises detecting the expression level of Interleukin 17A (IL-17A), Interleukin 17F (IL-17F), Interleukin 8 (IL-8), C-X-C Motif Chemokine Ligand 5 (CXCL5), S100 Calcium Binding Protein A9 (S100A9), Defensin Beta 4A (DEFB4A), or a combination thereof. In some instances, the method comprises (a) isolating nucleic acids from a skin sample obtained from the subject, wherein the skin sample (e.g., comprising cells from the stratum corneum); and (b) detecting the expression level of IL-17A, IL-17F, IL-8, CXCL5, S100A9, DEFB4A, or a combination thereof, by contacting the isolated nucleic acids with a set of probes that recognizes IL-17A, IL-17F, IL-8, CXCL5, S100A9, DEFB4A, or a combination thereof, and detects binding between IL-17A, IL-17F, IL-8, CXCL5, S100A9, DEFB4A, or a combination thereof and the set of probes.

In some embodiments, the method comprises detecting the expression levels of two or more, three or more, four or more, or five or more of genes from the gene classifier: IL-17A, IL-17F, IL-8, CXCL5, S100A9, and DEFB4A. In some cases, the method comprises detecting the expression levels of IL-17A, IL-17F, IL-8, CXCL5, S100A9, and DEFB4A. In some cases, the method comprises detecting the expression levels of IL-17A, IL-17F, IL-8, CXCL5, and S100A9. In some cases, the method comprises detecting the expression levels of IL-17A, IL-17F, IL-8, and CXCL5. In some cases, the method comprises detecting the expression levels of IL-17A, IL-17F, and IL-8. In some cases, the method comprises detecting the expression levels of IL-17A, and IL-17F.

In some instances, the expression level is an upregulated gene expression level. In some instances, the expression level is an upregulated gene expression level, compared to a gene expression level of an equivalent gene from a control sample. In some cases, the control sample is a normal skin sample. In some cases, the gene expression level of IL-17A, IL-17F, IL-8, CXCL5, S100A9, DEFB4A, or a combination thereof is upregulated. In some instances, the upregulated gene expression level occurs in areas of skin comprising psoriatic plaques.

In some instances, the gene expression level of IL-17A, IL-17F, IL-8, CXCL5, S100A9, or DEFB4A is increased by at least 1-fold, 2-fold, 3-fold, 4-fold, 5-fold, 10-fold, 20-fold, 30-fold, 40-fold, 50-fold, 60-fold, 70-fold, 80-fold, 90-fold, 100-fold, 110-fold, 120-fold, 130-fold, 150-fold, 200-fold, 300-fold, 500-fold, or more. In some cases, the gene expression level of IL-17A, IL-17F, IL-8, CXCL5, S100A9, or DEFB4A is increased by at least 10-fold. In some cases, the gene expression level of IL-17A, IL-17F, IL-8, CXCL5, S100A9, or DEFB4A is increased by at least 20-fold. In some cases, the gene expression level of IL-17A, IL-17F, IL-8, CXCL5, S100A9, or DEFB4A is increased by at least 30-fold. In some cases, the gene expression level of IL-17A, IL-17F, IL-8, CXCL5, S100A9, or DEFB4A is increased by at least 40-fold. In some cases, the gene expression level of IL-17A, IL-17F, IL-8, CXCL5, S100A9, or DEFB4A is increased by at least 50-fold. In some cases, the gene expression level of IL-17A, IL-17F, IL-8, CXCL5, S100A9, or DEFB4A is increased by at least 80-fold. In some cases, the gene expression level of IL-17A, IL-17F, IL-8, CXCL5, S100A9, or DEFB4A is increased by at least 100-fold. In some cases, the gene expression level of IL-17A, IL-17F, IL-8, CXCL5, S100A9, or DEFB4A is increased by at least 130-fold. In some cases, the gene expression level of IL-17A, IL-17F, IL-8, CXCL5, S100A9, or DEFB4A is increased by at least 150-fold. In some cases, the gene expression level of IL-17A, IL-17F, IL-8, CXCL5, S100A9, or DEFB4A is increased by at least 200-fold. In some cases, the gene expression level of IL-17A, IL-17F, IL-8, CXCL5, S100A9, or DEFB4A is increased by at least 300-fold. In some cases, the gene expression level of IL-17A, IL-17F, IL-8, CXCL5, S100A9, or DEFB4A is increased by at least 500-fold. In some cases, the increased gene expression level is compared to a gene expression level of an equivalent gene from a control sample. In some cases, the control sample is a normal skin sample. In some instances, the up-regulated gene expression level occurs in areas of skin comprising psoriatic plaques.

In some cases, the gene expression level of IL-17A, IL-17F, IL-8, CXCL5, S100A9, or DEFB is increased by at least 10%, 20%, 30%, 40%, 50%, 60%, 70%, 80%, 90%, 100%, 200%, 300%, 400%, 500%, or more. In some cases, the gene expression level of IL-17A, IL-17F, IL-8, CXCL5, S100A9, or DEFB is increased by at least 10%. In some cases, the gene expression level of IL-17A, IL-17F, IL-8, CXCL5, S100A9, or DEFB is increased by at least 20%. In some cases, the gene expression level of IL-17A, IL-17F, IL-8, CXCL5, S100A9, or DEFB is increased by at least 30%. In some cases, the gene expression level of IL-17A, IL-17F, IL-8, CXCL5, S100A9, or DEFB is increased by at least 40%. In some cases, the gene expression level of IL-17A, IL-17F, IL-8, CXCL5, S100A9, or DEFB is increased by at least 50%. In some cases, the gene expression level of IL-17A, IL-17F, IL-8, CXCL5, S100A9, or DEFB is increased by at least 80%. In some cases, the gene expression level of IL-17A, IL-17F, IL-8, CXCL5, S100A9, or DEFB is increased by at least 90%. In some cases, the gene expression level of IL-17A, IL-17F, IL-8, CXCL5, S100A9, or DEFB is increased by at least 100%. In some cases, the gene expression level of IL-17A, IL-17F, IL-8, CXCL5, S100A9, or DEFB is increased by at least 150%. In some cases, the gene expression level of IL-17A, IL-17F, IL-8, CXCL5, S100A9, or DEFB is increased by at least 200%. In some cases, the gene expression level of IL-17A, IL-17F, IL-8, CXCL5, S100A9, or DEFB is increased by at least 300%. In some cases, the gene expression level of IL-17A, IL-17F, IL-8, CXCL5, S100A9, or DEFB is increased by at least 500%. In some cases, the increased gene expression level is compared to a gene expression level of an equivalent gene from a control sample. In some cases, the control sample is a normal skin sample. In some instances, the down-regulated gene expression level occurs in areas of skin comprising psoriatic plaques.

In some embodiments, the set of probes recognizes at least one but no more than six genes selected from IL-17A, IL-17F, IL-8, CXCL5, S100A9, and DEFB. In some cases, the set of probes recognizes IL-17A and IL-17F. In some cases, the set of probes recognizes IL-8, CXCL5, S100A9, and DEFB4A. In some cases, the set of probes recognizes IL-17A, IL-8, and DEFB4A. In some cases, the set of probes recognizes IL-17F, CXCL5, and S100A9. In some cases, the set of probes recognizes IL-17A, IL-17F, IL-8, CXCL5, S100A9, and DEFB.

In some embodiments, the method further comprises detecting the expression levels of Interleukin 17C (IL-17C), S100 Calcium Binding Protein A7 (S100A7), Interleukin 17 Receptor A (IL-17RA), Interleukin 17 Receptor C (IL-17RC), Interleukin 23 Subunit Alpha (IL-23A), Interleukin 22 (IL-22), Interleukin 26 (IL-26), Interleukin 24 (IL-24), Interleukin 6 (IL-6), C-X-C Motif Chemokine Ligand 1 (CXCL1), Interferon Gamma (IFN-gamma), Interleukin 31, (IL-31), Interleukin 33 (IL-33), Tumor Necrosis Factor (TNFα), Lipocalin 2 (LCN2), C-C Motif Chemokine Ligand 20 (CCL20), TNF Receptor Superfamily Member 1A (TNFRSF1A) or a combination thereof. In some cases, the detecting comprises contacting the isolated nucleic acids with an additional set of probes that recognizes IL-17C, S100A7, IL-17RA, IL-17RC, IL-23A, IL-22, IL-26, IL-24, IL-6, CXCL1, IFN-gamma, IL-31, IL-33, TNFα, LCN2, CCL20, TNFRSF1A, or a combination thereof, and detects binding between IL-17C, S100A7, IL-17RA, IL-17RC, IL-23A, IL-22, IL-26, IL-24, IL-6, CXCL1, IFN-gamma, IL-31, IL-33, TNFα, LCN2, CCL20, TNFRSF1A, or a combination thereof and the additional set of probes.

In some cases, the additional set of probes recognizes one but no more than ten genes. In some cases, the additional set of probes recognizes 2, 3, 4, 5, 6, 7, 8, 9, 10, 11, 12, 13, 14, 15, 16 or 17 genes selected from IL-17C, S100A7, IL-17RA, IL-17RC, IL-23A, IL-22, IL-26, IL-24, IL-6, CXCL1, IFN-gamma, IL-31, IL-33, TNFα, LCN2, CCL20, and TNFRSF1A.

In some cases, the expression level of one or more genes selected from IL-17C, S100A7, IL-17RA, IL-17RC, IL-23A, IL-22, IL-26, IL-24, IL-6, CXCL1, IFN-gamma, IL-31, IL-33, TNFα, LCN2, CCL20, and TNFRSF1A is an elevated gene expression level. In such cases, the gene expression level is elevated by at least 1-fold, 2-fold, 3-fold, 4-fold, 5-fold, 10-fold, 20-fold, 30-fold, 40-fold, 50-fold, 60-fold, 70-fold, 80-fold, 90-fold, 100-fold, 110-fold, 120-fold, 130-fold, 150-fold, 200-fold, 300-fold, 500-fold, or more. In some instances, the gene expression level is elevated by at least 10%, 20%, 30%, 40%, 50%, 60%, 70%, 80%, 90%, 100%, 200%, 300%, 400%, 500%, or more. In some instances, the expression level is compared to a gene expression level of an equivalent gene from a control sample. In some instances, the control sample is a normal skin sample.

In some embodiments, a method described herein further comprises detecting a skin region affected with psoriasis. In some cases, also described herein include a method monitoring the skin region affected with psoriasis, for about 1 week, 2 weeks, 3 weeks, 1 month, 2 months, 6 months, or more.

In some instances, the method has an improved specificity, of at least or about 70%, 75%, 80%, 85%, 90%, or more than 95% when detecting the gene expression level of IL-17A, IL-17F, IL-8, CXCL5, S100A9, DEFB, or a combination thereof. In some embodiments, the specificity is at least or about 70%, 75%, 80%, 85%, 90%, or more than 95% when detecting the gene expression level of IL-17C, S100A7, IL-17RA, IL-17RC, IL-23A, IL-22, IL-26, IL-24, IL-6, CXCL1, IFN-gamma, IL-31, IL-33, TNFα, LCN2, CCL20, TNFRSF1A, or a combination thereof.

In some cases, the method also has an improved sensitivity. In some embodiments, the sensitivity is at least or about 70%, 75%, 80%, 85%, 90%, or more than 95% when detecting the gene expression levels of IL-17A, IL-17F, IL-8, CXCL5, S100A9, DEFB, or a combination thereof. In some cases, the sensitivity is at least or about 70%, 75%, 80%, 85%, 90%, or more than 95% when detecting the gene expression levels of IL-17C, S100A7, IL-17RA, IL-17RC, IL-23A, IL-22, IL-26, IL-24, IL-6, CXCL1, IFN-gamma, IL-31, IL-33, TNFα, LCN2, CCL20, TNFRSF1A, or a combination thereof.

In some embodiments, a method described herein comprises detecting gene expression levels from a first gene classifier and a second gene classifier in a subject in need thereof, comprising: (a) isolating nucleic acids from a skin sample obtained from the subject, wherein the skin sample (e.g., comprising cells from the stratum corneum); (b) detecting the expression levels of one or more genes from the first gene classifier: IL-17A, IL-17F, IL-8, CXCL5, S100A9, and DEFB, by contacting the isolated nucleic acids with a set of probes that recognizes one or more genes from the first gene classifier, and detects binding between one or more genes from the first gene classifier and the set of probes; and (c) detecting the expression levels of one or more genes from the second gene classifier: IL-17C, S100A7, IL-17RA, IL-17RC, IL-23A, IL-22, IL-6, IL-24, IL-6, CXCL1, IFN-gamma, IL-31, IL-33, TNFα, LCN2, CCL20, and TNFRSF1A, by contacting the isolated nucleic acids with an additional set of probes that recognizes one or more genes from the second gene classifier, and detects binding between one or more genes from the second gene classifier and the additional set of probes.

In some embodiments, also provided herein is a method of treating psoriasis, which comprises administering one or more inhibitors. Inhibitors for inclusion in methods for treatment of psoriasis described herein include, but are not limited to, inhibitors of TNFα, IL-17A, and IL-23. Exemplary inhibitors of TNFα include, but are not limited to, adalimumab, certolizumab, etanercept, golimumab, and infliximab. Exemplary inhibitors of IL-17A include, but are not limited to, ixekizumab (LY2439821), brodalumab (AMG 827), and secukinumab. Exemplary inhibitors of IL-23 include, but are not limited to, guselkumab, tildrakizumab, and risankizumab.

In some cases, the inhibitor for inclusion in the methods described herein for treatment of psoriasis is an inhibitor of TNFα. In some cases, the subject is treated with an inhibitor of TNFα such as adalimumab, certolizumab, etanercept, golimumab, or infliximab.

In some cases, the inhibitor for inclusion in the methods described herein for treatment of psoriasis is an inhibitor of IL-17A. In some cases, the subject is treated with an inhibitor of IL-17A such as ixekizumab (LY2439821), brodalumab (AMG 827), or secukinumab.

In some cases, the inhibitor for inclusion in the methods described herein for treatment of psoriasis is an inhibitor of IL-23. In some cases, the subject is treated with an inhibitor of IL-23 such as guselkumab, tildrakizumab, or risankizumab.

Atopic Dermatitis Gene Classifiers and Methods of Use

In some embodiments, disclosed herein is a method of detecting the expression level of a gene from a gene classifier, which is associated with atopic dermatitis. In some instances, the method comprises detecting the expression level of Interleukin 13 (IL-13), Interleukin 31 (IL-31), Thymic Stromal Lymphopoietin (TSLP), or a combination thereof. In some instances, the method comprises (a) isolating nucleic acids from a skin sample obtained from the subject, wherein the skin sample (e.g., comprising cells from the stratum corneum); and (b) detecting the expression level of IL-13, IL-31, TSLP, or a combination thereof, by contacting the isolated nucleic acids with a set of probes that recognizes IL-13, IL-31, TSLP, or a combination thereof, and detects binding between IL-13, IL-31, TSLP, or a combination thereof and the set of probes.

In some embodiments, the method comprises detecting the expression levels of two or more, or three or more of genes from the gene classifier: IL-13, IL-31, and TSLP. In some cases, the method comprises detecting the expression levels of IL-13, IL-31, and TSLP. In some cases, the method comprises detecting the expression levels of IL-31 and TSLP. In some cases, the method comprises detecting the expression levels of IL-13 and IL-31. In some cases, the method comprises detecting the expression levels of IL-13 and TSLP.

In some instances, the expression level is an upregulated gene expression level. In some instances, the expression level is an up-regulated gene expression level, compared to a gene expression level of an equivalent gene from a control sample. In some cases, the control sample is a normal skin sample. In some cases, the gene expression level of IL-13, IL-31, TSLP, or a combination thereof is up-regulated. In some instances, the up-regulated gene expression level occurs in areas of skin comprising atopic dermatitis.

In some instances, the gene expression level of IL-13, IL-31, or TSLP is increased by at least 1-fold, 2-fold, 3-fold, 4-fold, 5-fold, 10-fold, 20-fold, 30-fold, 40-fold, 50-fold, 60-fold, 70-fold, 80-fold, 90-fold, 100-fold, 110-fold, 120-fold, 130-fold, 150-fold, 200-fold, 300-fold, 500-fold, or more. In some cases, the gene expression level of IL-13, IL-31, or TSLP is increased by at least 10-fold. In some cases, the gene expression level of IL-13, IL-31, or TSLP is increased by at least 20-fold. In some cases, the gene expression level of IL-13, IL-31, or TSLP is increased by at least 30-fold. In some cases, the gene expression level of IL-13, IL-31, or TSLP is increased by at least 40-fold. In some cases, the gene expression level of IL-13, IL-31, or TSLP is increased by at least 50-fold. In some cases, the gene expression level of IL-13, IL-31, or TSLP is increased by at least 80-fold. In some cases, the gene expression level of IL-13, IL-31, or TSLP is increased by at least 100-fold. In some cases, the gene expression level of IL-13, IL-31, or TSLP is increased by at least 130-fold. In some cases, the gene expression level of IL-13, IL-31, or TSLP is increased by at least 150-fold. In some cases, the gene expression level of IL-13, IL-31, or TSLP is increased by at least 200-fold. In some cases, the gene expression level of IL-13, IL-31, or TSLP is increased by at least 300-fold. In some cases, the gene expression level of IL-13, IL-31, or TSLP is increased by at least 500-fold. In some cases, the decreased gene expression level is compared to a gene expression level of an equivalent gene from a control sample. In some cases, the control sample is a normal skin sample. In some instances, the down-regulated gene expression level occurs in areas of skin comprising atopic dermatitis.

In some cases, the gene expression level of IL-13, IL-31, or TSLP is increased by at least 10%, 20%, 30%, 40%, 50%, 60%, 70%, 80%, 90%, 100%, 200%, 300%, 400%, 500%, or more. In some cases, the gene expression level of IL-13, IL-31, or TSLP is increased by at least 10%. In some cases, the gene expression level of IL-13, IL-31, or TSLP is increased by at least 20%. In some cases, the gene expression level of IL-13, IL-31, or TSLP is increased by at least 30%. In some cases, the gene expression level of IL-13, IL-31, or TSLP is increased by at least 40%. In some cases, the gene expression level of IL-13, IL-31, or TSLP is increased by at least 50%. In some cases, the gene expression level of IL-13, IL-31, or TSLP is increased by at least 80%. In some cases, the gene expression level of IL-13, IL-31, or TSLP is increased by at least 90%. In some cases, the gene expression level of IL-13, IL-31, or TSLP is increased by at least 100%. In some cases, the gene expression level of IL-13, IL-31, or TSLP is increased by at least 150%. In some cases, the gene expression level of IL-13, IL-31, or TSLP is increased by at least 200%. In some cases, the gene expression level of IL-13, IL-31, or TSLP is increased by at least 300%. In some cases, the gene expression level of IL-13, IL-31, or TSLP is increased by at least 500%. In some cases, the decreased gene expression level is compared to a gene expression level of an equivalent gene from a control sample. In some cases, the control sample is a normal skin sample. In some instances, the down-regulated gene expression level occurs in areas of skin comprising atopic dermatitis.

In some embodiments, the set of probes recognizes at least one but no more than three genes selected from IL-13, IL-31, and TSLP. In some cases, the set of probes recognizes IL-13 and IL-31. In some cases, the set of probes recognizes IL-31 and TSLP. In some cases, the set of probes recognizes IL-13 and TSLP. In some cases, the set of probes recognizes IL-13, IL-31, and TSLP.

In some embodiments, the method further comprises detecting the expression levels of Interleukin 13 Receptor (IL-13R), Interleukin 4 Receptor (IL-4R), Interleukin 17 (IL-17), Interleukin 22 (IL-22), C-X-C Motif Chemokine Ligand 9 (CXCL9), C-X-C Motif Chemokine Ligand 10 (CXCL10), C-X-C Motif Chemokine Ligand 10 (CXCL11), S100 Calcium Binding Protein A7 (S100A7), S100 Calcium Binding Protein A8 (S100A8), S100 Calcium Binding Protein A9 (S100A9), C-C Motif Chemokine Ligand 17 (CCL17), C-C Motif Chemokine Ligand 18 (CCL18), C-C Motif Chemokine Ligand 19 (CCL19), C-C Motif Chemokine Ligand 26 (CCL26), C-C Motif Chemokine Ligand 27 (CCL27), Nitric Oxide Synthetase 2 (NOS2) or a combination thereof. In some cases, the detecting comprises contacting the isolated nucleic acids with an additional set of probes that recognizes IL-13R, IL-4R, IL-17, IL-22, CXCL9, CXCL10, CXCL11, S100A7, S100A8, S100A9, CCL17, CCL18, CCL19, CCL26, CCL27, NOS2, or a combination thereof, and detects binding between IL-13R, IL-4R, IL-17, IL-22, CXCL9, CXCL10, CXCL11, S100A7, S100A8, S100A9, CCL17, CCL18, CCL19, CCL26, CCL27, NOS2, or a combination thereof and the additional set of probes.

In some cases, the additional set of probes recognizes one but no more than ten genes. In some cases, the additional set of probes recognizes 2, 3, 4, 5, 6, 7, 8, 9, 10, 11, 12, 13, 14, 15, or 16 genes selected from IL-13R, IL-4R, IL-17, IL-22, CXCL9, CXCL10, CXCL11, S100A7, S100A8, S100A9, CCL17, CCL18, CCL19, CCL26, CCL27, and NOS2.

In some cases, the expression level of one or more genes selected from IL-13R, IL-4R, IL-17, IL-22, CXCL9, CXCL10, CXCL11, S100A7, S100A8, S100A9, CCL17, CCL18, CCL19, CCL26, CCL27, and NOS2 is an elevated gene expression level. In such cases, the gene expression level is elevated by at least 1-fold, 2-fold, 3-fold, 4-fold, 5-fold, 10-fold, 20-fold, 30-fold, 40-fold, 50-fold, 60-fold, 70-fold, 80-fold, 90-fold, 100-fold, 110-fold, 120-fold, 130-fold, 150-fold, 200-fold, 300-fold, 500-fold, or more. In some instances, the gene expression level is elevated by at least 10%, 20%, 30%, 40%, 50%, 60%, 70%, 80%, 90%, 100%, 200%, 300%, 400%, 500%, or more. In some instances, the expression level is compared to a gene expression level of an equivalent gene from a control sample. In some instances, the control sample is a normal skin sample.

In some embodiments, a method described herein further comprises detecting a skin region affected with atopic dermatitis. In some cases, also described herein include a method monitoring the skin region affected with atopic dermatitis, for about 1 week, 2 weeks, 3 weeks, 1 month, 2 months, 6 months, or more.

In some instances, the method has an improved specificity, of at least or about 70%, 75%, 80%, 85%, 90%, or more than 95% when detecting the gene expression level of IL-13, IL-31, TSLP, or a combination thereof. In some embodiments, the specificity is at least or about 70%, 75%, 80%, 85%, 90%, or more than 95% when detecting the gene expression level of IL-13R, IL-4R, IL-17, IL-22, CXCL9, CXCL10, CXCL11, S100A7, S100A8, S100A9, CCL17, CCL18, CCL19, CCL26, CCL27, NOS2, or a combination thereof.

In some cases, the method also has an improved sensitivity. In some embodiments, the sensitivity is at least or about 70%, 75%, 80%, 85%, 90%, or more than 95% when detecting the gene expression levels of IL-13, IL-31, TSLP, or a combination thereof. In some cases, the sensitivity is at least or about 70%, 75%, 80%, 85%, 90%, or more than 95% when detecting the gene expression levels of IL-13R, IL-4R, IL-17, IL-22, CXCL9, CXCL10, CXCL11, S100A7, S100A8, S100A9, CCL17, CCL18, CCL19, CCL26, CCL27, NOS2, or a combination thereof In some embodiments, a method described herein comprises detecting gene expression levels from a first gene classifier and a second gene classifier in a subject in need thereof, comprising: (a) isolating nucleic acids from a skin sample obtained from the subject, wherein the skin sample (e.g., comprising cells from the stratum corneum); (b) detecting the expression levels of one or more genes from the first gene classifier: IL-13, IL-31, and TSLP, by contacting the isolated nucleic acids with a set of probes that recognizes one or more genes from the first gene classifier, and detects binding between one or more genes from the first gene classifier and the set of probes; and (c) detecting the expression levels of one or more genes from the second gene classifier: IL-13R, IL-4R, IL-17, IL-22, CXCL9, CXCL10, CXCL11, S100A7, S100A8, S100A9, CCL17, CCL18, CCL19, CCL26, CCL27, and NOS2, by contacting the isolated nucleic acids with an additional set of probes that recognizes one or more genes from the second gene classifier, and detects binding between one or more genes from the second gene classifier and the additional set of probes.

Provided herein are methods for treatment of atopic dermatitis comprising administering one or more inhibitors described herein. Inhibitors for inclusion in methods for treatment of atopic dermatitis described herein include, but are not limited to, inhibitors of IL-13, PDE4, or IL-31. In some cases, the inhibitor for inclusion in the methods described herein for treatment of atopic dermatitis is an inhibitor of IL-13. In some cases, the inhibitor for inclusion in the methods described herein for treatment of atopic dermatitis is an inhibitor of PDE4. In some cases, the inhibitor for inclusion in the methods described herein for treatment of atopic dermatitis is an inhibitor of IL-31.

In some cases, the inhibitor of IL-13 includes, but is not limited to, lebrikizumab and tralokinumab. In some cases, the inhibitor of IL-13 is lebrikizumab. In some cases, the inhibitor of IL-13 is tralokinumab. In some cases, a subject is treated with an inhibitor of IL-13 such as lebrikizumab or tralokinumab.

In some instances, the PDE4 inhibitor includes, but is not limited to, crisaborole. In some instances, a subject is treated with a PDE4 inhibitor such as crisaborole.

In some instances, the IL-31 inhibitor includes, but is not limited to, nemolizumab. In some instances, a subject is treated with an IL-31 inhibitor such as nemolizumab.

Lupus Gene Classifiers and Methods of Use

In some embodiments, disclosed herein is a method of detecting the expression level of a gene from a gene classifier, which is associated with lupus erythematosus. In some instances, the method comprises detecting the expression level of Interferon Alpha 1 (IFNA1), Interferon Alpha 2 (IFNA2), Interferon Alpha 4 (IFNA4), Interferon Alpha And Beta Receptor Subunit 1 (IFNR1), Interferon Alpha And Beta Receptor Subunit 2 (IFNR2), C-C Motif Chemokine Ligand 5 (CCL5), or a combination thereof. In some instances, the method comprises (a) isolating nucleic acids from a skin sample obtained from the subject, wherein the skin sample (e.g., comprising cells from the stratum corneum); and (b) detecting the expression level of IFNA1, IFNA2, IFNA4, IFNR1, IFNR2, CCL5, or a combination thereof, by contacting the isolated nucleic acids with a set of probes that recognizes IFNA1, IFNA2, IFNA4, IFNR1, IFNR2, CCL5, or a combination thereof, and detects binding between IFNA1, IFNA2, IFNA4, IFNR1, IFNR2, CCL5, or a combination thereof and the set of probes.

In some embodiments, the method comprises detecting the expression levels of two or more, three or more, four or more, or five or more of genes from the gene classifier: IFNA1, IFNA2, IFNA4, IFNR1, IFNR2, and CCL5. In some cases, the method comprises detecting the expression levels of IFNA1, IFNA2, IFNA4, IFNR1, IFNR2, and CCL5. In some cases, the method comprises detecting the expression levels of IFNA1, IFNA2, IFNA4, IFNR1, and IFNR2. In some cases, the method comprises detecting the expression levels of IFNA1, IFNA2, IFNA4, and IFNR1. In some cases, the method comprises detecting the expression levels of IFNA1, IFNA2, and IFNA4. In some cases, the method comprises detecting the expression levels of IFNA1, IFNA4, and CCL5.

In some instances, the expression level is an upregulated gene expression level. In some instances, the expression level is an up-regulated gene expression level, compared to a gene expression level of an equivalent gene from a control sample. In some cases, the control sample is a normal skin sample. In some cases, the gene expression level of IFNA1, IFNA2, IFNA4, IFNR1, IFNR2, CCL5, or a combination thereof is up-regulated. In some instances, the up-regulated gene expression level occurs in areas of skin comprising lupus lesions.

In some instances, the gene expression level of IFNA1, IFNA2, IFNA4, IFNR1, IFNR2, or CCL5 is increased by at least 1-fold, 2-fold, 3-fold, 4-fold, 5-fold, 10-fold, 20-fold, 30-fold, 40-fold, 50-fold, 60-fold, 70-fold, 80-fold, 90-fold, 100-fold, 110-fold, 120-fold, 130-fold, 150-fold, 200-fold, 300-fold, 500-fold, or more. In some cases, the gene expression level of IFNA1, IFNA2, IFNA4, IFNR1, IFNR2, or CCL5 is increased by at least 10-fold. In some cases, the gene expression level of IFNA1, IFNA2, IFNA4, IFNR1, IFNR2, or CCL5 is increased by at least 20-fold. In some cases, the gene expression level of IFNA1, IFNA2, IFNA4, IFNR1, IFNR2, or CCL5 is increased by at least 30-fold. In some cases, the gene expression level of IFNA1, IFNA2, IFNA4, IFNR1, IFNR2, or CCL5 is increased by at least 40-fold. In some cases, the gene expression level of IFNA1, IFNA2, IFNA4, IFNR1, IFNR2, or CCL5 is increased by at least 50-fold. In some cases, the gene expression level of IFNA1, IFNA2, IFNA4, IFNR1, IFNR2, or CCL5 is increased by at least 80-fold. In some cases, the gene expression level of IFNA1, IFNA2, IFNA4, IFNR1, IFNR2, or CCL5 is increased by at least 100-fold. In some cases, the gene expression level of IFNA1, IFNA2, IFNA4, IFNR1, IFNR2, or CCL5 is increased by at least 130-fold. In some cases, the gene expression level of IFNA1, IFNA2, IFNA4, IFNR1, IFNR2, or CCL5 is increased by at least 150-fold. In some cases, the gene expression level of IFNA1, IFNA2, IFNA4, IFNR1, IFNR2, or CCL5 is increased by at least 200-fold. In some cases, the gene expression level of IFNA1, IFNA2, IFNA4, IFNR1, IFNR2, or CCL5 is increased by at least 300-fold. In some cases, the gene expression level of IFNA1, IFNA2, IFNA4, IFNR1, IFNR2, or CCL5 is increased by at least 500-fold. In some cases, the increased gene expression level is compared to a gene expression level of an equivalent gene from a control sample. In some cases, the control sample is a normal skin sample. In some instances, the up-regulated gene expression level occurs in areas of skin comprising lupus lesions.

In some cases, the gene expression level of IFNA1, IFNA2, IFNA4, IFNR1, IFNR2, or CCL5 is increased by at least 10%, 20%, 30%, 40%, 50%, 60%, 70%, 80%, 90%, 100%, 200%, 300%, 400%, 500%, or more. In some cases, the gene expression level of IFNA1, IFNA2, IFNA4, IFNR1, IFNR2, or CCL5 is increased by at least 10%. In some cases, the gene expression level of IFNA1, IFNA2, IFNA4, IFNR1, IFNR2, or CCL5 is increased by at least 20%. In some cases, the gene expression level of IFNA1, IFNA2, IFNA4, IFNR1, IFNR2, or CCL5 is increased by at least 30%. In some cases, the gene expression level of IFNA1, IFNA2, IFNA4, IFNR1, IFNR2, or CCL5 is increased by at least 40%. In some cases, the gene expression level of IFNA1, IFNA2, IFNA4, IFNR1, IFNR2, or CCL5 is increased by at least 50%. In some cases, the gene expression level of IFNA1, IFNA2, IFNA4, IFNR1, IFNR2, or CCL5 is increased by at least 80%. In some cases, the gene expression level of IFNA1, IFNA2, IFNA4, IFNR1, IFNR2, or CCL5 is increased by at least 90%. In some cases, the gene expression level of IFNA1, IFNA2, IFNA4, IFNR1, IFNR2, or CCL5 is increased by at least 100%. In some cases, the gene expression level of IFNA1, IFNA2, IFNA4, IFNR1, IFNR2, or CCL5 is increased by at least 150%. In some cases, the gene expression level of IFNA1, IFNA2, IFNA4, IFNR1, IFNR2, or CCL5 is increased by at least 200%. In some cases, the gene expression level of IFNA1, IFNA2, IFNA4, IFNR1, IFNR2, or CCL5 is increased by at least 300%. In some cases, the gene expression level of IFNA1, IFNA2, IFNA4, IFNR1, IFNR2, or CCL5 is increased by at least 500%. In some cases, the decreased gene expression level is compared to a gene expression level of an equivalent gene from a control sample. In some cases, the control sample is a normal skin sample. In some instances, the up-regulated gene expression level occurs in areas of skin comprising atopic dermatitis.

In some embodiments, the set of probes recognizes at least one but no more than six genes selected from IFNA1, IFNA2, IFNA4, IFNR1, IFNR2, and CCL5. In some cases, the set of probes recognizes IFNA1, IFNA2, and IFNA4. In some cases, the set of probes recognizes IFNR1, IFNR2, and CCL5. In some cases, the set of probes recognizes IFNA1, IFNA4, and IFNR2. In some cases, the set of probes recognizes IFNA2, IFNR1, and CCL5.

In some embodiments, the method further comprises detecting the expression levels of Interferon Beta 1 (IFNB1), Interferon Epsilon (IFNE), Interferon Omega 1 (IFNW1), Adenosine Deaminase, RNA Specific (ADAR), Interferon Induced proteins with Tetratricopeptide repeat (IFIT), interferon-inducible p200 family of proteins (IFI), Interferon Regulatory Factors (IRF), 2'-5'-Oligoadenylate Synthetase 1 (OAS1), Interleukin 1 Receptor Associated Kinase 1 (IRAK1), TNF Alpha Induced Protein 3 (TNFAIP3), Autophagy Related 5 (ATG5), Tyrosine Kinase 2 (TYK2), Signal Transducer and Activator Of Transcription 4 (STAT4), Osteopontin (OPN), Keratins (KRT), or a combination thereof. In some cases, the detecting comprises contacting the isolated nucleic acids with an additional set of probes that recognizes IFNB1, IFNE, IFNW1, ADAR, IFIT, IFI, IRF, OAS1, IRAK1, TNFAIP3, ATG5, TYK2, STAT4, OPN, KRT, or a combination thereof and the additional set of probes.

In some cases, the additional set of probes recognizes one but no more than ten genes. In some cases, the additional set of probes recognizes 2, 3, 4, 5, 6, 7, 8, 9, 10, 11, 12, 13, 14, or 15 genes selected from IFNB1, IFNE, IFNW1, ADAR, IFIT, IFI, IRF, OAS1, IRAK1, TNFAIP3, ATG5, TYK2, STAT4, OPN, and KRT.

In some cases, the expression level of one or more genes selected from IFNB1, IFNE, IFNW1, ADAR, IFIT, IFI, IRE, OAS1, IRAK1, TNFAIP3, ATG5, TYK2, STAT4, OPN, and KRT is an elevated gene expression level. In such cases, the gene expression level is elevated by at least 1-fold, 2-fold, 3-fold, 4-fold, 5-fold, 10-fold, 20-fold, 30-fold, 40-fold, 50-fold, 60-fold, 70-fold, 80-fold, 90-fold, 100-fold, 110-fold, 120-fold, 130-fold, 150-fold, 200-fold, 300-fold, 500-fold, or more. In some instances, the gene expression level is elevated by at least 10%, 20%, 30%, 40%, 50%, 60%, 70%, 80%, 90%, 100%, 200%, 300%, 400%, 500%, or more. In some instances, the expression level is compared to a gene expression level of an equivalent gene from a control sample. In some instances, the control sample is a normal skin sample.

In some embodiments, a method described herein further comprises detecting a skin region affected with lupus erythematosus. In some cases, also described herein include a method monitoring the skin region affected with lupus erythematosus, for about 1 week, 2 weeks, 3 weeks, 1 month, 2 months, 6 months, or more.

In some instances, the method has an improved specificity, of at least or about 70%, 75%, 80%, 85%, 90%, or more than 95% when detecting the gene expression level of IFNA1, IFNA2, IFNA4, IFNR1, IFNR2, CCL5, or a combination thereof. In some embodiments, the specificity is at least or about 70%, 75%, 80%, 85%, 90%, or more than 95% when detecting the gene expression level of IFNB1, IFNE, IFNW1, ADAR, IFIT, IFI, IRE, OAS1, IRAK1, TNFAIP3, ATG5, TYK2, STAT4, OPN, KRT, or a combination thereof.

In some cases, the method also has an improved sensitivity. In some embodiments, the sensitivity is at least or about 70%, 75%, 80%, 85%, 90%, or more than 95% when detecting the gene expression levels of IFNA1, IFNA2, IFNA4, IFNR1, IFNR2, CCL5, or a combination thereof. In some cases, the sensitivity is at least or about 70%, 75%, 80%, 85%, 90%, or more than 95% when detecting the gene expression levels of IFNB1, IFNE, IFNW1, ADAR, IFIT, IFI, IRF, OAS1, IRAK1, TNFAIP3, ATG5, TYK2, STAT4, OPN, KRT, or a combination thereof.

In some embodiments, a method described herein comprises detecting gene expression levels from a first gene classifier and a second gene classifier in a subject in need thereof, comprising: (a) isolating nucleic acids from a skin sample obtained from the subject, wherein the skin sample (e.g., comprising cells from the stratum corneum); (b) detecting the expression levels of one or more genes from the first gene classifier: IFNA1, IFNA2, IFNA4, IFNR1, IFNR2, and CCL5, by contacting the isolated nucleic acids with a set of probes that recognizes one or more genes from the first gene classifier, and detects binding between one or more genes from the first gene classifier and the set of probes; and (c) detecting the expression levels of one or more genes from the second gene classifier: IFNB1, IFNE, IFNW1, ADAR, IFIT, IFI, IRF, OAS1, IRAK1, TNFAIP3, ATG5, TYK2, STAT4, OPN, and KRT, by contacting the isolated nucleic acids with an additional set of probes that recognizes one or more genes from the second gene classifier, and detects binding between one or more genes from the second gene classifier and the additional set of probes.

Current treatment forms of lupus are focused on induction therapy to achieve remission and long-term maintenance therapy to prevent relapse. Management of cutaneous forms of the disease can include treatment with antimalarials, dapsone, retinoids, corticosteroids, immunosuppressive drugs, or thalidomide. In some instances, the animalarial hydroxychloroquine has been shown to decrease flares and assist in long-term management of disease. A recent study has shown that Janus kinase inhibitors (Jakinibs) are efficacious in improving disease symptoms in mice (Mok, C C, Expert Opin Investig Drugs. 2019 January; 28(1):85-92).

Provided herein are methods for treatment of a subject determined to have lupus by a non-inventive method described herein. Compositions for inclusion in methods for treatment of lupus described herein include, but are not limited to, antimalarials, dapsone, retinoids, corticosteroids, immunosuppressive drugs, thalidomide, Janus kinase inhibitors, baricitinib or any combination thereof. In some cases, the composition for inclusion in the methods described herein for treatment of lupus comprises an antimalarial. In some cases, the composition for inclusion in the methods described herein for treatment of lupus comprises dapsone. In some cases, the composition for inclusion in the methods described herein for treatment of lupus comprises a retinoid. In some cases, the composition for inclusion in the methods described herein for treatment of lupus comprises a corticosteroid. In some cases, the composition for inclusion in the methods described herein for treatment of lupus comprises an immunosuppressive drug. In some cases, the composition for inclusion in the methods described herein for treatment of lupus comprises thalidomide. In some cases, the composition for inclusion in the methods described herein for treatment of lupus comprises a Janus kinase inhibitor. In some cases, the composition for inclusion in the methods described herein for treatment of lupus comprises baricitinib.

In some cases, the antimalarial is hydroxychloroquine. In some cases, the antimalarial is quinacrine. In some cases, the antimalarial is chloroquine.

In some cases, the immunosuppressive drug is methotrexate. In some cases, the immunosuppressive drug is azathioprine.

Diagnostic Tools and Methods

In some embodiments, one or more genes are detected with a set of probes. In some embodiments, the set of probes comprises at least or about 1, 2, 3, 5, 6, 7, 8, 9, 10, 11, 12, 13, 14, 15, 16, 17, 18, 19, 20, 25, 30, or more than 30 probes. In some embodiments, the set of probes comprises about 6 probes. In some embodiments, the set of probes comprises about 7 probes. In some embodiments, the set of probes comprises about 8 probes. In some embodiments, the set of probes comprises about 9 probes. In some embodiments, the set of probes comprises about 10 probes. In some embodiments, the set of probes comprises about 13 probes. In some embodiments, the set of probes comprises about 15 probes. In some embodiments, the set of probes comprises about 20 probes.

In some embodiments, the set of probes comprises one or more primer pairs. In some embodiments, a number of primer pairs is at least or about 1, 2, 3, 5, 6, 7, 8, 9, 10, 11, 12, 13, 14, 15, 16, 17, 18, 19, 20, 25, 30, or more than 30 primer pairs. In some embodiments, the number of primer pairs is about 8 primer pairs. In some embodiments, the number of primer pairs is about 9 primer pairs. In some embodiments, the number of primer pairs is about 10 primer pairs.

In some embodiments, one or more probes in the set of probes is labeled. In some embodiments, the one or more probe is labeled with a radioactive label, a fluorescent label, an enzyme, a chemiluminescent tag, a colorimetric tag, an affinity tag or other labels or tags that are known in the art.

Exemplary affinity tags include, but are not limited to, biotin, desthiobiotin, histidine, polyhistidine, myc, hemagglutinin (HA), FLAG, glutathione S transferase (GST), or derivatives thereof. In some embodiments, the affinity tag is recognized by avidin, streptavidin, nickel, or glutathione.

In some embodiments, the fluorescent label is a fluorophore, a fluorescent protein, a fluorescent peptide, quantum dots, a fluorescent dye, a fluorescent material, or variations or combinations thereof.

Exemplary fluorophores include, but are not limited to, Alexa-Fluor dyes (e.g., Alexa Fluor® 350, Alexa Fluor® 405, Alexa Fluor® 430, Alexa Fluor® 488, Alexa Fluor® 500, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 647, Alexa Fluor® 660, Alexa Fluor® 680, Alexa Fluor® 700, and Alexa Fluor® 750), APC, Cascade Blue, Cascade Yellow and R-phycoerythrin (PE), DyLight 405, DyLight 488, DyLight 550, DyLight 650, DyLight 680, DyLight 755, DyLight 800, FITC, Pacific Blue, PerCP, Rhodamine, and Texas Red, Cy5, Cy5.5, Cy7.

Examples of fluorescent peptides include GFP (Green Fluorescent Protein) or derivatives of GFP (e.g., EBFP, EBFP2, Azurite, mKalamal, ECFP, Cerulean, CyPet, YFP, Citrine, Venus, and YPet.

Examples of fluorescent dyes include, but are not limited to, xanthenes (e.g., rhodamines, rhodols and fluoresceins, and their derivatives); bimanes; coumarins and their derivatives (e.g., umbelliferone and aminomethyl coumarins); aromatic amines (e.g., dansyl; squarate dyes); benzofurans; fluorescent cyanines; indocarbocyanines; carbazoles; dicyanomethylene pyranes; polymethine; oxabenzanthrane; xanthene; pyrylium; carbostyl; perylene; acridone; quinacridone; rubrene; anthracene; coronene; phenanthrecene; pyrene; butadiene; stilbene; porphyrin; pthalocyanine; lanthanide metal chelate complexes; rare-earth metal chelate complexes; and derivatives of such dyes. In some embodiments, the fluorescein dye is, but not limited to, 5-carboxyfluorescein, fluorescein-5-isothiocyanate, fluorescein-6-isothiocyanate and 6-carboxyfluorescein. In some embodiments, the rhodamine dye is, but not limited to, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, and rhodamine 101 sulfonyl chloride (sold under the tradename of TEXAS RED®). In some embodiments, the cyanine dye is Cy3, Cy3B, Cy3.5, Cy5, Cy5.5, Cy7, IRDYE680, Alexa Fluor 750, IRDye800CW, or ICG.

In some embodiments, the gene expression levels of IL-13, TSLP, IL-31, or a combination thereof is measured using PCR. Examples of PCR techniques include, but are not limited to quantitative PCR (qPCR), single cell PCR, PCR-RFLP, digital PCR (dPCR), droplet digital PCR (ddPCR), single marker qPCR, hot start PCR, and Nested PCR.

In some embodiments, the gene expression levels of IL-13R, IL-4R, IL-17, IL-22, CXCL9, CXCL10, CXCL11, S100A7, S100A8, S100A9, CCL17, CCL18, CCL19, CCL26, CCL27, NOS2, or a combination thereof is measured using PCR. Examples of PCR techniques include, but are not limited to quantitative PCR (qPCR), single cell PCR, PCR-RFLP, digital PCR (dPCR), droplet digital PCR (ddPCR), single marker qPCR, hot start PCR, and Nested PCR.

In some embodiments, the gene expression levels of IL-17A, IL-17F, IL-8, CXCL5, S100A9, DEFB4A, or a combination thereof is measured using PCR. Examples of PCR techniques include, but are not limited to quantitative PCR (qPCR), single cell PCR, PCR-RFLP, digital PCR (dPCR), droplet digital PCR (ddPCR), single marker qPCR, hot start PCR, and Nested PCR.

In some embodiments, the gene expression levels of IL-17C, S100A7, IL-17RA, IL-17RC, IL-23A, IL-22, IL-6, IL-24, IL-6, CXCL1, IFN-gamma, IL-31, IL-33, TNFα, LCN2, CCL20, and TNFRSF1A, or a combination thereof is measured using PCR. Examples of PCR techniques include, but are not limited to quantitative PCR (qPCR), single cell PCR, PCR-RFLP, digital PCR (dPCR), droplet digital PCR (ddPCR), single marker qPCR, hot start PCR, and Nested PCR.

In some embodiments, the gene expression levels of IFNA1, IFNA2, IFNA4, IFNR1, IFNR2, CCL5, or a combination thereof is measured using PCR. Examples of PCR techniques include, but are not limited to quantitative PCR (qPCR), single cell PCR, PCR-RFLP, digital PCR (dPCR), droplet digital PCR (ddPCR), single marker qPCR, hot start PCR, and Nested PCR.

In some embodiments, the gene expression levels of IFNB1, IFNE, IFNW1, ADAR, IFIT, IFI, IRF, OAS1, IRAK1, TNFAIP3, ATG5, TYK2, STAT4, OPN, KRT, or a combination thereof is measured using PCR. Examples of PCR techniques include, but are not limited to quantitative PCR (qPCR), single cell PCR, PCR-RFLP, digital PCR (dPCR), droplet digital PCR (ddPCR), single marker qPCR, hot start PCR, and Nested PCR.

In some embodiments, the expression levels are measured using qPCR. In some embodiments, the qPCR comprises use of fluorescent dyes or fluorescent probes. In some embodiments, the fluorescent dye is an intercalating dye. Examples of intercalating dyes include, but are not limited to, intercalating dyes include SYBR green I, SYBR green II, SYBR gold, ethidium bromide, methylene blue, Pyronin Y, DAPI, acridine orange, Blue View, or phycoerythrin. In some embodiments, the qPCR comprises use of more than one fluorescent probe. In some embodiments, the use of more than one fluorescent probes allows for multiplexing. For example, different non-classical variants are hybridized to different fluorescent probes and can be detected in a single qPCR reaction.

Components of the Skin Collection Kit

In some embodiments, the adhesive patch from the sample collection kit described herein comprises a first collection area comprising an adhesive matrix and a second area extending from the periphery of the first collection area. The adhesive matrix is located on a skin facing surface of the first collection area. The second area functions as a tab, suitable for applying and removing the adhesive patch. The tab is sufficient in size so that while applying the adhesive patch to a skin surface, the applicant does not come in contact with the matrix material of the first collection area. In some embodiments, the adhesive patch does not contain a second area tab. In some instances, the adhesive patch is handled with gloves to reduce contamination of the adhesive matrix prior to use.

In some embodiments, the first collection area is a polyurethane carrier film. In some embodiments, the adhesive matrix is comprised of a synthetic rubber compound. In some embodiments, the adhesive matrix is a styrene-isoprene-styrene (SIS) linear block copolymer compound. In some instances, the adhesive patch does not comprise latex, silicone, or both. In some instances, the adhesive patch is manufactured by applying an adhesive material as a liquid-solvent mixture to the first collection area and subsequently removing the solvent.

The matrix material is sufficiently sticky to adhere to a skin sample. The matrix material is not so sticky that is causes scarring or bleeding or is difficult to remove. In some embodiments, the matrix material is comprised of a transparent material. In some instances, the matrix material is biocompatible. In some instances, the matrix material does not leave residue on the surface of the skin after removal. In certain instances, the matrix material is not a skin irritant.

In some embodiments, the adhesive patch comprises a flexible material, enabling the patch to conform to the shape of the skin surface upon application. In some instances, at least the first collection area is flexible. In some instances, the tab is plastic. In an illustrative example, the adhesive patch does not contain latex, silicone, or both. In some embodiments, the adhesive patch is made of a transparent material, so that the skin sampling area of the subject is visible after application of the adhesive patch to the skin surface. The transparency ensures that the adhesive patch is applied on the desired area of skin comprising the skin area to be sampled. In some embodiments, the adhesive patch is between about 5 and about 100 mm in length. In some embodiments, the first collection area is between about 5 and about 40 mm in length. In some embodiments, the first collection area is between about 10 and about 20 mm in length. In some embodiments the length of the first collection area is configured to accommodate the area of the skin surface to be sampled, including, but not limited to, about 19 mm, about 20 mm, about 21 mm, about 22 mm, about 23 mm, about 24 mm, about 25 mm, about 30 mm, about 35 mm, about 40 mm, about 45 mm, about 50 mm, about 55 mm, about 60 mm, about 65 mm, about 70 mm, about 75 mm, about 80 mm, about 85 mm, about 90 mm, and about 100 mm. In some embodiments, the first collection area is elliptical.

In further embodiments, the adhesive patch of this invention is provided on a peelable release sheet in the adhesive skin sample collection kit. In some embodiments, the adhesive patch provided on the peelable release sheet is configured to be stable at temperatures between $-80°$ C. and $30°$ C. for at least 6 months, at least 1 year, at least 2 years, at least 3 years, and at least 4 years. In some instances, the peelable release sheet is a panel of a tri-fold skin sample collector.

In some instances, nucleic acids are stable on adhesive patch or patches when stored for a period of time or at a particular temperature. In some instances, the period of time is at least or about 1 day, 2 days, 3 days, 4 days, 5 days, 6 days, 7 days, 2 weeks, 3 weeks, 4 weeks, or more than 4 weeks. In some instances, the period of time is about 7 days. In some instances, the period of time is about 10 days. In some instances, the temperature is at least or about $-80°$ C., $-70°$ C., $-60°$ C., $-50°$ C., $-40°$ C., $-20°$ C., $-10°$ C., $-4°$ C., $0°$ C., $5°$ C., $15°$ C., $18°$ C., $20°$ C., $25°$ C., $30°$ C., $35°$ C., $40°$ C., $45°$ C., $50°$ C., or more than $50°$ C. The nucleic acids on the adhesive patch or patches, in some embodiments, are stored for any period of time described herein and any particular temperature described herein. For example, the nucleic acids on the adhesive patch or patches are stored for at least or about 7 days at about $25°$ C., 7 days at about $30°$ C., 7 days at about $40°$ C., 7 days at about $50°$ C., 7 days at about $60°$ C., or 7 days at about $70°$ C. In some instances, the nucleic acids on the adhesive patch or patches are stored for at least or about 10 days at about $-80°$ C.

The peelable release sheet, in certain embodiments, is configured to hold a plurality of adhesive patches, including, but not limited to, 12, 11, 10, 9, 8, 7, 6, 5, 4, 3, 2, 1, from about 2 to about 8, from about 2 to about 7, from about 2 to about 6, from about 2 to about 4, from about 3 to about 6, from about 3 to about 8, from about 4 to about 10, from about 4 to about 8, from about 4 to about 6, from about 4 to about 5, from about 6 to about 10, from about 6 to about 8, or from about 4 to about 8. In some instances, the peelable release sheet is configured to hold about 12 adhesive patches. In some instances, the peelable release sheet is configured to hold about 11 adhesive patches. In some instances, the peelable release sheet is configured to hold about 10 adhesive patches. In some instances, the peelable release sheet is configured to hold about 9 adhesive patches. In some instances, the peelable release sheet is configured to hold about 8 adhesive patches. In some instances, the peelable release sheet is configured to hold about 7 adhesive patches. In some instances, the peelable release sheet is configured to hold about 6 adhesive patches. In some instances, the peelable release sheet is configured to hold about 5 adhesive patches. In some instances, the peelable release sheet is configured to hold about 4 adhesive patches. In some instances, the peelable release sheet is configured to hold about 3 adhesive patches. In some instances, the peelable release sheet is configured to hold about 2 adhesive patches. In some instances, the peelable release sheet is configured to hold about 1 adhesive patch.

Provided herein, in certain embodiments, are methods and compositions for obtaining a sample using an adhesive patch, wherein the adhesive patch is applied to the skin and removed from the skin. After removing the used adhesive patch from the skin surface, the patch stripping method, in some instances, further comprise storing the used patch on a placement area sheet, where the patch remains until the skin sample is isolated or otherwise utilized. In some instances, the used patch is configured to be stored on the placement area sheet for at least 1 week at temperatures between −80° C. and 30° C. In some embodiments, the used patch is configured to be stored on the placement area sheet for at least 2 weeks, at least 3 weeks, at least 1 month, at least 2 months, at least 3 months, at least 4 months, at least 5 months, and at least 6 months at temperatures between −80° C. to 30° C.

In some instances, the placement area sheet comprises a removable liner, provided that prior to storing the used patch on the placement area sheet, the removable liner is removed. In some instances, the placement area sheet is configured to hold a plurality of adhesive patches, including, but not limited to, 12, 11, 10, 9, 8, 7, 6, 5, 4, 3, 2, 1, from about 2 to about 8, from about 2 to about 7, from about 2 to about 6, from about 2 to about 4, from about 3 to about 6, from about 3 to about 8, from about 4 to about 10, from about 4 to about 8, from about 4 to about 6, from about 4 to about 5, from about 6 to about 10, from about 6 to about 8, or from about 4 to about 8. In some instances, the placement area sheet is configured to hold about 12 adhesive patches. In some instances, the placement area sheet is configured to hold about 11 adhesive patches. In some instances, the placement area sheet is configured to hold about 10 adhesive patches. In some instances, the placement area sheet is configured to hold about 9 adhesive patches. In some instances, the placement area sheet is configured to hold about 8 adhesive patches. In some instances, the placement area sheet is configured to hold about 7 adhesive patches. In some instances, the placement area sheet is configured to hold about 6 adhesive patches. In some instances, the placement area sheet is configured to hold about 5 adhesive patches. In some instances, the placement area sheet is configured to hold about 4 adhesive patches. In some instances, the placement area sheet is configured to hold about 3 adhesive patches. In some instances, the placement area sheet is configured to hold about 2 adhesive patches. In some instances, the placement area sheet is configured to hold about 1 adhesive patch.

The used patch, in some instances, is stored so that the matrix containing, skin facing surface of the used patch is in contact with the placement area sheet. In some instances, the placement area sheet is a panel of the tri-fold skin sample collector. In some instances, the tri-fold skin sample collector further comprises a clear panel. In some instances, the tri-fold skin sample collector is labeled with a unique barcode that is assigned to a subject. In some instances, the tri-fold skin sample collector comprises an area for labeling subject information.

In an illustrative embodiment, the adhesive skin sample collection kit comprises the tri-fold skin sample collector comprising adhesive patches stored on a peelable release panel. In some instances, the tri-fold skin sample collector further comprises a placement area panel with a removable liner. In some instances, the patch stripping method involves removing an adhesive patch from the tri-fold skin sample collector peelable release panel, applying the adhesive patch to a skin sample, removing the used adhesive patch containing a skin sample and placing the used patch on the placement area sheet. In some instances, the placement area panel is a single placement area panel sheet. In some instances, the identity of the skin sample collected is indexed to the tri-fold skin sample collector or placement area panel sheet by using a barcode or printing patient information on the collector or panel sheet. In some instances, the indexed tri-fold skin sample collector or placement sheet is sent to a diagnostic lab for processing. In some instances, the used patch is configured to be stored on the placement panel for at least 1 week at temperatures between −80° C. and 25° C. In some embodiments, the used patch is configured to be stored on the placement area panel for at least 2 weeks, at least 3 weeks, at least 1 month, at least 2 months, at least 3 months, at least 4 months, at least 5 months, and at least 6 months at temperatures between −80° C. and 25° C. In some embodiments, the indexed tri-fold skin sample collector or placement sheet is sent to a diagnostic lab using UPS or FedEx.

In an exemplary embodiment, the patch stripping method further comprises preparing the skin sample prior to application of the adhesive patch. Preparation of the skin sample includes, but is not limited to, removing hairs on the skin surface, cleansing the skin surface and/or drying the skin surface. In some instances, the skin surface is cleansed with an antiseptic including, but not limited to, alcohols, quaternary ammonium compounds, peroxides, chlorhexidine, halogenated phenol derivatives and quinolone derivatives. In some instances, the alcohol is about 0 to about 20%, about 20 to about 40%, about 40 to about 60%, about 60 to about 80%, or about 80 to about 100% isopropyl alcohol. In some instances, the antiseptic is 70% isopropyl alcohol.

In some embodiments, the patch stripping method is used to collect a skin sample from the surfaces including, but not limited to, the face, head, neck, arm, chest, abdomen, back, leg, hand or foot. In some instances, the skin surface is not located on a mucous membrane. In some instances, the skin surface is not ulcerated or bleeding. In certain instances, the skin surface has not been previously biopsied. In certain instances, the skin surface is not located on the soles of the feet or palms.

The patch stripping method, devices, and systems described herein are useful for the collection of a skin sample from a skin lesion. A skin lesion is a part of the skin that has an appearance or growth different from the surrounding skin. In some instances, the skin lesion is pigmented. A pigmented lesion includes, but is not limited to, a mole, dark colored skin spot and a melanin containing skin area. In some embodiments, the skin lesion is from about 5 mm to about 16 mm in diameter. In some instances, the skin lesion is from about 5 mm to about 15 mm, from about 5 mm to about 14 mm, from about 5 mm to about 13 mm, from about 5 mm to about 12 mm, from about 5 mm to about 11 mm, from about 5 mm to about 10 mm, from about 5 mm to about 9 mm, from about 5 mm to about 8 mm, from about 5 mm to about 7 mm, from about 5 mm to about 6 mm, from about 6 mm to about 15 mm, from about 7 mm to about 15 mm, from about 8 mm to about 15 mm, from about 9 mm to about 15 mm, from about 10 mm to about 15 mm, from about 11 mm to about 15 mm, from about 12 mm to about 15 mm, from about 13 mm to about 15 mm, from about 14 mm to about 15 mm, from about 6 to about 14 mm, from about 7 to about 13 mm, from about 8 to about 12 mm and from about 9 to about 11 mm in diameter. In some embodiments, the skin lesion is from about 10 mm to about 20 mm, from about 20 mm to about 30 mm, from about 30 mm to about 40 mm, from about 40 mm to about 50 mm, from about 50 mm to about 60 mm, from about 60 mm to about 70 mm, from about 70 mm to about 80 mm, from about 80 mm to about 90 mm, and from about 90 mm to about 100 mm in diameter. In some instances, the diameter is the longest diameter of the skin lesion. In some instances, the diameter is the smallest diameter of the skin lesion.

The adhesive skin sample collection kit, in some embodiments, comprises at least one adhesive patch, a sample collector, and an instruction for use sheet. In an exemplary embodiment, the sample collector is a tri-fold skin sample collector comprising a peelable release panel comprising at least one adhesive patch, a placement area panel comprising a removable liner, and a clear panel. The tri-fold skin sample collector, in some instances, further comprises a barcode and/or an area for transcribing patient information. In some instances, the adhesive skin sample collection kit is configured to include a plurality of adhesive patches, including but not limited to 12, 11, 10, 9, 8, 7, 6, 5, 4, 3, 2, 1, from about 2 to about 8, from about 2 to about 7, from about 2 to about 6, from about 2 to about 4, from about 3 to about 6, from about 3 to about 8, from about 4 to about 10, from about 4 to about 8, from about 4 to about 6, from about 4 to about 5, from about 6 to about 10, from about 6 to about 8, or from about 4 to about 8. The instructions for use sheet provide the kit operator all of the necessary information for carrying out the patch stripping method. The instructions for use sheet preferably include diagrams to illustrate the patch stripping method.

In some instances, the adhesive skin sample collection kit provides all the necessary components for performing the patch stripping method. In some embodiments, the adhesive skin sample collection kit includes a lab requisition form for providing patient information. In some instances, the kit further comprises accessory components. Accessory components include, but are not limited to, a marker, a resealable plastic bag, gloves and a cleansing reagent. The cleansing reagent includes, but is not limited to, an antiseptic such as isopropyl alcohol. In some instances, the components of the skin sample collection kit are provided in a cardboard box.

Cellular Material and Sample Process

The methods and devices provided herein, in certain embodiments, involve applying an adhesive or other similar patch to the skin in a manner so that an effective or sufficient amount of a tissue, such as a skin sample, adheres to the adhesive matrix of the adhesive patch. For example, the effective or sufficient amount of a skin sample is an amount that removably adheres to a material, such as the matrix or adhesive patch. The adhered skin sample, in certain embodiments, comprises cellular material including nucleic acids. In some instances, the nucleic acid is RNA or DNA. An effective amount of a skin sample contains an amount of cellular material sufficient for performing a diagnostic assay. In some instances, the diagnostic assay is performed using the cellular material isolated from the adhered skin sample on the used adhesive patch. In some instances, the diagnostic assay is performed on the cellular material adhered to the used adhesive patch. In some embodiments, an effect amount of a skin sample comprises an amount of RNA sufficient to perform a gene expression analysis. Sufficient amounts of RNA includes, but not limited to, picogram, nanogram, and microgram quantities.

In some instances, the nucleic acid is a RNA molecule or a fragmented RNA molecule (RNA fragments). In some instances, the RNA is a microRNA (miRNA), a pre-miRNA, a pri-miRNA, a mRNA, a pre-mRNA, a viral RNA, a viroid RNA, a virusoid RNA, circular RNA (circRNA), a ribosomal RNA (rRNA), a transfer RNA (tRNA), a pre-tRNA, a long non-coding RNA (lncRNA), a small nuclear RNA (snRNA), a circulating RNA, a cell-free RNA, an exosomal RNA, a vector-expressed RNA, a RNA transcript, a synthetic RNA, or combinations thereof. In some instances, the RNA is mRNA. In some instances, the RNA is cell-free circulating RNA.

In some instances, the nucleic acid is DNA. DNA includes, but not limited to, genomic DNA, viral DNA, mitochondrial DNA, plasmid DNA, amplified DNA, circular DNA, circulating DNA, cell-free DNA, or exosomal DNA. In some instances, the DNA is single-stranded DNA (ssDNA), double-stranded DNA, denaturing double-stranded DNA, synthetic DNA, and combinations thereof. In some instances, the DNA is genomic DNA. In some instances, the DNA is cell-free circulating DNA.

In additional embodiments, the adhered skin sample comprises cellular material including nucleic acids such as RNA or DNA, in an amount that is at least about 1 picogram. In some embodiments, the amount of cellular material is no more than about 1 nanogram. In further or additional embodiments, the amount of cellular material is no more than about 1 microgram. In still further or additional embodiments, the amount of cellular material is no more than about 1 gram.

In further or additional embodiments, the amount of cellular material is from about 1 picogram to about 1 gram. In further or additional embodiments, the cellular material comprises an amount that is from about 50 microgram to about 1 gram, from about 100 picograms to about 500 micrograms, from about 500 picograms to about 100 micrograms, from about 750 picograms to about 1 microgram, from about 1 nanogram to about 750 nanograms, or from about 1 nanogram to about 500 nanograms. In additional embodiments, the cellular material comprises an amount that is from about 50 picograms to about 1 micrograms, from about 100 picograms to about 500 picograms, from about 200 picograms to about 500 picograms, from about 500 picograms to about 1 nanograms, from about 500 picograms to about 500 nanograms, or from about 1 nanograms to about 500 nanograms.

In further or additional embodiments, the amount of cellular material, including nucleic acids such as RNA or DNA, comprises an amount that is from about 50 microgram to about 500 microgram, from about 100 microgram to about 450 microgram, from about 100 microgram to about 350 microgram, from about 100 microgram to about 300 microgram, from about 120 microgram to about 250 microgram, from about 150 microgram to about 200 microgram, from about 500 nanograms to about 5 nanograms, or from about 400 nanograms to about 10 nanograms, or from about 200 nanograms to about 15 nanograms, or from about 100 nanograms to about 20 nanograms, or from about 50 nanograms to about 10 nanograms, or from about 50 nanograms to about 25 nanograms. In some embodiments, the amount of cellular material, including nucleic acids such as RNA or DNA, comprises an amount that is from about picograms to about 1 micrograms, from about 100 picograms to about 500 picograms, from about 200 picograms to about 500 picograms, from about 500 picograms to about 1 nanograms, from about 500 picograms to about 500 nanograms, or from about 1 nanograms to about 500 nanograms.

In further or additional embodiments, the amount of cellular material, including nucleic acids such as RNA or DNA, is less than about 1 gram, is less than about 500 micrograms, is less than about 490 micrograms, is less than about 480 micrograms, is less than about 470 micrograms, is less than about 460 micrograms, is less than about 450 micrograms, is less than about 440 micrograms, is less than about 430 micrograms, is less than about 420 micrograms, is less than about 410 micrograms, is less than about 400 micrograms, is less than about 390 micrograms, is less than about 380 micrograms, is less than about 370 micrograms, is less than about 360 micrograms, is less than about 350 micrograms, is less than about 340 micrograms, is less than about 330 micrograms, is less than about 320 micrograms, is less than about 310 micrograms, is less than about 300 micrograms, is less than about 290 micrograms, is less than about 280 micrograms, is less than about 270 micrograms, is less than about 260 micrograms, is less than about 250 micrograms, is less than about 240 micrograms, is less than about 230 micrograms, is less than about 220 micrograms, is less than about 210 micrograms, is less than about 200 micrograms, is less than about 190 micrograms, is less than about 180 micrograms, is less than about 170 micrograms, is less than about 160 micrograms, is less than about 150 micrograms, is less than about 140 micrograms, is less than about 130 micrograms, is less than about 120 micrograms, is less than about 110 micrograms, is less than about 100 micrograms, is less than about 90 micrograms, is less than about 80 micrograms, is less than about 70 micrograms, is less than about 60 micrograms, is less than about 50 micrograms, is less than about 20 micrograms, is less than about 10 micrograms, is less than about 5 micrograms, is less than about 1 microgram, is less than about 750 nanograms, is less than about 500 nanograms, is less than about 250 nanograms, is less than about 150 nanograms, is less than about 100 nanograms, is less than about 50 nanograms, is less than about 25 nanograms, is less than about 15 nanograms, is less than about 1 nanogram, is less than about 750 picograms, is less than about 500 picograms, is less than about 250 picograms, is less than about 100 picograms, is less than about 50 picograms, is less than about 25 picograms, is less than about 15 picograms, or is less than about 1 picogram.

In some embodiments, isolated RNA from a collected skin sample is reverse transcribed into cDNA, for example for amplification by PCR to enrich for target genes. The expression levels of these target genes are quantified by quantitative PCR in a gene expression test. In some instances, in combination with quantitative PCR, a software program performed on a computer is utilized to quantify RNA isolated from the collected skin sample. In some instances, a software program or module is utilized to relate a quantity of RNA from a skin sample to a gene expression signature, wherein the gene expression signature is associated with a disease such as skin cancer. In some embodiments, a software program or module scores a sample based on gene expression levels. In some embodiments, the sample score is compared with a reference sample score to determine if there is a statistical significance between the gene expression signature and a disease.

In some instances, the layers of skin include epidermis, dermis, or hypodermis. The outer layer of epidermis is the stratum corneum layer, followed by stratum lucidum, stratum granulosum, stratum spinosum, and stratum basale. In some instances, the skin sample is obtained from the epidermis layer. In some cases, the skin sample is obtained from the stratum corneum layer. In some instances, the skin sample is obtained from the dermis.

In some instances, cells from the stratum corneum layer are obtained, which comprises keratinocytes. In some cases, melanocytes are not obtained from the skin sample.

Following extraction of nucleic acids from a biological sample, the nucleic acids, in some instances, are further purified. In some instances, the nucleic acids are RNA. In some instances, the nucleic acids are DNA. In some instances, the RNA is human RNA. In some instances, the DNA is human DNA. In some instances, the RNA is microbial RNA. In some instances, the DNA is microbial DNA. In some instances, human nucleic acids and microbial nucleic acids are purified from the same biological sample. In some instances, nucleic acids are purified using a column or resin based nucleic acid purification scheme. In some instances, this technique utilizes a support comprising a surface area for binding the nucleic acids. In some instances, the support is made of glass, silica, latex or a polymeric material. In some instances, the support comprises spherical beads.

Methods for isolating nucleic acids, in certain embodiments, comprise using spherical beads. In some instances, the beads comprise material for isolation of nucleic acids. Exemplary material for isolation of nucleic acids using beads include, but not limited to, glass, silica, latex, and a polymeric material. In some instances, the beads are magnetic. In some instances, the beads are silica coated. In some instances, the beads are silica-coated magnetic beads. In some instances, a diameter of the spherical bead is at least or about 0.5 um, 1 um, 1.5 um, 2 um, 2.5 um, 3 um, 3.5 um, 4 um, 4.5 um, 5 um, 5.5 um, 6 um, 6.5 um, 7 um, 7.5 um, 8 um, 8.5 um, 9 um, 9.5 um, 10 um, or more than 10 um.

In some cases, a yield of the nucleic acids products obtained using methods described herein is about 500 picograms or higher, about 600 picograms or higher, about 1000 picograms or higher, about 2000 picograms or higher, about 3000 picograms or higher, about 4000 picograms or higher, about 5000 picograms or higher, about 6000 picograms or higher, about 7000 picograms or higher, about 8000 picograms or higher, about 9000 picograms or higher, about 10000 picograms or higher, about 20000 picograms or higher, about 30000 picograms or higher, about 40000 picograms or higher, about 50000 picograms or higher, about 60000 picograms or higher, about 70000 picograms or higher, about 80000 picograms or higher, about 90000 picograms or higher, or about 100000 picograms or higher.

In some cases, a yield of the nucleic acids products obtained using methods described herein is about 100 picograms, 500 picograms, 600 picograms, 700 picograms, 800 picograms, 900 picograms, 1 nanogram, 5 nanograms, 10 nanograms, 15 nanograms, 20 nanograms, 21 nanograms, 22 nanograms, 23 nanograms, 24 nanograms, 25 nanograms, 26 nanograms, 27 nanograms, 28 nanograms, 29 nanograms, 30 nanograms, 35 nanograms, 40 nanograms, 50 nanograms, 60 nanograms, 70 nanograms, 80 nanograms, 90 nanograms, 100 nanograms, 500 nanograms, or higher.

In some cases, methods described herein provide less than less than 10%, less than 8%, less than 5%, less than 2%, less than 1%, or less than 0.5% product yield variations between samples.

In some cases, methods described herein provide a substantially homogenous population of a nucleic acid product.

In some cases, methods described herein provide less than 30%, less than 25%, less than 20%, less than 15%, less than 10%, less than 8%, less than 5%, less than 2%, less than 1%, or less than 0.5% contaminants.

In some instances, following extraction, nucleic acids are stored. In some instances, the nucleic acids are stored in water, Tris buffer, or Tris-EDTA buffer before subsequent analysis. In some instances, this storage is less than 8° C. In some instances, this storage is less than 4° C. In certain embodiments, this storage is less than 0° C. In some instances, this storage is less than −20° C. In certain embodiments, this storage is less than −70° C. In some instances, the nucleic acids are stored for about 1, 2, 3, 4, 5, 6, or 7 days. In some instances, the nucleic acids are stored for about 1, 2, 3, or 4 weeks. In some instances, the nucleic acids are stored for about 1, 2, 3, 4, 5, 6, 7, 8, 9, 10, 11, or 12 months.

In some instances, nucleic acids isolated using methods described herein are subjected to an amplification reaction following isolation and purification. In some instances, the nucleic acids to be amplified are RNA including, but not limited to, human RNA and human microbial RNA. In some instances, the nucleic acids to be amplified are DNA including, but not limited to, human DNA and human microbial DNA. Non-limiting amplification reactions include, but are not limited to, quantitative PCR (qPCR), self-sustained sequence replication, transcriptional amplification system, Q-Beta Replicase, rolling circle replication, or any other nucleic acid amplification known in the art. In some instances, the amplification reaction is PCR. In some instances, the amplification reaction is quantitative such as qPCR.

Provided herein are methods for detecting an expression level of one or more genes of interest from nucleic acids isolated from a biological sample. In some instances, the expression level is detected following an amplification reaction. In some instances, the nucleic acids are RNA. In some instances, the RNA is human RNA. In some instances, the RNA is microbial RNA. In some instances, the nucleic acids are DNA. In some instances, the DNA is human DNA. In some instances, the DNA is microbial DNA. In some instances, the expression level is determined using PCR. In some instances, the expression level is determined using qPCR. In some instances, the expression level is determined using a microarray. In some instances, the expression level is determined by sequencing.

Certain Terminologies

Unless defined otherwise, all technical and scientific terms used herein have the same meaning as is commonly understood by one of skill in the art to which the claimed subject matter belongs. It is to be understood that the detailed description are exemplary and explanatory only and are not restrictive of any subject matter claimed. In this application, the use of the singular includes the plural unless specifically stated otherwise. It must be noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

Markers

C-C Motif Chemokine Ligand 20 (CCL20), also known as small Inducible Cytokine Subfamily A (Cys-Cys), Member 20, MIP3A, or ST38, is a member of a family of small cytokine CC genes, the products of which are characterized by two adjacent cysteines. CCL20 encodes a protein with chemotactic activity for lymphocytes which can repress proliferation of myeloid progenitors. In some instances, CCL20 has Gene ID: 6364.

C-X-C Motif Chemokine Ligand 1 (CXCL1), also known as Chemokine (C-X-C Motif) Ligand 1, Fibroblast Secretory Protein, or GRO1, encodes a protein in the CXC subfamily of chemokines. CXCL1 encodes a secreted growth factor that signals through the G-protein coupled receptor, CXC receptor 2. In some instances, CXCL1 has Gene ID: 2919.

C-X-C Motif Chemokine Ligand 5 (CXCL5), also known as Small Inducible Cytokine Subfamily B (Cys-X-Cys), Member 5, ENA-78, or SCYB5, encodes a protein in the CXC subfamily of chemokines. The encoded protein is proposed to bind the G-protein coupled receptor chemokine (C-X-C motif) receptor 2 to recruit neutrophils, to promote angiogenesis, and to remodel connective tissues. In some instances, CXCL5 has Gene ID: 6374.

Defensin Beta 4A (DEFB4A), also known as Defensin Beta 4, HBD-2, or SAP1, is part of a family of microbicidal and cytotoxic peptides made by neutrophils. The encoded protein, defensin, beta 4, is an antibiotic peptide which is locally regulated by inflammation. In some instances, DEFB4A has Gene ID: 1673.

Interfereon Gamma (IFN-gamma), also known as IFN-gamma, or Immune Interferon, is part of the type II interferon class. The encoded protein is a homodimer that binds to the interferon gamma receptor to trigger a cellular response to viral and microbial infections. In some instances, IFNG has Gene ID: 3458.

Interleukin 17A (IL-17A), also known as IL-17, CTLA-8 or Cytotoxic T-Lymphocyte-Associated Protein 8, is a proinflammatory cytokine produced by activated T cells. This cytokine regulates the activities of NF-kappaB and mitogen-activated protein kinases and can stimulate the expression of IL6 and cyclooxygenase-2 (PTGS2/COX-2), as well as enhance the production of nitric oxide (NO). In some instances, IL-17A has Gene ID: 3605.

Interleukin 17C (IL-17C), also known as Cytokine CX2, is a T cell-derived cytokine that shares sequence similarity with IL17. This cytokine releases tumor necrosis factor alpha and interleukin 1 beta from a monocytic cell line. Expression of this cytokine is restricted to activated T cells. In some instances, IL-17C has Gene ID: 27189.

Interleukin 17F (IL-17F), also known as Cytokine ML-1 or CANDF6, is a cytokine that shares sequence similarity with IL17. This cytokine is expressed by activated T cells, and stimulates the production of several other cytokines, including IL6, IL8, and CSF2/GM_CSF. This cytokine also inhibits the angiogenesis of endothelial cells and induces endothelial cells to produce IL2, TGFB1/TGFB, and monocyte chemoattractant protein-1. In some instances, IL-17F has Gene ID: 112744.

Interleukin 17 Receptor A (IL-17RA), also known as CDw217 or IL17R, is a proinflammatory cytokine secreted by activated T-lymphocytes. It is a potent inducer of the maturation of CD34-positive hematopoietic precursors into neutrophils. The transmembrane protein encoded by this gene (interleukin 17A receptor; IL17RA) is a ubiquitous type I membrane glycoprotein that binds with low affinity to interleukin 17A. Interleukin 17A and its receptor play a pathogenic role in many inflammatory and autoimmune diseases such as rheumatoid arthritis. In some instances, IL-17RA has Gene ID: 23765.

Interleukin 17 Receptor C (IL-17RC), also known as ZcytoR14, IL17Rhom, Interleukin-17 Receptor-Like Protein, or CANDF9, encodes a single-pass type I membrane protein that shares similarity with the interleukin-17 receptor (IL-17RA). The protein is expressed in nonhemopoietic tissues, and binds both IL-17A and IL-17F with similar affinities. Multiple alternatively spliced transcript variants encoding different isoforms have been detected for this gene, and soluble, secreted proteins lacking transmembrane and intracellular domains may function as extracellular antagonists to cytokine signaling. In some instances, IL-17RC has Gene ID: 84818.

Interleukin 22 (IL-22), also known as Cytokine Zcyto18, IL-TIF, IL-D110, or TIFa, is a member of the IL10 family of cytokines that mediate cellular inflammatory responses. The encoded protein functions in antimicrobial defense at mucosal surfaces and in tissue repair. This protein also has pro-inflammatory properties and plays a role in in the pathogenesis of several intestinal diseases. In some instances, IL-22 has Gene ID: 50616.

Interleukin 23 Subunit Alpha (IL-23A), also known as IL-23, SGRF, or P19, encodes a subunit of the heterodimeric cytokine interleukin 23 (IL23). IL23 is composed of this protein and the p40 subunit of interleukin 12 (IL12B). The receptor of IL23 is formed by the beta 1 subunit of IL12 (IL12RB1) and an IL23 specific subunit, IL23R. Both IL23 and IL12 can activate the transcription activator STAT4, and stimulate the production of interferon-gamma (IFNG). In contrast to IL12, which acts mainly on naive CD4(+) T cells, IL23 preferentially acts on memory CD4(+) T cells. In some instances, IL-23A has Gene ID: 51561.

Interleukin 24 (IL-24), also known as ST16, MDA7, IL10B, or C49A, encodes a member of the IL10 family of cytokines. It was identified as a gene induced during terminal differentiation in melanoma cells. The protein encoded by this gene can induce apoptosis selectively in various cancer cells. Overexpression of this gene leads to elevated expression of several GADD family genes, which correlates with the induction of apoptosis. The phosphorylation of mitogen-activated protein kinase 14 (MAPK7/P38), and heat shock 27 kDa protein 1 (HSPB2/HSP27) are found to be induced by this gene in melanoma cells, but not in normal immortal melanocytes. In some instances, IL-24 has Gene ID: 11009.

Interleukin 26 (IL-26), also known as AK155, was identified by its overexpression specifically in herpesvirus samimiri-transformed T cells. The encoded protein is a member of the IL10 family of cytokines. It is a secreted protein and may function as a homodimer. This protein is thought to contribute to the transformed phenotype of T cells after infection by herpesvirus samimiri. In some instances, IL-26 has Gene ID: 55801.

Interleukin 31 (IL-31), also known as IL-31, which is made principally by activated Th2-type T cells, interacts with a heterodimeric receptor consisting of IL31RA (MIM 609510) and OSMR (MIM 601743) that is constitutively expressed on epithelial cells and keratinocytes. IL31 may be involved in the promotion of allergic skin disorders and in regulating other allergic diseases, such as asthma. In some instances, IL-31 has Gene ID: 386653.

Interleukin 33 (IL-33), also known as DVS27-Related Protein, C9orf26, IL1F11, or NFEHEV, encodes a protein that is a cytokine that binds to the IL1RL1/ST2 receptor. The encoded protein is involved in the maturation of Th2 cells and the activation of mast cells, basophils, eosinophils and natural killer cells. Several transcript variants encoding different isoforms have been found for this gene. In some instances, IL-33 has Gene ID: 90865.

Interleukin 5 (IL-5), also known as Eosinophil Differentiation Factor, T-Cell Replacing Factor, B-Cell Differentiation Factor I, TRF, or EDF, encodes a cytokine that acts as a growth and differentiation factor for both B cells and eosinophils. The encoded cytokine plays a major role in the regulation of eosinophil formation, maturation, recruitment and survival. The increased production of this cytokine may be related to pathogenesis of eosinophil-dependent inflammatory diseases. This cytokine functions by binding to its receptor, which is a heterodimer, whose beta subunit is shared with the receptors for interleukine 3 (IL3) and colony stimulating factor 2 (CSF2/GM-CSF). In some instances, IL-5 has Gene ID: 3567.

Interleukin 6 (IL-6), also known as B-Cell Stimulatory Factor 2, CTL Differentiation Factor, Hybridoma Growth Factor, or IFN-Beta-2, encodes a cytokine that functions in inflammation and the maturation of B cells. In addition, the encoded protein is an endogenous pyrogen capable of inducing fever in subjects with autoimmune diseases or infections. The protein is primarily produced at sites of acute and chronic inflammation, where it is secreted into the serum and induces a transcriptional inflammatory response through interleukin 6 receptor, alpha. The functioning of this gene is implicated in a wide variety of inflammation-associated disease states, including susceptibility to diabetes mellitus and systemic juvenile rheumatoid arthritis. In some instances, IL-6 has Gene ID: 3569.

Interleukin 8 (IL-8), also known as CXC Motif Chemokine Ligand 8, GCP-1, or NAP-1, encodes a protein that is a member of the CXC chemokine family and is a major mediator of the inflammatory response. The encoded protein is secreted primarily by neutrophils, where it serves as a chemotactic factor by guiding the neutrophils to the site of infection. This chemokine is also a potent angiogenic factor. This gene is believed to play a role in the pathogenesis of bronchiolitis, a common respiratory tract disease caused by viral infection. In some instances, IL-8 has Gene ID: 3576.

Lipocalin 2 (LCN2), also known as NGAL, P25, or 24p3, encodes a protein that belongs to the lipocalin family. Members of this family transport small hydrophobic molecules such as lipids, steroid hormones and retinoids. The protein encoded by this gene is a neutrophil gelatinase-associated lipocalin and plays a role in innate immunity by limiting bacterial growth as a result of sequestering iron-containing siderophores. In some instances, LCN2 has Gene ID: 3934.

S100 Calcium Binding Protein A7 (S100A7), also known as PSOR1 or Psoriasin, encodes a protein that is a member of the S100 family of proteins containing 2 EF-hand calcium-binding motifs. S100 proteins are localized in the cytoplasm and/or nucleus of a wide range of cells, and involved in the regulation of a number of cellular processes such as cell cycle progression and differentiation. The protein is overexpressed in hyperproliferative skin diseases, exhibits antimicrobial activities against bacteria and induces immunomodulatory activities. In some instances, S100A7 has Gene ID: 6278.

S100 Calcium Binding Protein A9 (S100A9), also known as MRP-14, CAGB, or L1AG, encodes a protein that is a member of the S100 family of proteins containing 2 EF-hand calcium-binding motifs. S100 proteins are localized in the cytoplasm and/or nucleus of a wide range of cells, and involved in the regulation of a number of cellular processes such as cell cycle progression and differentiation. S100 genes include at least 13 members which are located as a cluster on chromosome 1q21. This antimicrobial protein exhibits antifungal and antibacterial activity. In some instances, S100A9 has Gene ID: 6280.

Tumor Necrosis Factor (TNF), also known as TNF-alpha, Chachectin, or DIF, encodes a multifunctional proinflammatory cytokine that belongs to the tumor necrosis factor (TNF) superfamily. This cytokine is mainly secreted by macrophages. It can bind to, and thus functions through its receptors TNFRSF1A/TNFR1 and TNFRSF1B/TNFBR. This cytokine is involved in the regulation of a wide spectrum of biological processes including cell proliferation, differentiation, apoptosis, lipid metabolism, and coagulation. This cytokine has been implicated in a variety of diseases, including autoimmune diseases, insulin resistance, and cancer. In some instances, TNF has Gene ID: 7124.

TNF Receptor Superfamily Member 1A (TNF RSF1A), also known as TNF-R1, P55, P60, or CD120a Antigen, encodes a member of the TNF receptor superfamily of proteins. The encoded receptor is found in membrane-bound and soluble forms that interact with membrane-bound and soluble forms, respectively, of its ligand, tumor necrosis factor alpha. Binding of membrane-bound tumor necrosis factor alpha to the membrane-bound receptor induces receptor trimerization and activation, which plays a role in cell survival, apoptosis, and inflammation. Proteolytic processing of the encoded receptor results in release of the soluble form of the receptor, which can interact with free tumor necrosis factor alpha to inhibit inflammation. Mutations in this gene may also be associated with multiple sclerosis in human patients. In some instances, TNFRSF1A has Gene ID: 7132.

Thymic Stromal Lymphopoietin (TSLP) encodes a hemopoietic cytokine proposed to signal through a heterodimeric receptor complex composed of the thymic stromal lymphopoietin receptor and the IL-7R alpha chain. It mainly impacts myeloid cells and induces the release of T cell-attracting chemokines from monocytes and enhances the maturation of CD11c(+) dendritic cells. The protein promotes T helper type 2 (TH2) cell responses that are associated with immunity in various inflammatory diseases, including asthma, allergic inflammation and chronic obstructive pulmonary disease. In some instances, TSLP has Gene ID: 85480.

C-C Motif Chemokine Ligand 17 (CCL17), also known as Small-Inducible Cytokine A17, TARC, or ABCD-2, is one of several Cys-Cys (CC) cytokine genes clustered on the q arm of chromosome 16. The CC cytokines are proteins characterized by two adjacent cysteines. The cytokine encoded by this gene displays chemotactic activity for T lymphocytes, but not monocytes or granulocytes. The product of this gene binds to chemokine receptors CCR4 and CCR8. This chemokine plays important roles in T cell development in thymus as well as in trafficking and activation of mature T cells. In some instances, TSLP has Gene ID: 85480.

C-C Motif Chemokine Ligand 18 (CCL18), also known as SCYA18, CD-CK1, or AMAC1, is one of several Cys-Cys (CC) cytokine genes clustered on the q arm of chromosome 17. The CC cytokines are proteins characterized by two adjacent cysteines. The cytokine encoded by this gene displays chemotactic activity for naive T cells, CD4+ and CD8+ T cells and nonactivated lymphocytes, but not for monocytes or granulocytes. This chemokine attracts naive T lymphocytes toward dendritic cells and activated macrophages in lymph nodes. In some instances, CCL18 has Gene ID: 6362.

C-C Motif Chemokine Ligand 19 (CCL19), also known as CK Beta-11, Exodus-3, or MIP3B, is one of several CC cytokine genes clustered on the p-arm of chromosome 9. The CC cytokines are proteins characterized by two adjacent cysteines. The cytokine encoded by this gene may play a role in normal lymphocyte recirculation and homing. It also plays an important role in trafficking of T cells in thymus, and in T cell and B cell migration to secondary lymphoid organs. It specifically binds to chemokine receptor CCR7. In some instances, CCL19 has Gene ID: 6363.

C-C Motif Chemokine Ligand (CCL26), also known as Macrophage Inflammatory Protein 4-Alpha, Eotaxin-3, or SCYA26, is one of two Cys-Cys (CC) cytokine genes clustered on the q arm of chromosome 7. The CC cytokines are proteins characterized by two adjacent cysteines. The cytokine encoded by this gene displays chemotactic activity for normal peripheral blood eosinophils and basophils. The product of this gene is one of three related chemokines that specifically activate chemokine receptor CCR3. This chemokine may contribute to the eosinophil accumulation in atopic diseases. In some instances, CCL26 has Gene ID: 10344.

C-C Motif Chemokine Ligand (CCL27), also known as Skinkine, IL-11, Ralpha-Locus Chemokine, or CTACK, is one of several CC cytokine genes clustered on the p-arm of chromosome 9. The CC cytokines are proteins characterized by two adjacent cysteines. The protein encoded by this gene is chemotactic for skin-associated memory T lymphocytes. This cytokine may also play a role in mediating homing of lymphocytes to cutaneous sites. It specifically binds to chemokine receptor 10 (CCR10). Studies of a similar murine protein indicate that these protein-receptor interactions have a pivotal role in T cell-mediated skin inflammation. In some instances, CCL27 has Gene ID: 10850.

C-X-C Motif Chemokine Ligand 10 (CXCL10), also known as Gamma IP10, SCYB10, or Crg-2, encodes a chemokine of the CXC subfamily and ligand for the receptor CXCR3. Binding of this protein to CXCR3 results in pleiotropic effects, including stimulation of monocytes, natural killer and T-cell migration, and modulation of adhesion molecule expression. In some instances, CXCL10 has Gene ID: 3627.

C-X-C Motif Chemokine Ligand 11 (CXCL11), also known as Beta-R1, SCYB11, or ITAC, is a CXC member of the chemokine superfamily. Its encoded protein induces a chemotactic response in activated T-cells and is the dominant ligand for CXC receptor-3. IFN-gamma is a potent inducer of transcription of this gene. In some instances, CXCL11 has Gene ID: 6373.

C-X-C Motif Chemokine Ligand 9 (CXCL9), also known as Small-Inducible Cytokine B9, SCYB9, Crg-10, or HuMIG, encodes a protein thought to be involved in T cell trafficking. The encoded protein binds to C-X-C motif chemokine 3 and is a chemoattractant for lymphocytes but not for neutrophils. In some instances, CXCL9 has Gene ID: 4283.

Interleukin 13 (IL-13) encodes an immunoregulatory cytokine produced primarily by activated Th2 cells. This cytokine is involved in several stages of B-cell maturation and differentiation. It up-regulates CD23 and MHC class II expression, and promotes IgE isotype switching of B cells. This cytokine down-regulates macrophage activity, thereby inhibits the production of pro-inflammatory cytokines and chemokines. This cytokine is found to be critical to the pathogenesis of allergen-induced asthma but operates through mechanisms independent of IgE and eosinophils. This gene, IL3, IL5, IL4, and CSF2 form a cytokine gene cluster on chromosome 5q, with this gene particularly close to IL4. In some instances, IL-13 has Gene ID: 3596.

Interleukin 13 Receptor (IL-13R) is a type I cytokine receptor, binding Interleukin-13. It consists of two subunits, encoded by IL13RA1 and IL4R, respectively. These two genes encode the proteins IL-13Rα1 and IL-4Rα. These form a dimer with IL-13 binding to the IL-13Rα1 chain and IL-4Rα stabilises this interaction.

Interleukin 4 (IL-4), also known as Lymphocyte Stimulatory Factor 1, BCGF-1, or BSF1, encodes a protein that is a pleiotropic cytokine produced by activated T cells. This cytokine is a ligand for interleukin 4 receptor. The interleukin 4 receptor also binds to IL13, which may contribute to many overlapping functions of this cytokine and IL13. STAT6, a signal transducer and activator of transcription, has been shown to play a central role in mediating the immune regulatory signal of this cytokine. This gene, IL3, IL5, IL13, and CSF2 form a cytokine gene cluster on chromosome 5q, with this gene particularly close to IL13. This gene, IL13 and IL5 are found to be regulated coordinately by several long-range regulatory elements in an over 120 kilobase range on the chromosome. In some instances, IL-4 has Gene ID: 3565.

Nitric Oxide Synthetase 2 (NOS2), also known as Inducible NOS2 or Hepatocyte NOS, encodes a nitric oxide synthase which is expressed in liver and is inducible by a combination of lipopolysaccharide and certain cytokines. In some instances, NOS2 has Gene ID: 4843.

S100 Calcium Binding Protein A8 (S100A8), also known as Leukocyte L1 Complex Light Chain, Cystic Fibrosis Antigen, or Calgranulin A, encodes a protein that is a member of the S100 family of proteins containing 2 EF-hand calcium-binding motifs. This protein may function in the inhibition of casein kinase and as a cytokine. Altered expression of this protein is associated with the disease cystic fibrosis. In some instances, S100A8 has Gene ID: 6279.

Adenosine Deaminase, RNA Specific (ADAR), also known as Interferon-Inducible Protein 4, K88DSRBP, or P136, encodes the enzyme responsible for RNA editing by site-specific deamination of adenosines. This enzyme destabilizes double-stranded RNA through conversion of adenosine to inosine. Mutations in this gene have been associated with dyschromatosis symmetrica hereditaria. In some instances, ADAR has Gene ID: 103.

Autophagy Related 5 (ATG5), also known as Apoptosis-Specific Protein, APG5L, or HAPG5, encodes a protein that, in combination with autophagy protein 12, functions as an E1-like activating enzyme in a ubiquitin-like conjugating system. The encoded protein is involved in several cellular processes, including autophagic vesicle formation, mitochondrial quality control after oxidative damage, negative regulation of the innate antiviral immune response, lymphocyte development and proliferation, MHC II antigen presentation, adipocyte differentiation, and apoptosis. In some instances, ATG5 has Gene ID: 9474.

C-C Motif Chemokine Ligand 5 (CCL5), also known as SIS-Delta, Eosinophil Cheomtactic Cytokine, or TCP228, is one of several chemokine genes clustered on the q-arm of chromosome 17. This chemokine, a member of the CC subfamily, functions as a chemoattractant for blood monocytes, memory T helper cells and eosinophils. It causes the release of histamine from basophils and activates eosinophils. This cytokine is one of the major HIV-suppressive factors produced by CD8+ cells. It functions as one of the natural ligands for the chemokine receptor chemokine (C-C motif) receptor 5 (CCR5), and it suppresses in vitro replication of the R5 strains of HIV-1, which use CCR5 as a coreceptor. In some instances, CCL5 has Gene ID: 6352.

The interferon-inducible p200 family of proteins (IFI's) are gene products induced by interferons (IFNs). Proteins in this family share significant homology, with human homologues comprising IFI-16, myeloid cell nuclear differentiation antigen (MNDA) and absent in melanoma (AIM) 2. The p200 proteins have been implicated in cell cycle regulation and differentiation based on their ability to interact with and modulate the activities of multiple transcriptional factors such as Rb and p53

Interferon Induced proteins with Tetratricopeptide repeats (IFIT's) confer immunity against viral infection. These proteins are generally produced during viral infection, Interferon (IFN) treatment, and during pathogen recognition (Pathogen associated molecular pattern recognition) by the immune system during infections.

Interferon Alpha 1 (IFNA1), also known as Interferon Alpha-D, IFNA13, or LeIFD, encodes a protein that is produced by macrophages and has antiviral activity. In some instances, IFNA1 has Gene ID: 3439.

Interferon Alpha 2 (IFNA2), also known as Alpha-2a Interferon, IFN2B, or IFNA2C, is a member of the alpha interferon gene cluster on chromosome 9. The encoded protein is a cytokine produced in response to viral infection. Use of the recombinant form of this protein has been shown to be effective in reducing the symptoms and duration of the common cold. In some instances, IFNA2 has Gene ID: 3440.

Interferon Alpha 4 (IFNA4), also known as Interferon Alpha-4B, Interferon Alpha-M1 or Interferon Alpha-76, is a Protein Coding gene. Diseases associated with IFNA4 include Rabies. Among its related pathways are RIG-I/MDA5 mediated induction of IFN-alpha/beta pathways and Cytokine Signaling in Immune system. In some instances, IFNA4 has Gene ID: 3441.

Interferon Alpha And Beta Receptor Subunit 1 (IFNAR1), also known as Cytokine Receptor Class-II Member 1, IFN-R-1, or AVP, encodes a protein that is a type I membrane protein that forms one of the two chains of a receptor for interferons alpha and beta. Binding and activation of the receptor stimulates Janus protein kinases, which in turn phosphorylate several proteins, including STAT1 and STAT2. The encoded protein also functions as an antiviral factor. In some instances, IFNAR1 has Gene ID: 3454.

Interferon Alpha And Beta Receptor Subunit (IFNAR2), also known as IFNABR, Interferon Alpha Binding Protein, or IMD45, encodes a protein that is a type I membrane protein that forms one of the two chains of a receptor for interferons alpha and beta. Binding and activation of the receptor stimulates Janus protein kinases, which in turn phosphorylate several proteins, including STAT1 and STAT2. In some instances, IFNAR2 has Gene ID: 3455.

Interferon Beta 1 (IFNB1), also known as Fibroblast Interferon, IFN-Beta, or IFF, encodes a cytokine that belongs to the interferon family of signaling proteins, which are released as part of the innate immune response to pathogens. The protein encoded by this gene are involved in cell differentiation and anti-tumor defenses. Following secretion in response to a pathogen, type I interferons bind a homologous receptor complex and induce transcription of genes such as those encoding inflammatory cytokines and chemokines. Overactivation of type I interferon secretion is linked to autoimmune diseases. In some instances, IFNB1 has Gene ID: 3456.

Interferon Epsilon (IFNE), also known as Interferon Tau-1 or PRO655, is a Protein Coding gene. Among its related pathways are PEDF Induced Signaling and JAK-STAT signaling pathway (KEGG). In some instances, IFNE has Gene ID: 338376.

Interferon Omega 1 (IFNW1), also known as Interferon Alpha-II-1, encodes a protein that is an interferon and possesses antiviral activity. The encoded protein binds to the interferon alpha/beta receptor but not to the interferon gamma receptor. In some instances, IFNW1 has Gene ID: 3467.

Interleukin 1 Receptor Associated Kinase 1 (IRAK1), also known as EC2.7.11.1 or Pelle, encodes the interleukin-1 receptor-associated kinase 1, one of two putative serine/threonine kinases that become associated with the interleukin-1 receptor (IL1R) upon stimulation. This gene is partially responsible for IL1-induced upregulation of the transcription factor NF-kappa B. In some instances, IRAK1 has Gene ID: 3654.

Interferon Regulatory Factors (IRF's) are proteins which regulate transcription of interferons. They are used in the JAK-STAT signaling pathway. Expression of IRF genes is under epigenetic regulation by promoter DNA methylation.

Keratins (KRT's) are a family of fibrous structural proteins making up hair, nails, horns, claws, hooves, and the outer layer of human skin. Keratin is also the protein that protects epithelial cells from damage or stress.

2'-5'-Oligoadenylate Synthetase 1 (OAS1), also known as E18/E16, OIAS, or P46/P42 OAS, is induced by interferons and encodes a protein that synthesizes 2',5'-oligoadenylates (2-5As). This protein activates latent RNase L, which results in viral RNA degradation and the inhibition of viral replication.

Osteopontin (OPN), also known as bone sialoprotein I (BSP-1 or BNSP), early T-lymphocyte activation (ETA-1), secreted phosphoprotein 1 (SPP1), 2ar and *Rickettsia* resistance (Ric), is a protein that in humans is encoded by the SPP1 gene (secreted phosphoprotein 1). In some instances, SPP1 has Gene ID: 6696.

Signal Transducer And Activator Of Transcription 4 (STAT4), also known as SLEB11, encodes a protein that is a member of the STAT family of transcription factors. In response to cytokines and growth factors, STAT family members are phosphorylated by the receptor associated kinases, and then form homo- or heterodimers that translocate to the cell nucleus where they act as transcription activators. This protein is essential for mediating responses to IL12 in lymphocytes, and regulating the differentiation of T helper cells. Mutations in this gene may be associated with systemic lupus erythematosus and rheumatoid arthritis. In some instances, STAT4 has Gene ID: 6775.

TNF Alpha Induced Protein 3 (TNFAIP3), also known as Putative DNA-Binding Protein A20, Zinc Finger Protein A20, or OTUD7C, is a gene whose expression is rapidly induced by the tumor necrosis factor (TNF). The protein encoded by this gene is a zinc finger protein and ubiqitin-editing enzyme, and has been shown to inhibit NF-kappa B activation as well as TNF-mediated apoptosis. The encoded protein, which has both ubiquitin ligase and deubiquitinase activities, is involved in the cytokine-mediated immune and inflammatory responses. In some instances, TNFAIP3 has Gene ID: 7128.

Tyrosine Kinase 2 (TYK2), also known as Non-Receptor Tyrosine-Protein Kinase TYK2, EC 2.7.10.2, or IMD35, encodes a member of the tyrosine kinase and, more specifically, the Janus kinases (JAKs) protein families. This protein associates with the cytoplasmic domain of type I and type II cytokine receptors and promulgate cytokine signals by phosphorylating receptor subunits. It is also component of both the type I and type III interferon signaling pathways. As such, it may play a role in anti-viral immunity. In some instances, TYK2 has Gene ID: 7297.

EXAMPLES

These examples are provided for illustrative purposes only and not to limit the scope of the claims provided herein.

Example 1—Non-Invasive Gene Expression Analysis for Psoriasis

Figure 6:
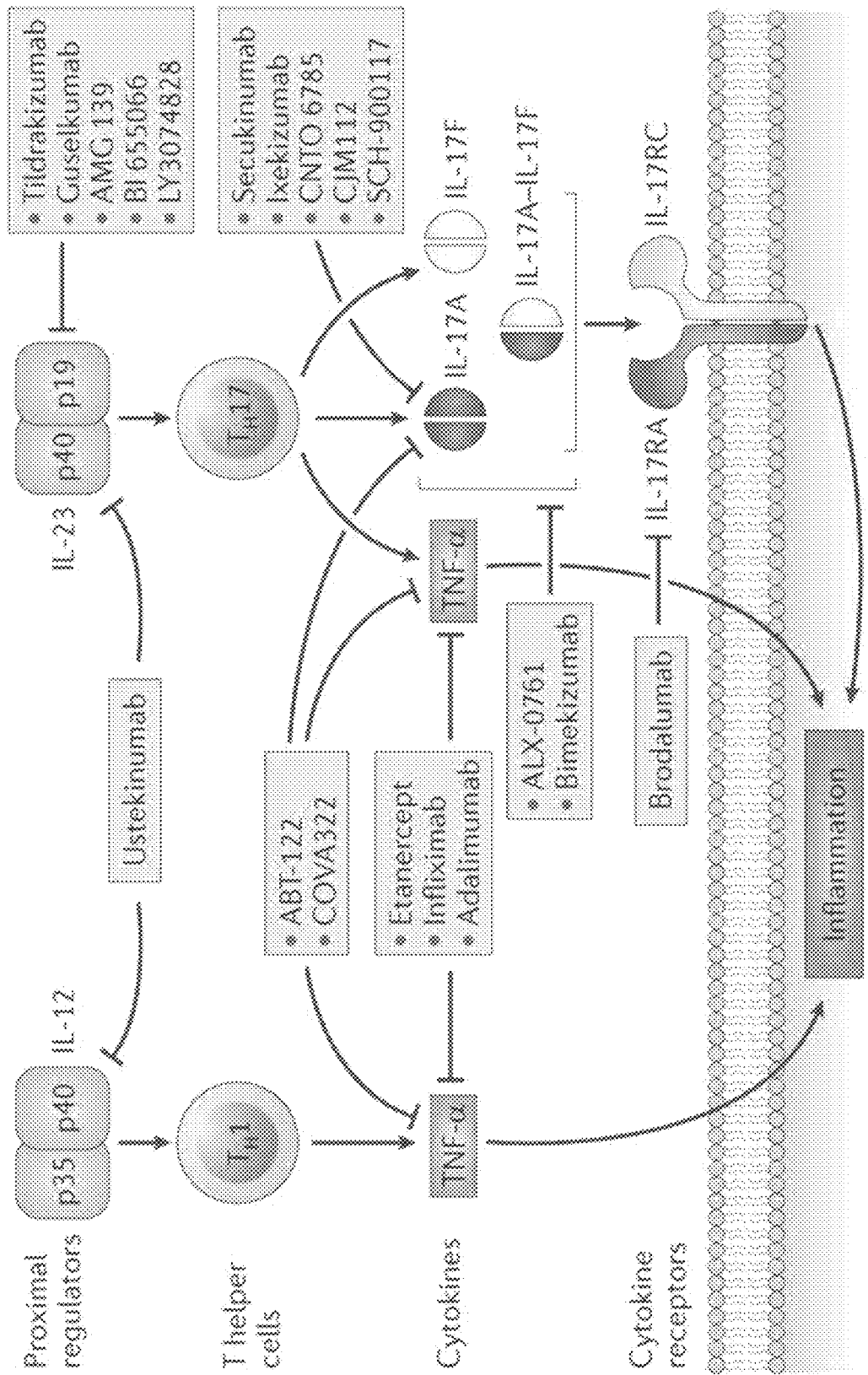
FIG. 6 shows a number of drugs that target the IL-17/TH-17 pathway and where they effect the inflammation cycle.

Progress has been made in the treatment of moderate to severe psoriasis by blocking TNF alpha, IL-17A and IL-23. The pathways affected are depicted in FIG. 6. Further, disease monitoring, prediction of flare-ups and treatment selection remain challenging. Described below is a non-invasive method to assess gene expression in psoriasis and to predict treatment response.

Samples were assayed using the adhesive patch-based skin biopsy platform described herein. The modular structure of the qRT-PCR assay allowed it to be employed in a number of inflammatory skin conditions including psoriasis, atopic dermatitis, or lupus. In psoriasis, the assay focused on 20 targets involved in expanded TH17 pathways.

Over 500 lesional and non-lesional adhesive patch biopsy samples from patients with moderate to severe psoriasis demonstrated detection of 20 selected targets by qRT-PCR and differences in gene expression signatures of lesional, non-lesional, and non-psoriasis control skin ($p<0.001$, n=24). Analyses from non-lesional samples avoided the need to control for disease activity in individual psoriasis lesions and provide clinically useful information. In non-lesional psoriatic sample compared to normal skin, gene expression levels of IL-17A, IL-17C, IL-17F, IL-17 receptors, IL-23A, IL-22, IL-24, IL-6, IL-8, CXCL1, CXCL5, DEFB4A, LCN2, S100A7 as well as TNF-α and its receptor were altered by 2 to 200 fold. Therapeutic intervention with targeted therapeutics such as ixekizumab ($p<0.001$) reduced target gene expression (including IL-17A and 17F, TNF-α and CXCL1 and CXCL5) compared to baseline after 2 weeks.

Results indicate non-invasive gene expression analysis of lesional and non-lesional epidermal skin samples is a method to monitor disease activity with the potential to predict flare-ups and treatment failure in psoriasis.

Example 2—Non-Invasive Gene Expression Analysis for Psoriasis Utilizing a Different Test Population An adhesive patch-based device as described herein was used to collect epidermal skin cells from test subjects (healthy persons as control and treatment naïve psoriatic patients) through a non-invasive procedure (from psoriatic patients, both lesional and non-lesional skins were also collected). Total RNA was extracted from these samples and used for cytokine gene expression analysis with TaqMan RT-qPCR. A panel of 13 cytokines, mainly in the Th17 pathway, involved in psoriasis was studied and their expression levels were calculated through the threshold cycle count (Ct) from the qPCR.

Figure 28A:
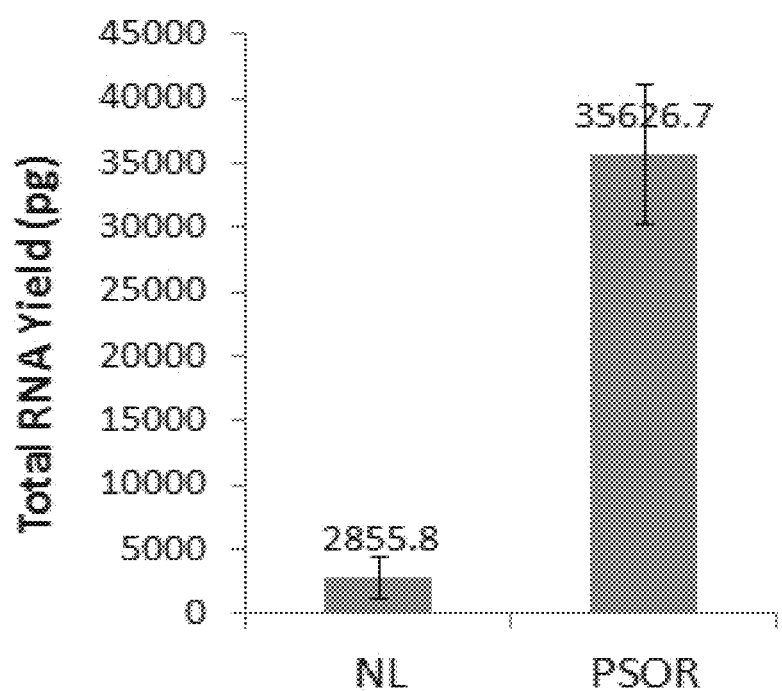
FIG. 28A shows total RNA yields (pg) from lesional (PSOR) and non-lesional (NL) skin in psoriatic patients.
Figure 28B:
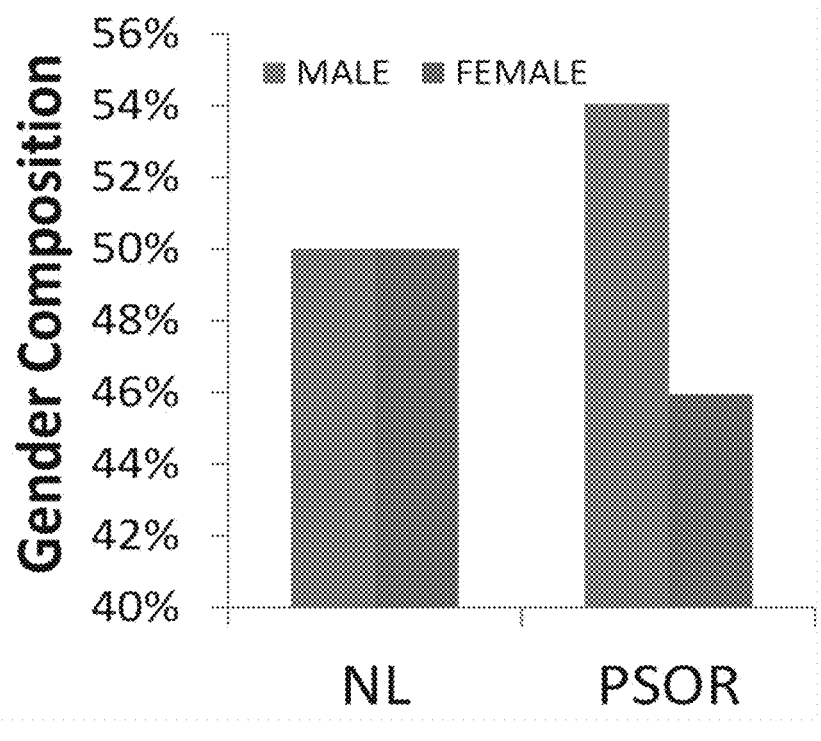
FIG. 28B shows gender composition of nonlesional and psoriatic groups.
Figure 28C:
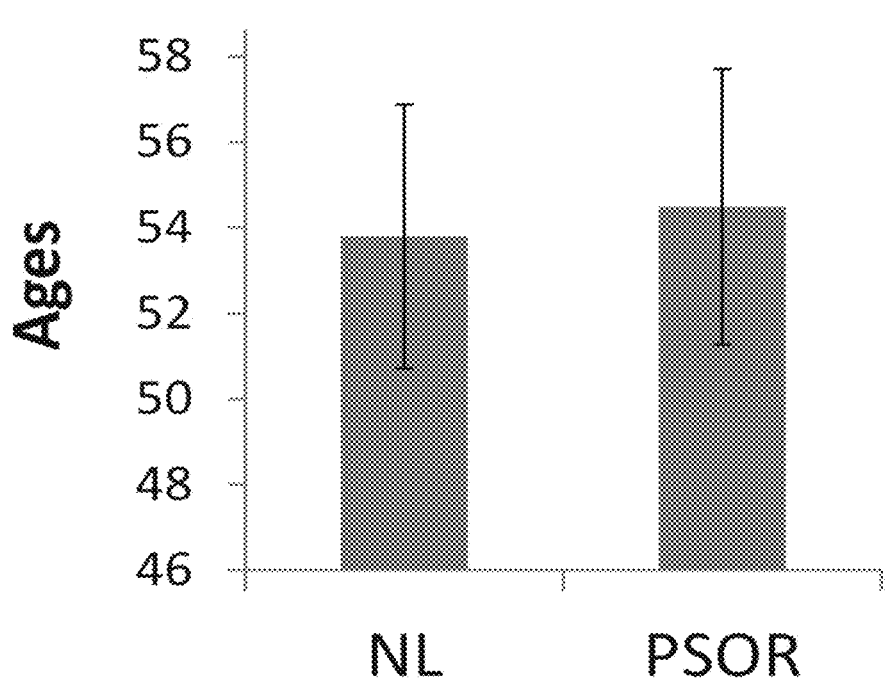
FIG. 28C shows age distribution of nonlesional and psoriatic groups.
Figure 29A:
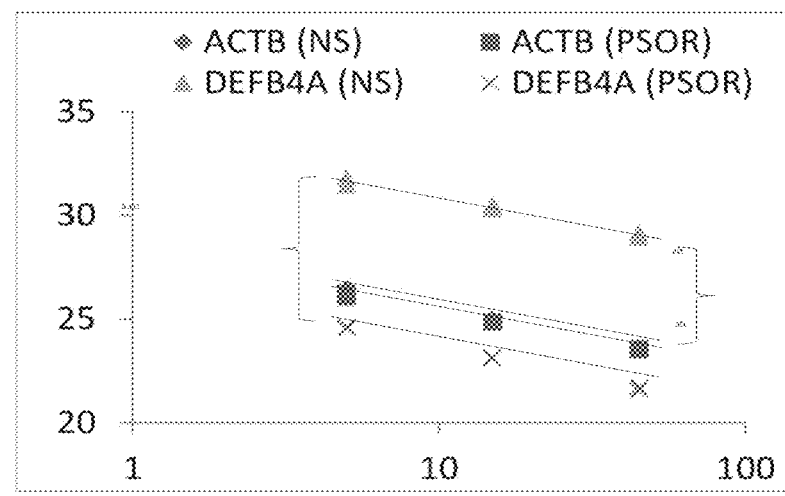
FIG. 29A shows measurement of ACTB and DEFB4A expression in lesional (PSOR) and normal skins (NS) at different RNA input levels.
Figure 29B:
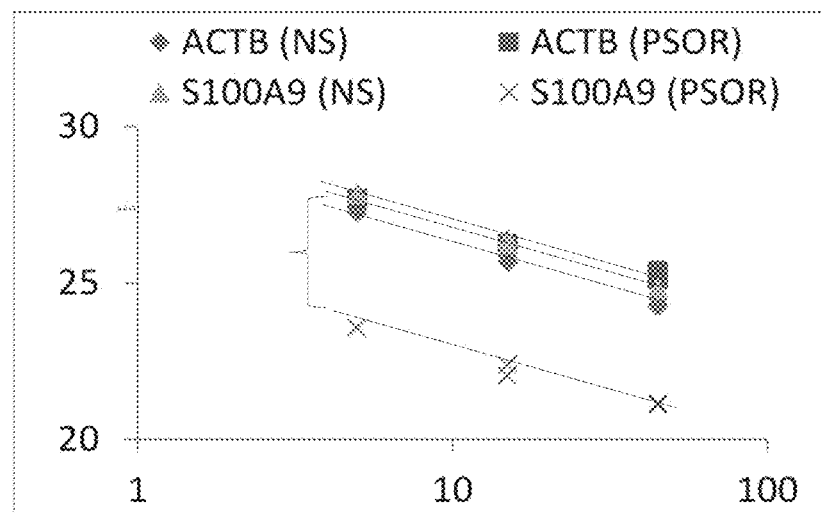
FIG. 29B shows measurement of ACTB and S100A9 expression in lesional (PSOR) and normal skins (NS) at different RNA input levels.
Figure 29C:
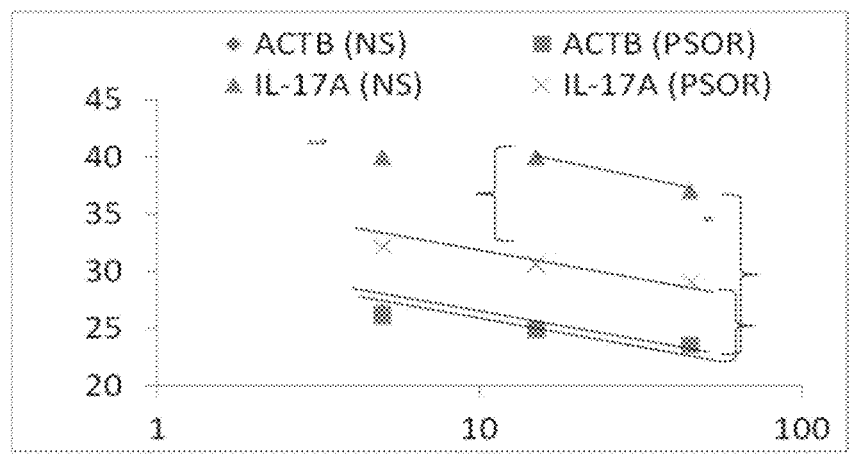
FIG. 29C shows measurement of ACTB and IL-17A expression in lesional (PSOR) and normal skins (NS) at different RNA input levels.
Figure 29D:
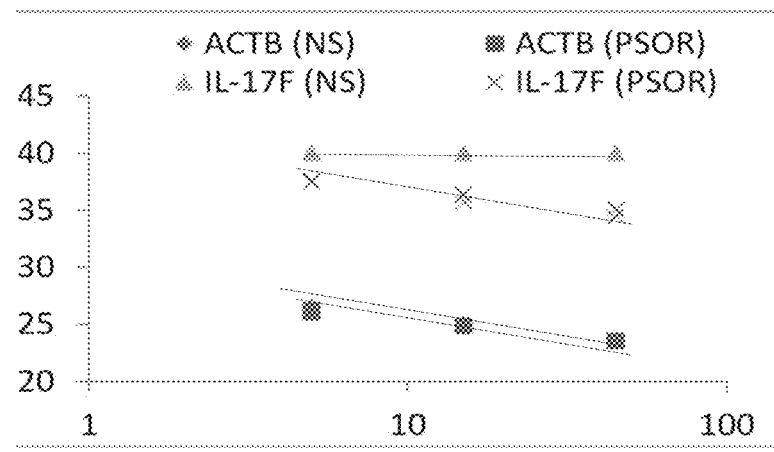
FIG. 29D shows measurement of ACTB and IL-17F expression in lesional (PSOR) and normal skins (NS) at different RNA input levels.
Figure 29E:
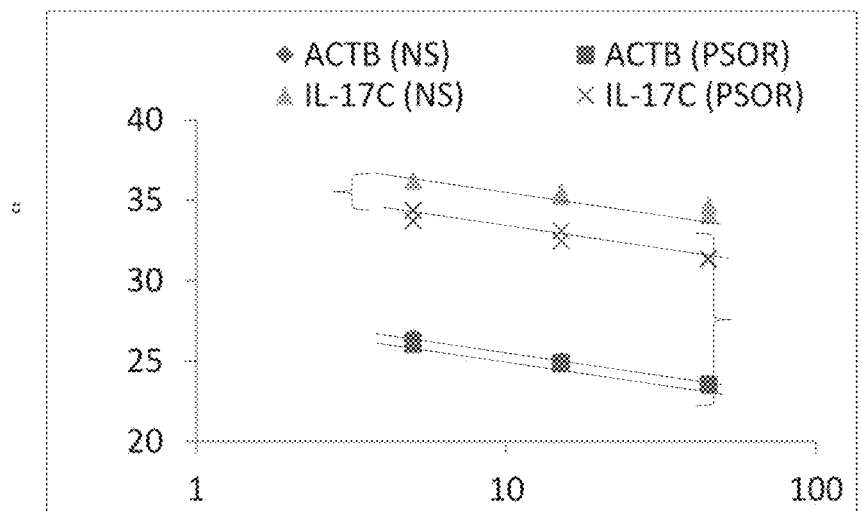
FIG. 29E shows measurement of ACTB and IL-17C expression in lesional (PSOR) and normal skins (NS) at different RNA input levels.
Figure 29F:
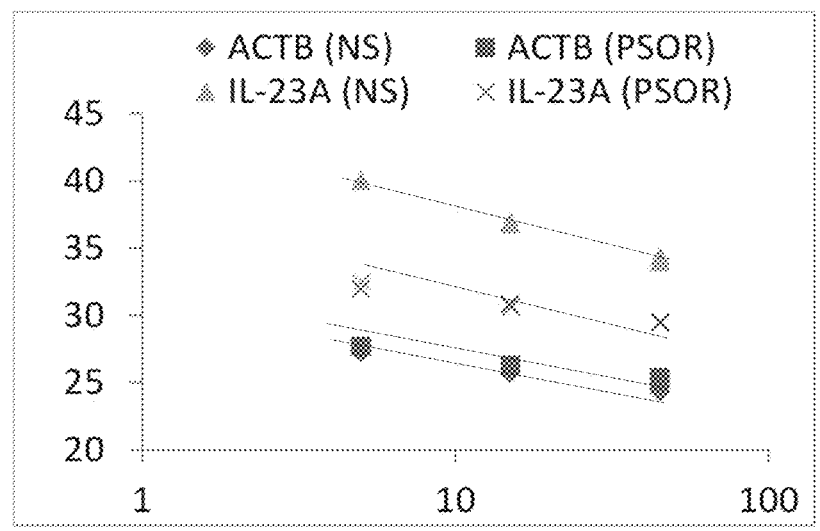
FIG. 29F shows measurement of ACTB and IL-23A expression in lesional (PSOR) and normal skins (NS) at different RNA input levels.

With the adhesive patch-based device, epidermal tissues were collected from all test subjects and total RNA was isolated (FIGS. 28A-28C). As psoriatic lesion often had a thickened skin with dried flaky layers of tissues, adhesive patch sampling often yielded more skin tissues thus higher RNA yields from psoriatic lesional skins than that from normal or non-lesional skins.

Testing of isolated RNA by qPCR allowed for detection of gene expression changes. FIGS. 29A-29F show tests on several key genes (IL-17, IL-23, DEFB4 and S100A9) and compares their expression levels in both PSOR and NS (normal skin) with dilutions of RNA inputs in qPCR. Elevated gene expressions (shown as a downward shift of Ct value) are seen in PSOR skins for most targets, while a linear parallel changes in Ct in both target gene and housekeeping gene ACTB with changing RNA input in qPCR confirms both the quality of the isolated RNA for gene expression and accuracy of the qPCR analysis adopted to the current assay on cytokine gene expression analysis.

Figure 30:
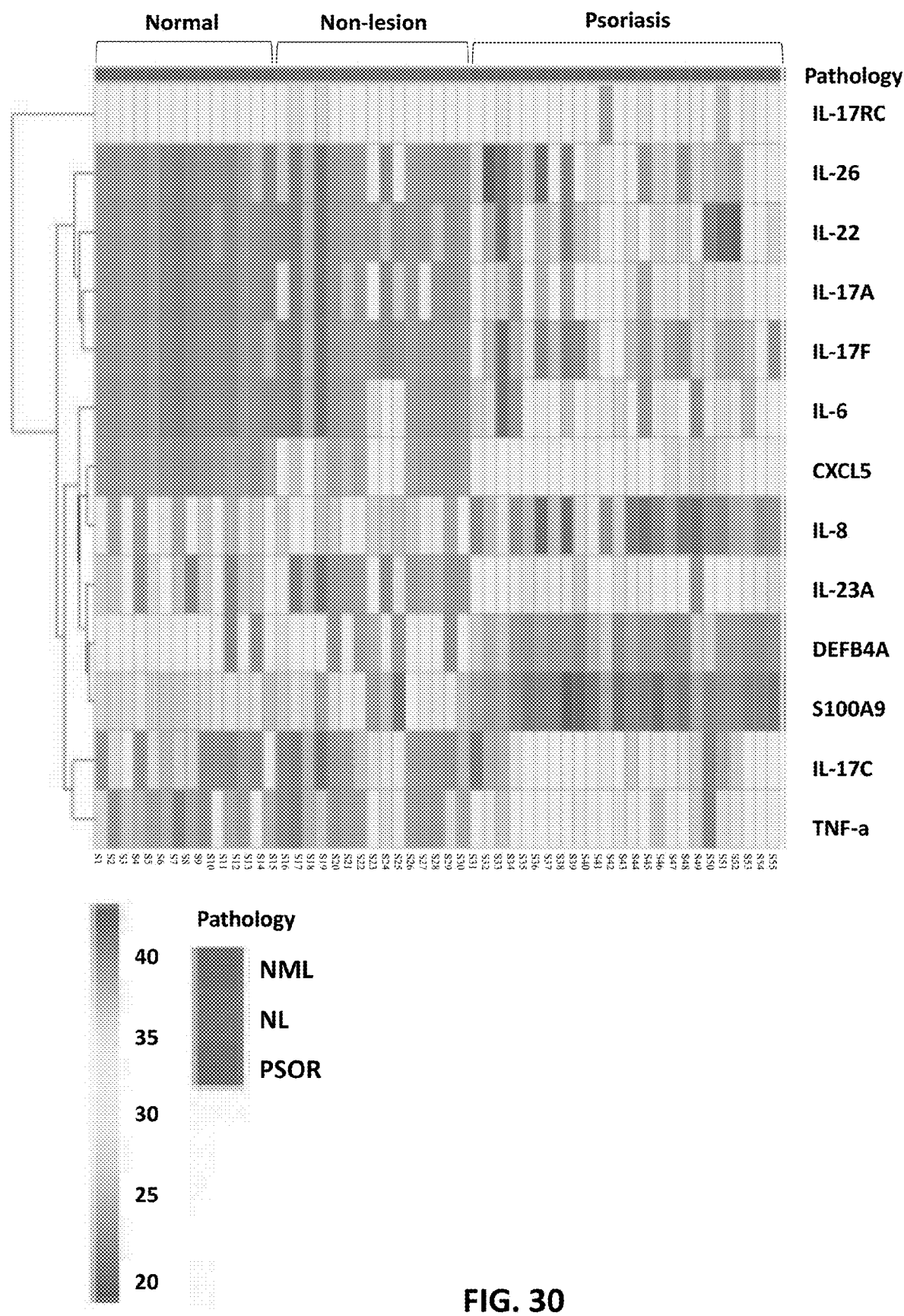
FIG. 30 shows a heatmap of Ct values of 13 key genes from normal (NML), and psoriatic lesional (PSOR) and non-lesional (NL) skin samples collected with adhesive patch-based devices.

Psoriasis is affected by many cytokines and their interactions. FIG. 30 shows a heatmap constructed from the Ct values of 13 cytokine genes from 53 RNA samples (14 NML, 15 NL and 24 PSOR skins). A darker red on the heatmap shows a lower Ct or an increased gene expression while a darker grey shows a higher Ct or a lower gene expression in the cells. The psoriatic lesional skins have demonstrated a different heatmap from that in other 2 types of skins (normal and non-lesion). The gene expression pattern within PSRO group had also displayed a high degree of uniformity, in comparison with traditional biopsy method such as liquid biopsy or surgical biopsy.

Figure 31:
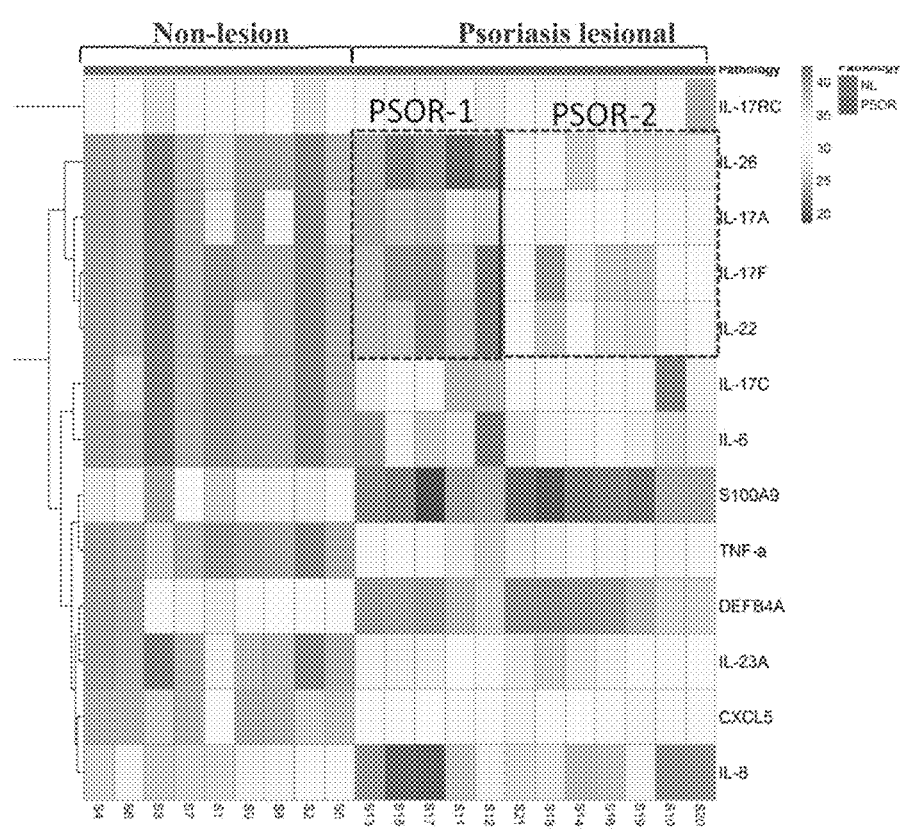
FIG. 31 shows a heatmap of Ct values of 13 genes from paired lesional (PSOR) and non-lesional (NL) skins collected from the treatment naïve psoriatic patients, with 2 distinct subgroups of gene expressions in lesional tissues (PSOR-1 and -2).

In addition, the non-invasive gene expression analysis assay had also detected subgroups of PSOR lesions, varied in the expression levels of key genes (IL-17, 22, 26) in the Th17 pathway (FIG. 31), which might associate to patients who fail to respond to drug treatment.

Figure 5:
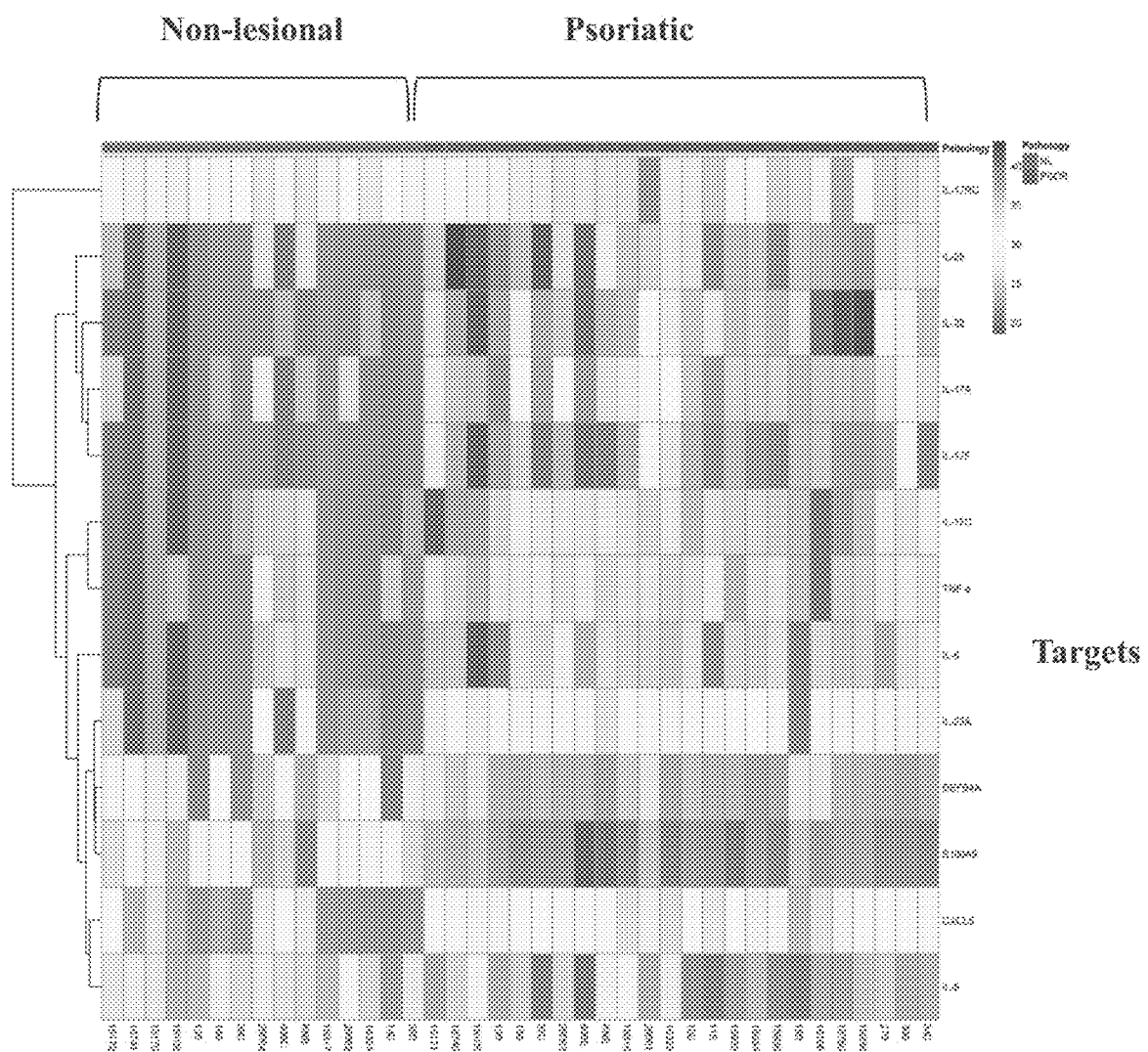
FIG. 5 shows detection of various markers of stratum corneum gene expression in psoriasis lesional and non-lesional skin.

Example 3—Stratum Corneum Gene Expression Measurements in Psoriasis Lesional and Non-Lesional Skin Samples were collected using the adhesive patch-based device described herein. Antibodies selective against cytokine targets including their receptors were assessed for expression levels in 24 psoriasis lesional and 15 non-lesional skin samples. Samples were tested for binding to IL-17RC, IL-26, IL-22, IL-17A, IL-17F, IL-17C, TNFα, IL-6, IL-23A, DEFB4A, S100A9, CXCL5, and IL-8. FIG. 5 is a heat map showing results of screening. In psoriatic samples, lower levels of antibody binding were detected to DEFB4A, S100A9, CXCL5, and IL-8. In non-psoriatic samples, increased binding to IL-17RC, IL-26, IL-22, IL-17A, IL-17F, IL-17C, TNFα, IL-6, and IL-23A was detected.

Example 4—Cytokine Transcription Levels from Adhesive Patch Samples

Two RNA samples were collected from psoriatic skin using adhesive patch collection methods described herein. Table 1 shows elevated expression levels of psoriatic cytokines from the IL-23/TH17 axis.

TABLE 1

| Sample | | IL-17A | 17RA | IL-17C | 17RC | IL-17F | TNF-a | S100A7 | S100A9 |
|---|---|---|---|---|---|---|---|---|---|
| 1 | ΔΔCt | −3.7 | 0.6 | −6.3 | 1.0 | −2.7 | −8.3 | −12.9 | −17.5 |
|   | Fc | 12.6 | 0.7 | 76.7 | 0.5 | 6.6 | 314.7 | 7781.4 | 186063.8 |
| 2 | ΔΔCt | −7.4 | −0.8 | −6.6 | 1.2 | −2.9 | −6.3 | −14.1 | −16.7 |
|   | FC | 168.9 | 1.7 | 97.2 | 0.4 | 7.2 | 81.2 | 17104.6 | 109218.3 |

| Sample | | CCL20 | IL-22 | CXCL1 | IL-24 | CXCL5 | IL-26 | LCN2 | DEFB4A |
|---|---|---|---|---|---|---|---|---|---|
| 1 | ΔΔCt | −1.9 | −7.7 | −7.0 | −0.4 | −7.9 | −2.5 | −10.2 | −17.4 |
|   | Fc | 3.7 | 208.5 | 128.6 | 1.3 | 239.0 | 5.5 | 1171.8 | 169438.3 |
| 2 | ΔΔCt | 6.0 | 0.2 | −3.1 | 0.6 | −9.7 | −6.9 | −10.2 | −18.5 |
|   | FC | 0.0 | 0.9 | 8.8 | 0.7 | 827.0 | 122.7 | 1172.4 | 368594.1 |

Figure 25:
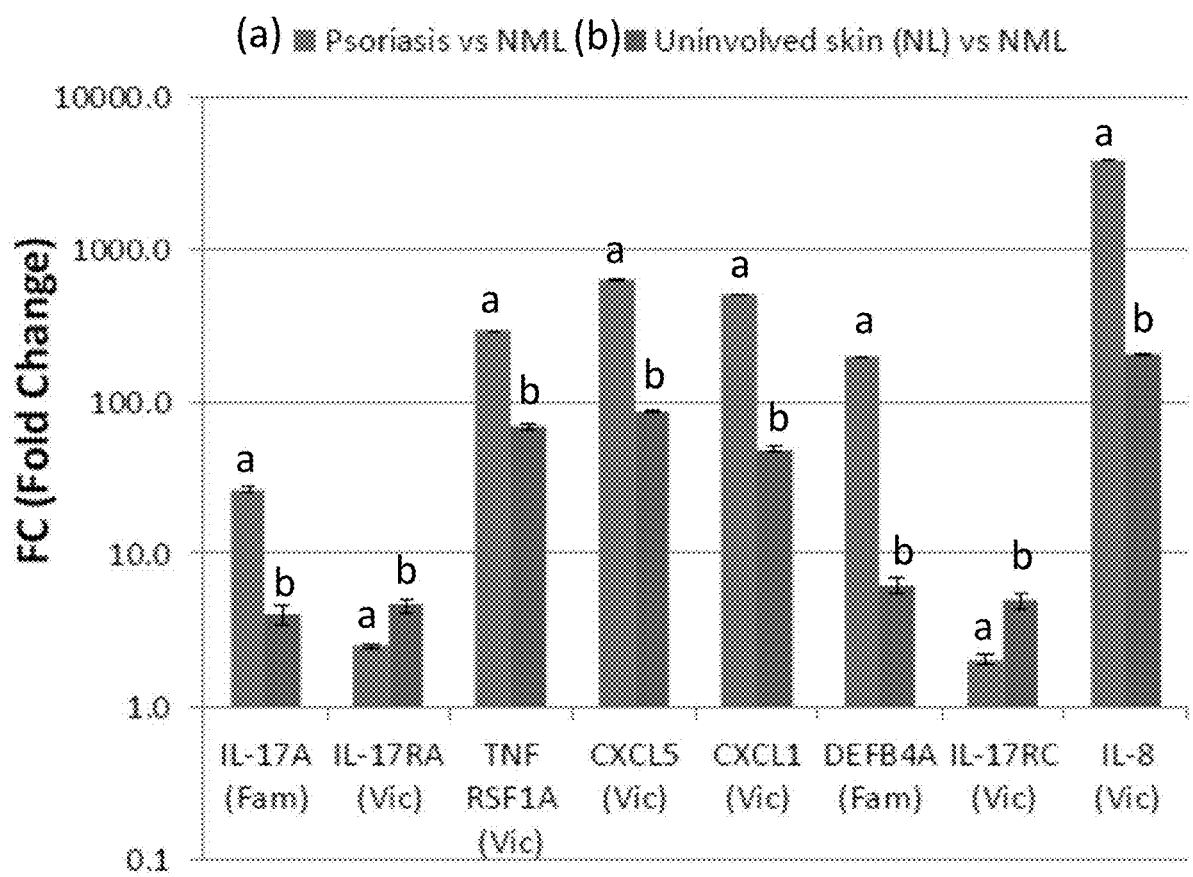
FIG. 25 shows cytokines with increased gene expression detected in both uninvolved non-lesional skin and psoriatic lesions.
Figure 26:
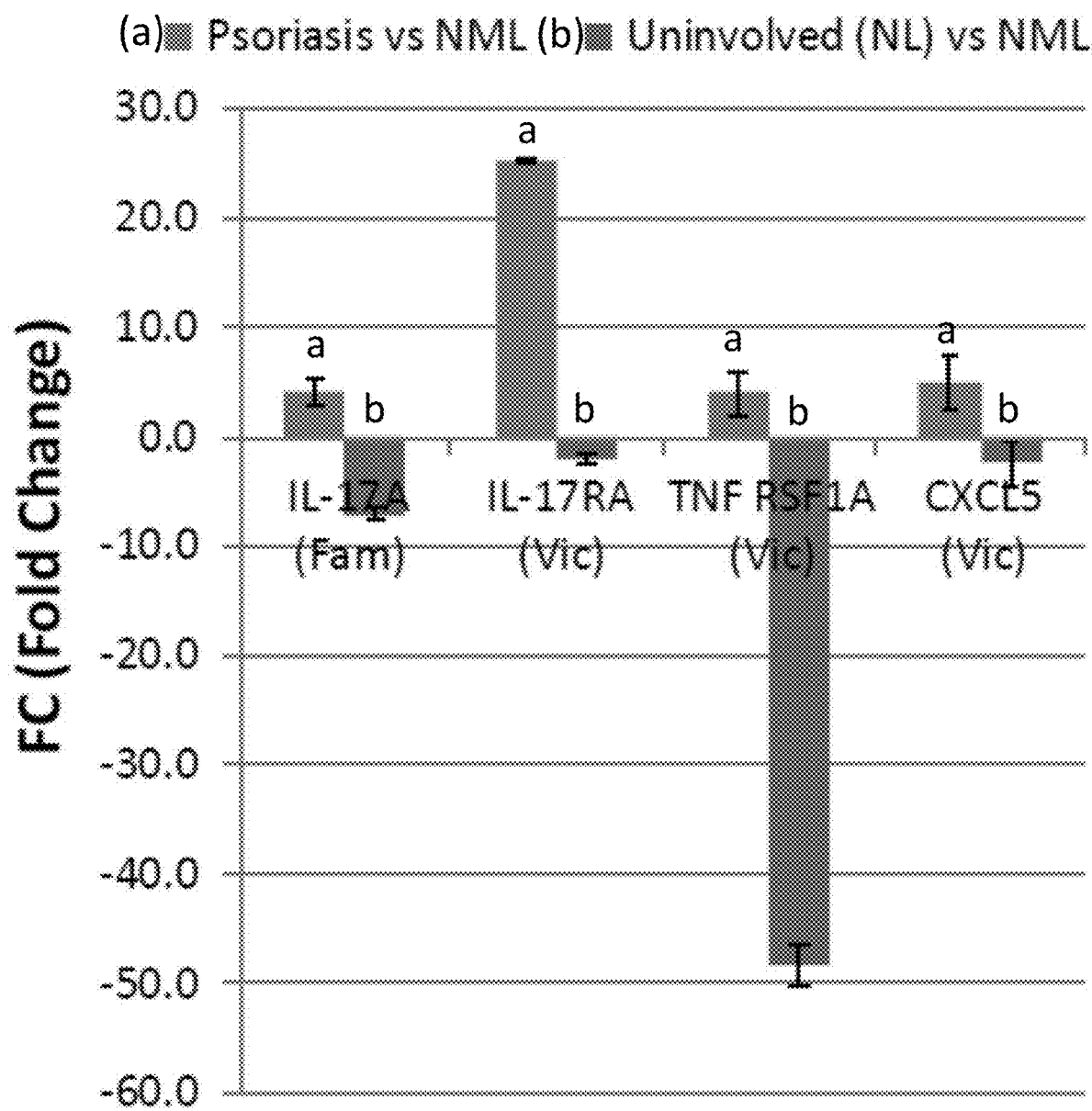
FIG. 26 shows cytokines with decreased gene expression in uninvolved non-lesional skin but increased gene expression in psoriatic lesions.
Figure 27A:
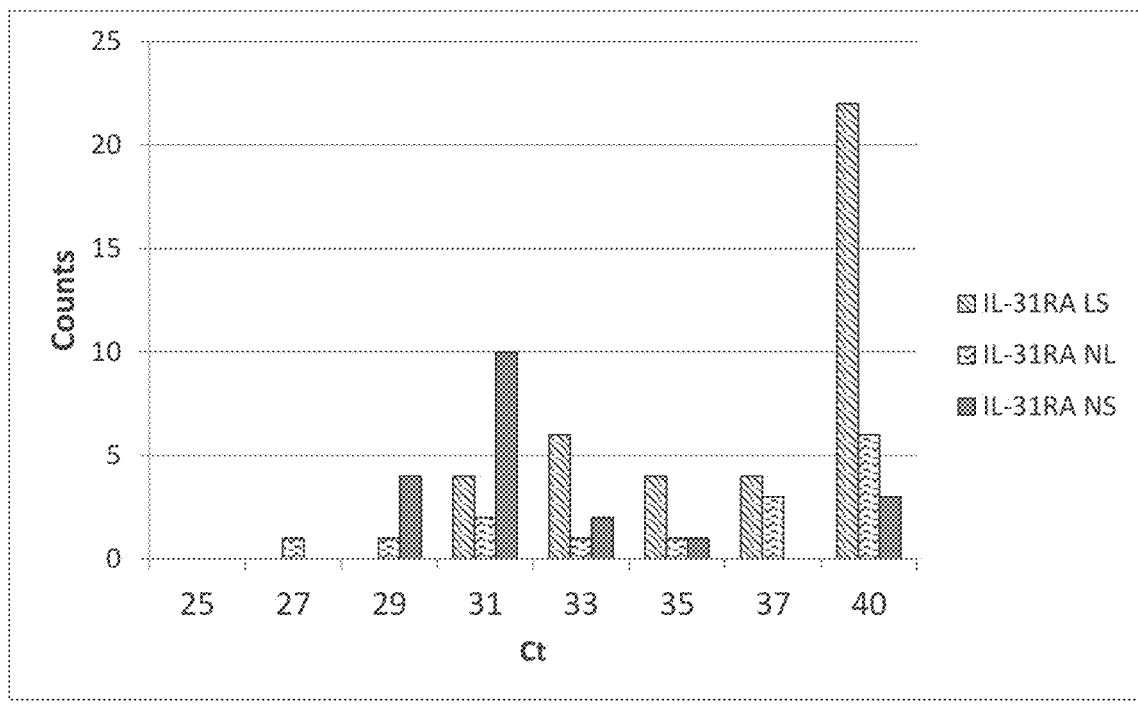
FIG. 27A shows expression of IL-31RA in AD lesion skin and non-lesion skin compared to expression of IL-31RA in normal skin.
Figure 27B:
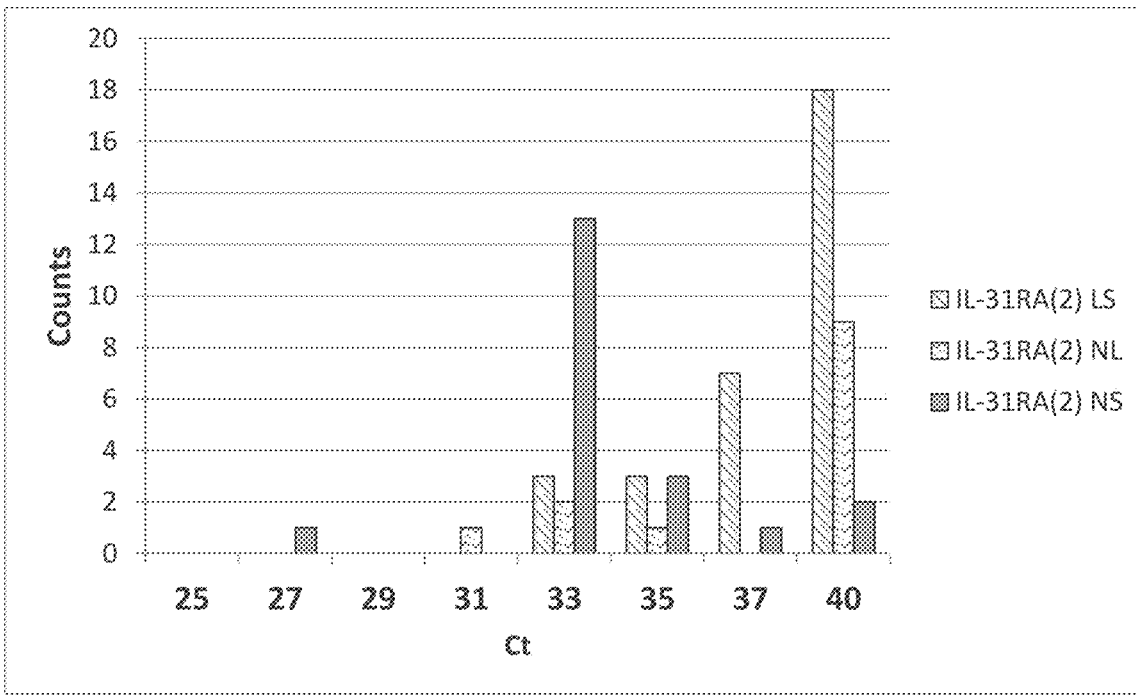
FIG. 27B shows expression of IL-31RA(2) in AD lesion skin and non-lesion skin compared to expression of IL-31RA(2) in normal skin.
Figure 27C:
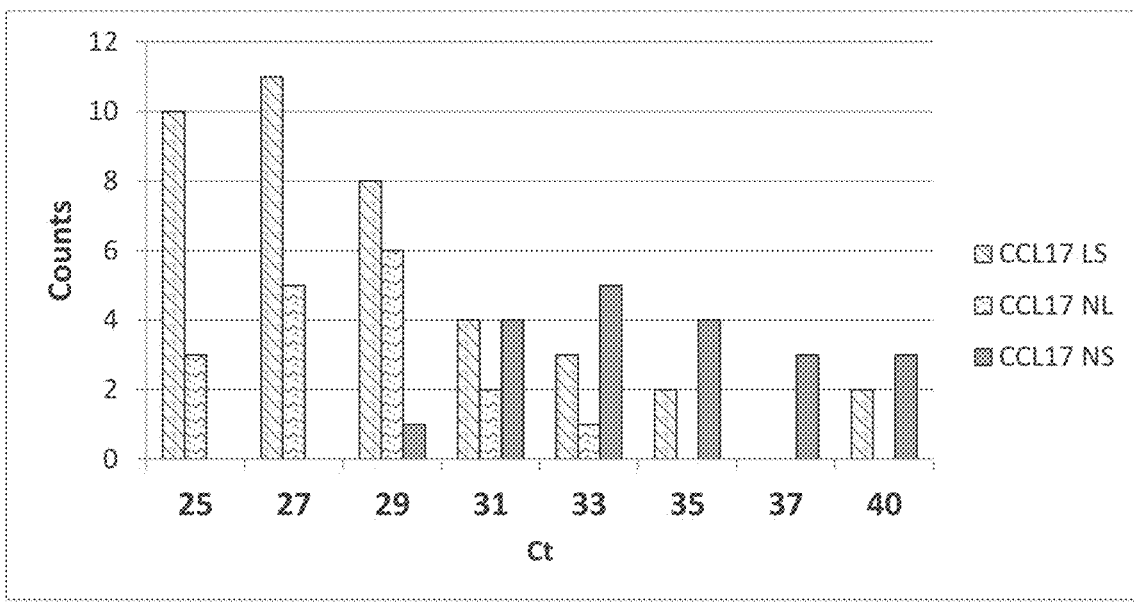
FIG. 27C shows expression of CCL17 in AD lesion skin and non-lesion skin compared to expression of CCL17 in normal skin.
Figure 27D:
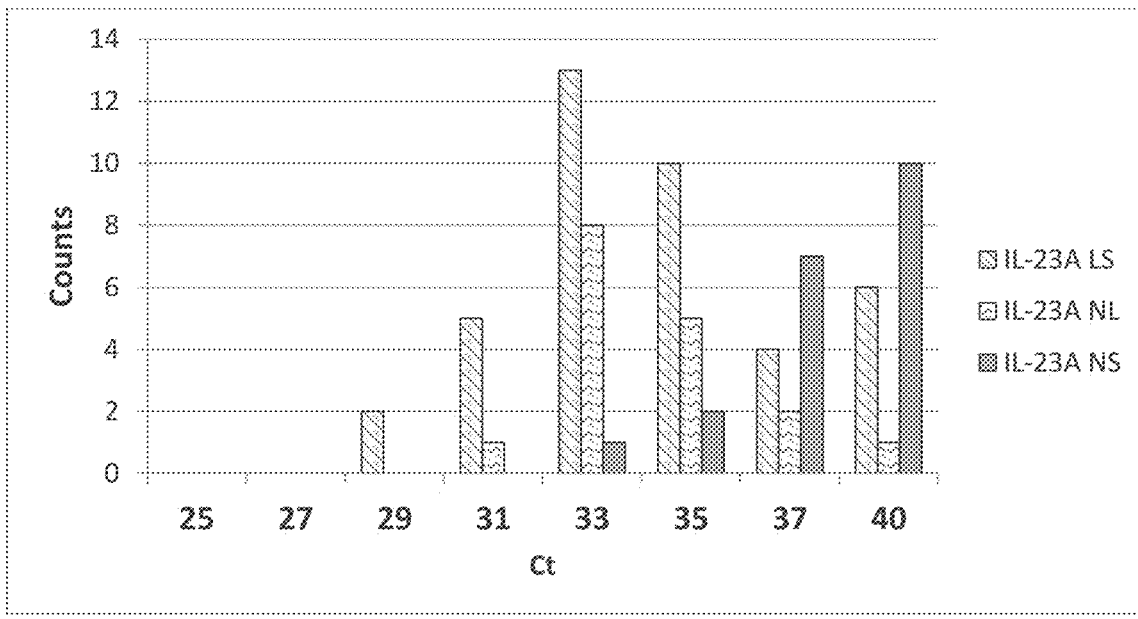
FIG. 27D shows expression of IL-23A in AD lesion skin and non-lesion skin compared to expression of IL-23A in normal skin.
Figure 27E:
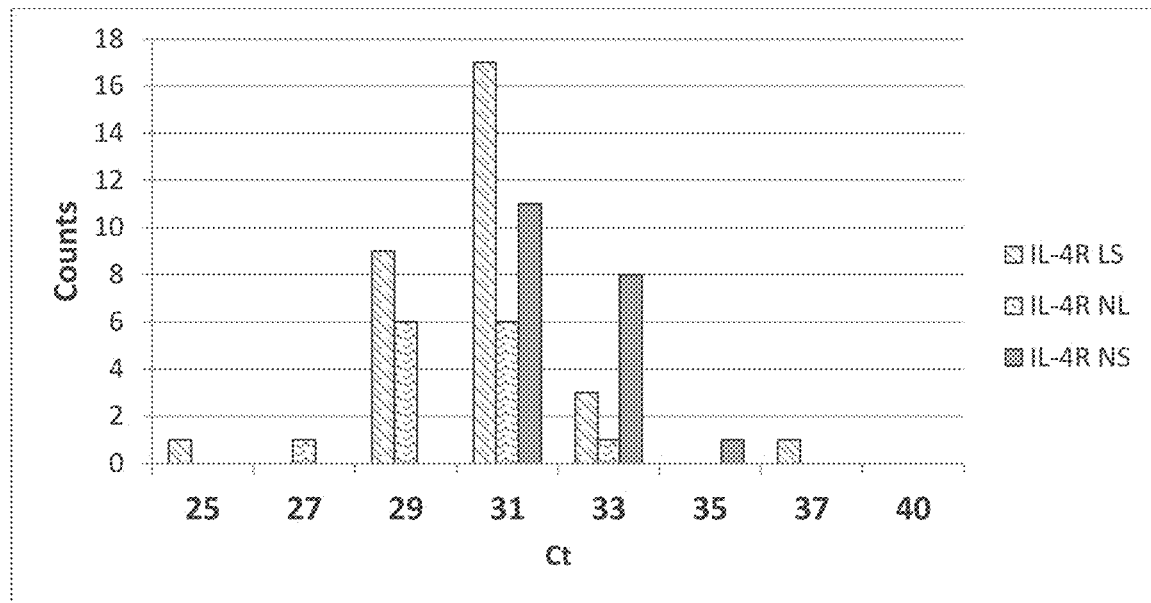
FIG. 27E shows expression of IL-4R in AD lesion skin and non-lesion skin compared to expression of IL-4R in normal skin.
Figure 27F:
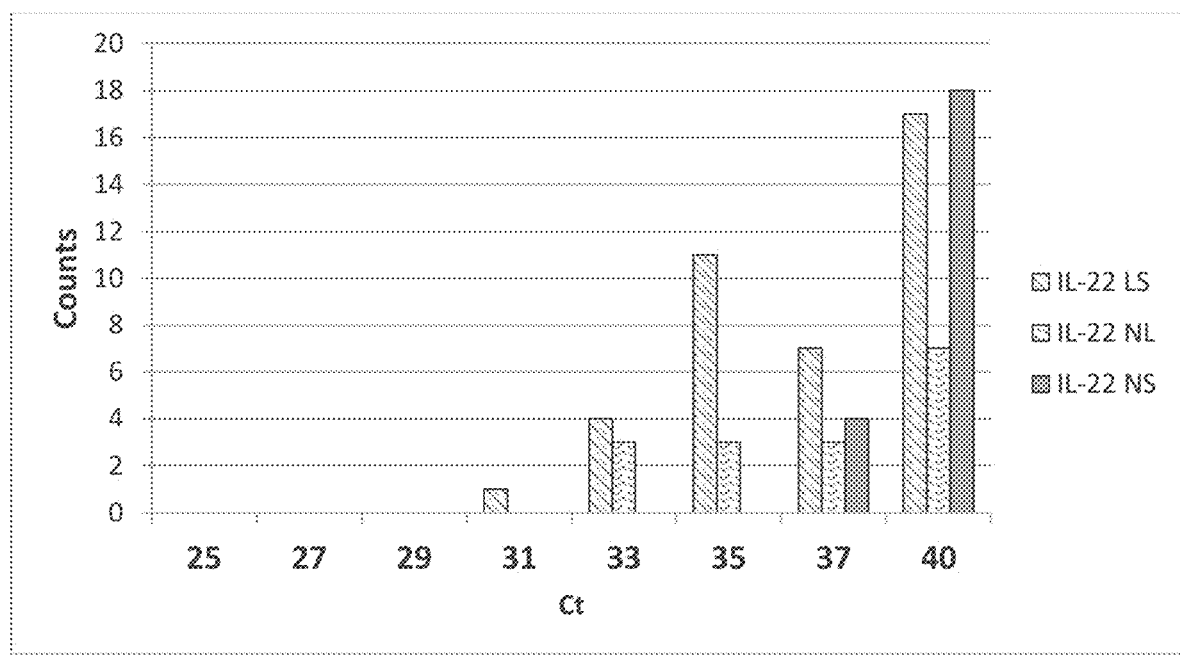
FIG. 27F shows expression of IL-22 in AD lesion skin and non-lesion skin compared to expression of IL-22 in normal skin.
Figure 27G:
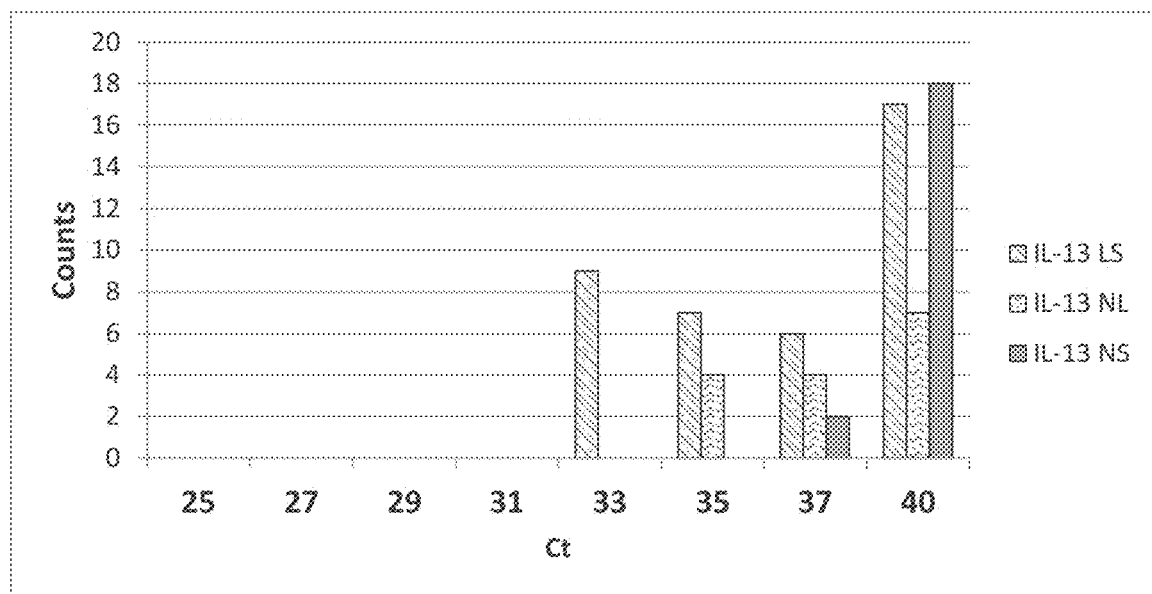
FIG. 27G shows expression of IL-13 in AD lesion skin and non-lesion skin compared to expression of IL-13 in normal skin.
Figure 27H:
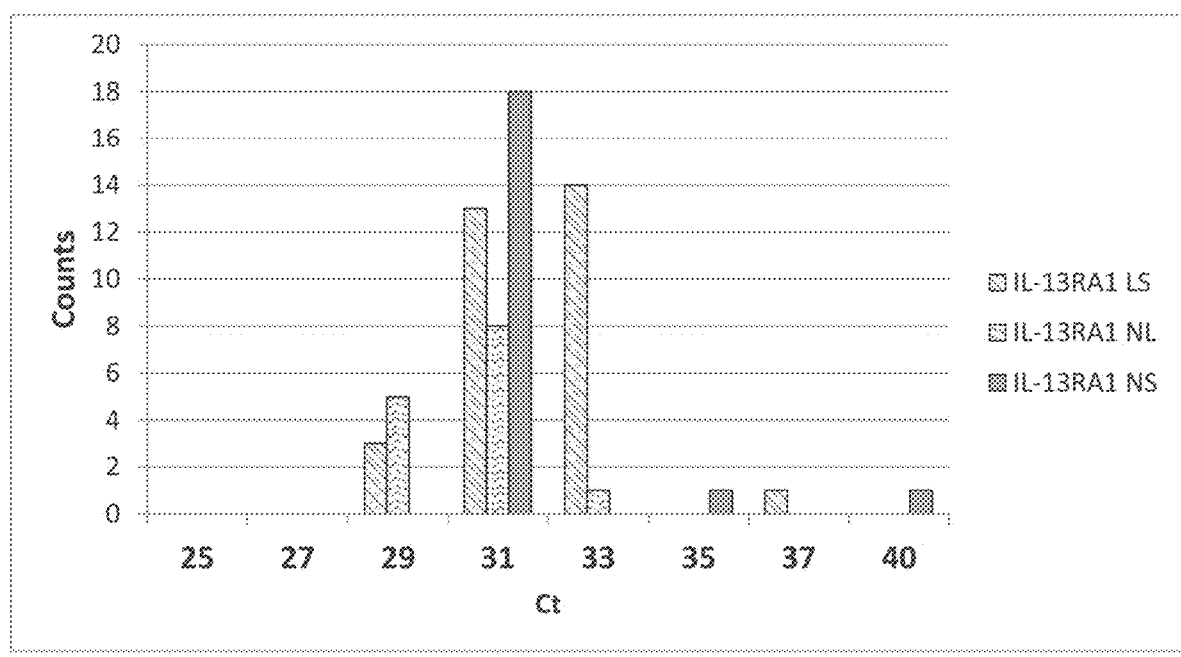
FIG. 27H shows expression of IL-13RA1 in AD lesion skin and non-lesion skin compared to expression of IL-13 RA1 in normal skin.
Figure 27I:
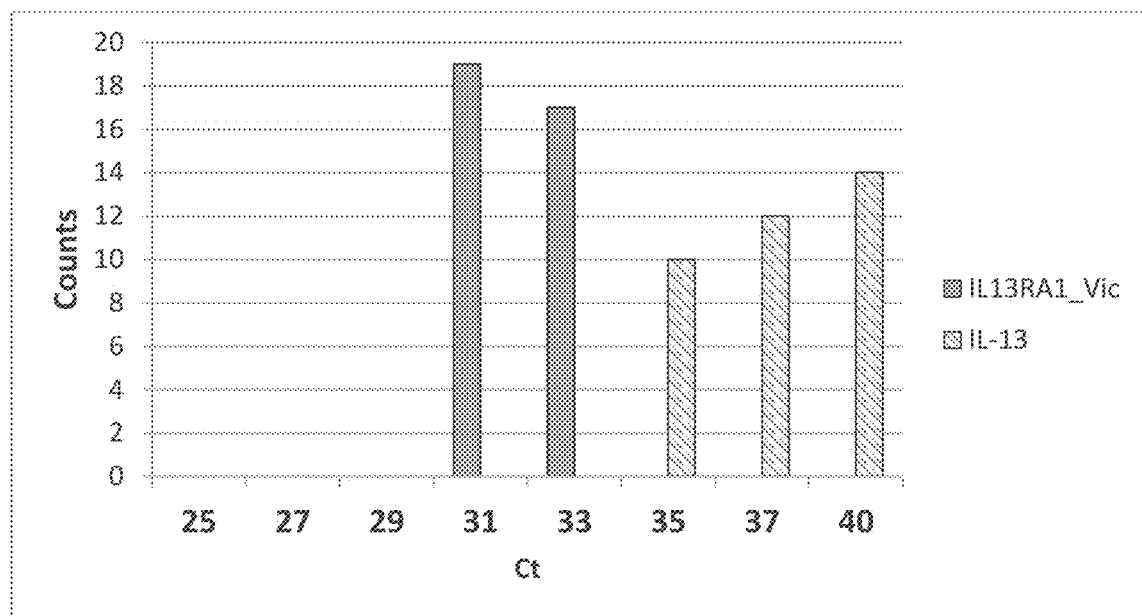
FIG. 27I shows additional expression data for IL13RA1 and IL-13 in AD non-lesion skin samples.

Note:
ΔΔCt = (ΔCt_lesion-ΔCt_normal); FC (fold of change) = $2^{\wedge} \Delta\Delta Ct$ Example 5—Gene Expression Changes in Psoriasis Samples were collected and assayed according to the methods described herein. The fold change of gene expression level in psoriatic lesion skin compared to normal skin and in non-lesional skin compared to normal skin were calculated. FIG. 25 shows the cytokines with increase gene expression detected in both lesional skin and non-lesion area. FIG. 26 shows cytokines with decreased gene expression in uninvolved non-lesional skin but increased gene expression in psoriatic lesional skin.

Example 6—Expanded TH2 Assay for Atopic Dermatitis

Figure 7:
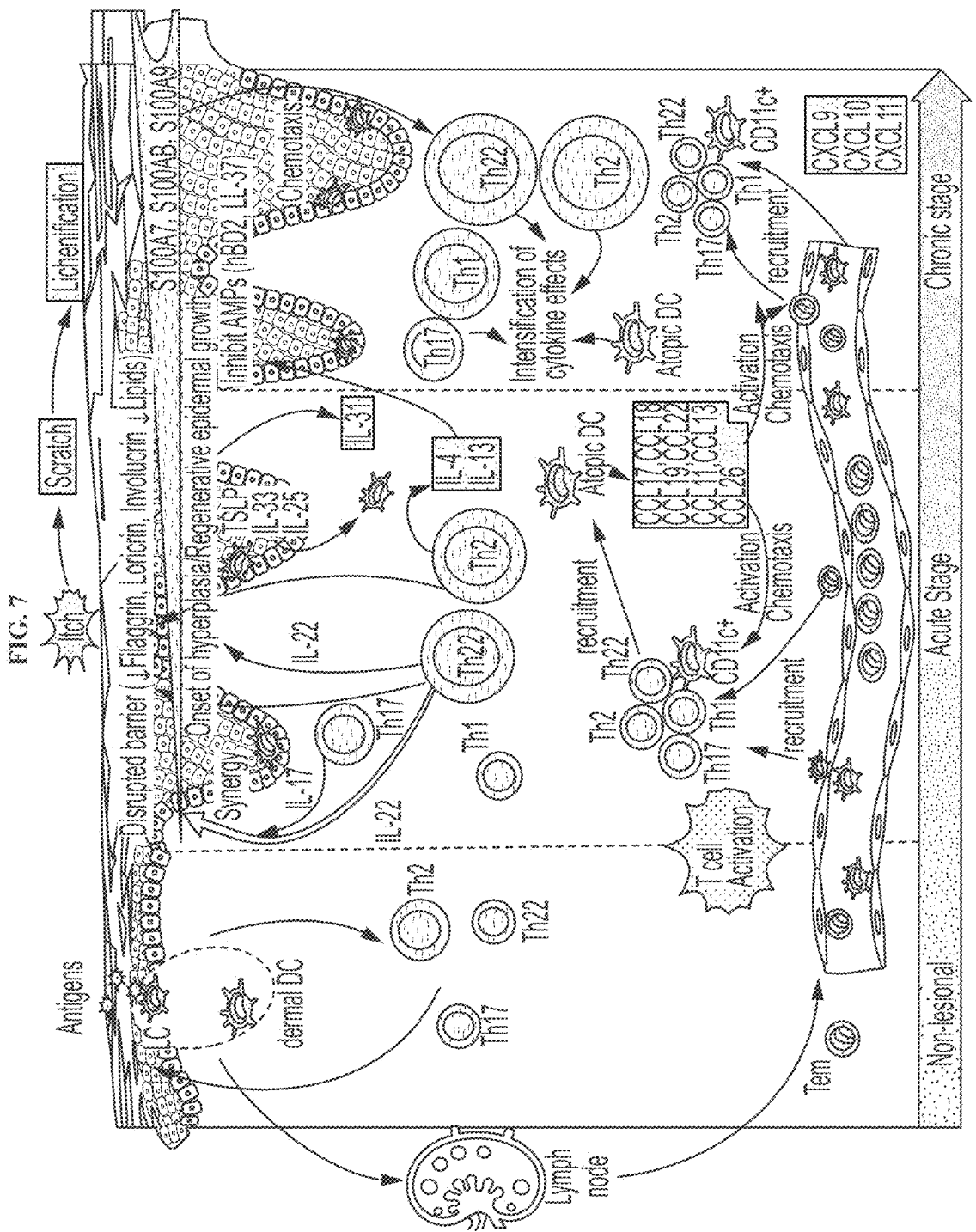
FIG. 7 shows targets for an atopic dermatitis assay and their place in the activation cycle.

Samples were collected using the adhesive patch-based skin biopsy platform described herein and assayed. The modular structure of the qRT-PCR assay allows it to be employed in a number of inflammatory skin conditions including psoriasis, atopic dermatitis or lupus. In atopic dermatitis, the assay focused on 18 targets involved in expanded TH2 pathways (see FIG. 7). Targets included IL-4, IL-13, IL-17, IL-22, IL-31, TSLP, CXCL9, CXCL10, CXCL11, S100A7, S100A8, S100A9, CCL17, CCL18, CCL19, CCL26, CCL27, and NOS2.

Figure 11:
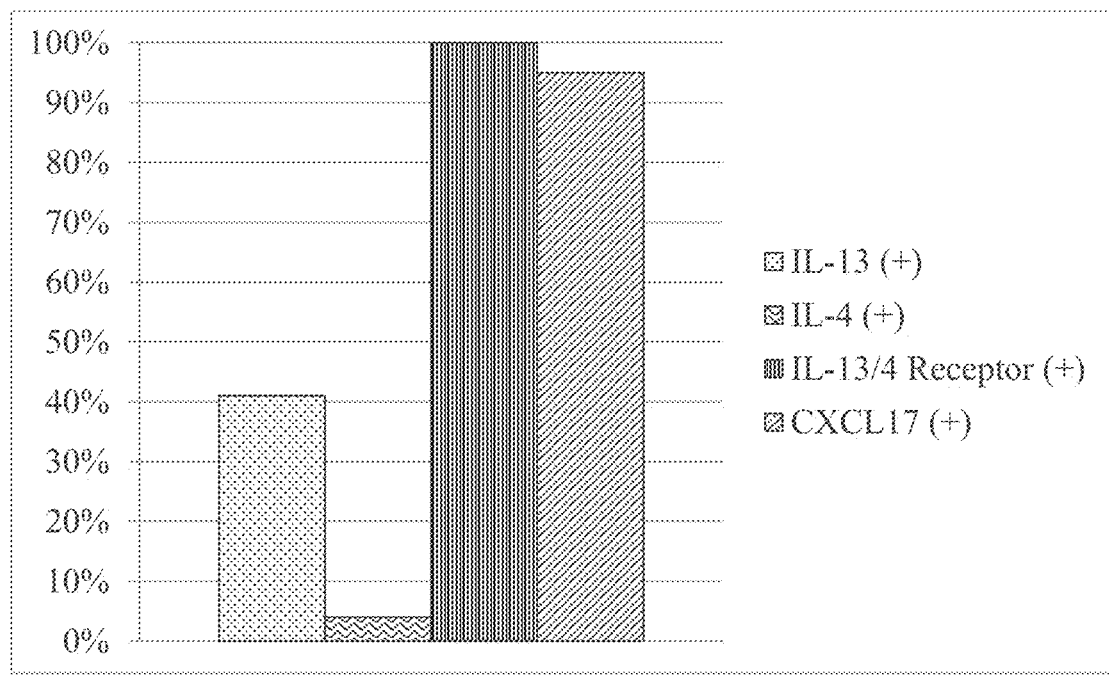
FIG. 11 shows the percentage of subjects with detected expression of IL-13 pathway constituents or receptor using adhesive patch sampling of stratum corneum.

Samples were screened from 39 subjects with atopic dermatitis. As shown in FIG. 11, IL-13 expression was detected in less than half (about 41%) of the subjects. No samples showed IL-4 expression. 100% of samples showed IL-13/4 receptor expression and about 95% exhibited CCL17 expression.

Results suggest selecting for patients with IL-13 expression will lead to a higher proportion of responders to treatment with receptor blocking agents.

Example 7—Expression Levels in AD Samples

Samples from AD subjects were collected and assayed according to the methods described herein. Forty samples from lesional areas, 17 samples from non-lesional areas, and 20 samples from normal skin were assayed for expression levels of IL-31RA, CCL17, IL-23A, IL-4R, IL22, IL-13, and IL-13RA1, see FIGS. 27A-27I and Tables 2A-5B.

TABLE 2A

| Sample Name | Pathology | ACTB-FAM Ct | ACTB-VIC Ct | CCL17_FAM Ct | CCL18_FAM Ct | IL-13_FAM Ct | IL-17A_FAM Ct | IL-22_FAM Ct | IL-4_Vic Ct | IL31_FAM Ct | IL-31RA_1172 FAM Ct |
|---|---|---|---|---|---|---|---|---|---|---|---|
| DT 18-01-01 | Lesion |  | 21.79 | 24.18 | 32.62 | 40.00 | 40.00 | 34.61 | 40.00 | 40.00 | 40.00 |
| DT 18-01-02 | Lesion |  | 22.89 | 40.00 | 37.42 |  |  | 40.00 |  |  | 40.00 |
| DT 18-01-03 | Lesion | 21.22 | 21.76 | 24.44 | 33.29 | 32.50 | 40.00 | 32.06 | 40.00 | 40.00 | 40.00 |
| DT 18-01-04 | Lesion | 20.83 | 21.49 | 24.51 | 32.51 | 31.07 | 33.79 | 30.96 | 40.00 | 40.00 | 40.00 |
| DT 18-01-05 | Lesion | 21.14 | 21.79 | 25.88 | 32.63 | 35.39 | 40.00 | 36.08 | 40.00 | 40.00 | 40.00 |
| DT 18-01-06 | Lesion | 21.12 | 21.85 | 22.84 | 31.49 | 31.43 | 40.00 | 33.29 | 40.00 | 40.00 | 40.00 |
| DT 18-01-07 | Lesion | 27.00 | 27.24 | 30.32 | 40.00 | 40.00 | 40.00 | 40.00 | 40.00 | 40.00 | 40.00 |
| DT 18-01-08 | Lesion | 21.21 | 21.99 | 24.53 | 33.06 | 33.23 | 40.00 | 34.45 | 40.00 | 40.00 | 40.00 |
| DT 18-01-09 | Lesion | 21.73 | 22.14 | 26.92 | 33.73 | 35.84 | 40.00 | 35.21 | 40.00 | 40.00 | 40.00 |
| DT 18-01-10 | Lesion | 21.39 | 21.96 | 25.67 | 40.00 | 40.00 | 40.00 | 40.00 | 40.00 | 36.32 | 35.83 |
| DT 18-01-11 | Lesion | 21.67 | 22.72 | 28.25 | 40.00 | 32.61 | 40.00 | 33.24 | 40.00 | 40.00 | 31.46 |
| DT 18-01-12 | Lesion | 21.52 | 21.82 | 26.04 | 40.00 | 32.30 | 40.00 | 33.58 | 40.00 | 35.66 | 40.00 |
| DT 18-01-13 | Lesion | 21.15 | 21.68 | 25.40 | 40.00 | 32.34 | 40.00 | 34.38 | 40.00 | 35.05 | 30.62 |
| DT 18-01-14 | Lesion | 21.47 | 22.14 | 27.34 | 40.00 | 35.29 | 40.00 | 36.04 | 40.00 | 40.00 | 40.00 |
| DT 18-01-15 | Lesion | 18.80 | 22.35 | 24.14 | 40.00 | 33.31 | 40.00 | 31.67 | 40.00 | 36.41 | 30.72 |
| DT 18-01-16 | Lesion | 23.23 | 23.83 | 28.32 | 40.00 | 34.63 | 40.00 | 34.20 | 40.00 | 40.00 | 40.00 |
| DT 18-01-17 | Lesion | 22.42 | 23.43 | 34.77 | 40.00 | 40.00 | 40.00 | 40.00 | 40.00 | 40.00 | 30.07 |
| DT 18-01-18 | Lesion | 24.32 | 24.28 | 32.85 | 40.00 | 40.00 | 40.00 | 40.00 | 40.00 | 40.00 | 31.57 |
| DT 18-01-19 | Lesion | 24.01 | 24.46 | 26.40 | 40.00 | 40.00 | 40.00 | 40.00 | 40.00 | 40.00 | 40.00 |
| DT 18-01-20 | Lesion | 22.91 | 23.73 | 27.08 | 40.00 | 34.87 | 40.00 | 36.25 | 40.00 | 40.00 | 30.70 |
| DT 18-01-21 | Lesion | 22.41 | 23.22 | 31.52 | 40.00 | 37.14 | 40.00 | 40.00 | 40.00 | 40.00 | 31.54 |
| DT 18-01-22 | Lesion | 22.65 | 23.27 | 28.26 | 40.00 | 40.00 | 40.00 | 40.00 | 40.00 | 40.00 | 40.00 |
| DT 18-01-23 | Lesion | 22.38 | 22.77 | 27.16 | 40.00 | 36.06 | 40.00 | 40.00 | 40.00 | 40.00 | 40.00 |
| DT 18-01-24 | Lesion | 22.72 | 22.82 | 29.32 | 40.00 | 40.00 | 40.00 | 35.06 | 21.87 | 36.45 | 40.00 |
| DT 18-01-25 | Lesion | 23.13 | 23.27 | 30.30 | 40.00 | 40.00 | 40.00 | 40.00 | 40.00 | 40.00 | 40.00 |
| DT 18-01-26 | Lesion | 22.80 | 23.52 | 27.32 | 40.00 | 33.36 | 40.00 | 40.00 | 40.00 | 40.00 | 40.00 |
| DT 18-01-27 | Lesion | 22.28 | 22.97 | 26.82 | 40.00 | 40.00 | 40.00 | 36.76 | 40.00 | 40.00 | 40.00 |
| DT 18-01-28 | Lesion | 22.39 | 22.92 | 24.88 | 40.00 | 36.04 | 40.00 | 34.80 | 40.00 | 36.00 | 35.55 |
| DT 18-01-29 | Lesion | 22.56 | 22.83 | 29.49 | 40.00 | 34.68 | 40.00 | 34.20 | 40.00 | 40.00 | 34.49 |
| DT 18-01-30 | Lesion | 22.39 | 22.73 | 25.73 | 40.00 | 40.00 | 40.00 | 40.00 | 40.00 | 40.00 | 32.75 |
| DT 18-01-31 | Lesion | 29.44 | 29.34 | 40.00 | 40.00 | 40.00 | 40.00 | 40.00 | 40.00 | 40.00 | 35.52 |
| DT 18-01-32 | Lesion | 22.67 | 23.19 | 31.57 | 40.00 | 40.00 | 40.00 | 40.00 | 40.00 | 40.00 | 34.89 |
| DT 18-01-33 | Lesion | 22.89 | 23.34 | 26.58 | 40.00 | 32.73 | 40.00 | 34.43 | 40.00 | 35.70 | 40.00 |
| DT 18-01-34 | Lesion | 22.48 | 22.51 | 33.01 | 40.00 | 40.00 | 40.00 | 40.00 | 40.00 | 40.00 | 33.15 |

TABLE 2B

| Sample Name | Pathology | TSLP_FAM Ct | IL-23A (p19)_FAM Ct | IL-4R_VIC Ct | CCL22_VIC Ct | IL-33_VIC Ct | IL-13RA1_VIC Ct | IL-5_Vic Ct | IL31RA 166 Ct |
|---|---|---|---|---|---|---|---|---|---|
| DT 18-01-01 | Lesion | 36.07 | 29.66 |  |  |  |  |  |  |
| DT 18-01-02 | Lesion | 40.00 | 27.42 |  |  |  |  |  |  |
| DT 18-01-03 | Lesion | 40.00 | 30.65 |  |  |  |  |  |  |
| DT 18-01-04 | Lesion | 40.00 | 31.73 |  |  |  |  |  |  |
| DT 18-01-05 | Lesion | 40.00 | 27.23 |  |  |  |  |  |  |
| DT 18-01-06 | Lesion | 40.00 | 32.95 |  |  |  |  |  |  |
| DT 18-01-07 | Lesion | 40.00 | 35.28 |  |  |  |  |  |  |
| DT 18-01-08 | Lesion | 40.00 | 30.04 |  |  |  |  |  |  |
| DT 18-01-09 | Lesion | 40.00 | 29.77 |  |  |  |  |  |  |
| DT 18-01-10 | Lesion | 40.00 | 32.41 | 29.01 | 40.00 | 40.00 | 29.84 | 40.00 | 40.00 |
| DT 18-01-11 | Lesion | 33.47 | 36.22 | 29.23 | 40.00 | 40.00 | 30.10 | 40.00 | 35.56 |
| DT 18-01-12 | Lesion | 40.00 | 30.55 | 28.44 | 40.00 | 40.00 | 31.52 | 40.00 | 37.53 |
| DT 18-01-13 | Lesion | 36.69 | 31.92 | 27.36 | 40.00 | 40.00 | 29.09 | 40.00 | 34.39 |
| DT 18-01-14 | Lesion | 40.00 | 33.59 | 28.51 | 40.00 | 40.00 | 29.58 | 40.00 | 40.00 |
| DT 18-01-15 | Lesion | 35.51 | 31.73 | 28.03 | 40.00 | 40.00 | 29.35 | 40.00 | 33.57 |
| DT 18-01-16 | Lesion | 34.55 | 32.27 | 27.38 | 40.00 | 40.00 | 32.21 | 40.00 | 40.00 |
| DT 18-01-17 | Lesion | 38.31 | 35.23 | 30.18 | 40.00 | 40.00 | 29.84 | 40.00 | 31.59 |
| DT 18-01-18 | Lesion | 40.00 | 40.00 | 30.20 | 40.00 | 40.00 | 32.20 | 40.00 | 32.71 |
| DT 18-01-19 | Lesion | 40.00 | 34.74 | 24.24 | 40.00 | 40.00 | 32.29 | 40.00 | 40.00 |
| DT 18-01-20 | Lesion | 33.73 | 31.82 | 28.74 | 40.00 | 40.00 | 30.92 | 40.00 | 32.67 |
| DT 18-01-21 | Lesion | 40.00 | 34.59 | 29.16 | 40.00 | 40.00 | 30.21 | 40.00 | 35.38 |
| DT 18-01-22 | Lesion | 40.00 | 33.10 | 30.02 | 40.00 | 40.00 | 31.34 | 40.00 | 40.00 |

TABLE 2B-continued

| Sample Name | Pathology | TSLP_FAM Ct | IL-23A (p19)_FAM Ct | IL-4R_VIC Ct | CCL22_VIC Ct | IL-33_VIC Ct | IL-13RA1_VIC Ct | IL-5_Vic Ct | IL31RA 166 Ct |
|---|---|---|---|---|---|---|---|---|---|
| DT 18-01-23 | Lesion | 40.00 | 34.79 | 29.71 | 40.00 | 40.00 | 31.20 | 40.00 | 40.00 |
| DT 18-01-24 | Lesion | 40.00 | 32.69 | 31.29 | 40.00 | 40.00 | 31.03 | 40.00 | 40.00 |
| DT 18-01-25 | Lesion | 40.00 | 39.78 | 28.64 | 40.00 | 40.00 | 31.42 | 40.00 | 40.00 |
| DT 18-01-26 | Lesion | 40.00 | 32.12 | 29.67 | 40.00 | 40.00 | 31.38 | 40.00 | 40.00 |
| DT 18-01-27 | Lesion | 40.00 | 34.34 | 29.39 | 40.00 | 40.00 | 31.31 | 40.00 | 40.00 |
| DT 18-01-28 | Lesion | 40.00 | 33.39 | 30.48 | 40.00 | 40.00 | 31.33 | 40.00 | 40.00 |
| DT 18-01-29 | Lesion | 40.00 | 32.94 | 29.26 | 40.00 | 40.00 | 29.69 | 40.00 | 40.00 |
| DT 18-01-30 | Lesion | 34.96 | 31.05 | 28.74 | 40.00 | 40.00 | 29.95 | 40.00 | 35.70 |
| DT 18-01-31 | Lesion | 40.00 | 40.00 | 36.30 | 40.00 | 40.00 | 36.79 | 40.00 | 36.39 |
| DT 18-01-32 | Lesion | 40.00 | 40.00 | 31.19 | 40.00 | 40.00 | 29.28 | 40.00 | 35.54 |
| DT 18-01-33 | Lesion | 40.00 | 33.76 | 29.68 | 40.00 | 40.00 | 31.20 | 40.00 | 40.00 |
| DT 18-01-34 | Lesion | 40.00 | 40.00 | 30.14 | 40.00 | 40.00 | 28.87 | 40.00 | 36.02 |

TABLE 3A

| Sample Name | Pathology | ACTB-FAM Ct | ACTB-VIC Ct | CCL17_FAM Ct | CCL18_FAM Ct | IL-13_FAM Ct | IL-17A_FAM Ct | IL-22_FAM Ct | IL-4_Vic Ct | IL31_FAM Ct | IL-31RA_1172 FAM Ct |
|---|---|---|---|---|---|---|---|---|---|---|---|
| DT 18-01-35 | Lesion | 23.40 | 22.81 | 24.30 | 40.00 | 31.99 | 40.00 | 32.23 | 40.00 | 34.04 | 34.86 |
| DT 18-01-36 | Lesion | 22.68 | 22.71 | 24.68 | 40.00 | 40.00 | 40.00 | 36.74 | 40.00 | 40.00 | 40.00 |
| DT 18-01-37 | Lesion | 22.95 | 23.24 | 26.49 | 40.00 | 35.38 | 40.00 | 40.00 | 40.00 | 40.00 | 31.61 |
| DT 18-01-38 | Lesion | 22.47 | 22.81 | 27.67 | 40.00 | 33.01 | 40.00 | 33.81 | 40.00 | 36.32 | 32.87 |
| DT 18-01-39 | Lesion | 22.56 | 23.08 | 25.97 | 40.00 | 40.00 | 40.00 | 40.00 | 40.00 | 40.00 | 40.00 |
| DT 18-01-40 | Lesion | 20.46 | 21.64 | 24.04 | 40.00 | 32.88 | 40.00 | 32.85 | 40.00 | 40.00 | 36.20 |
| DT 18-01-41 | Non-Lesion |  | 23.09 | 30.75 | 40.00 |  |  | 40.00 |  |  | 32.74 |
| DT 18-01-42 | Non-Lesion |  | 22.48 | 24.26 | 33.65 |  |  |  |  |  |  |
| DT 18-01-43 | Non-Lesion | 21.02 | 21.81 | 24.15 | 33.92 | 33.87 | 40.00 | 34.98 | 40.00 | 40.00 | 40.00 |
| DT 18-01-44 | Non-Lesion | 21.18 | 21.80 | 27.40 | 40.00 | 33.59 | 40.00 | 34.49 | 40.00 | 40.00 |  |
| DT 18-01-45 | Non-Lesion | 21.37 | 21.82 | 27.89 | 40.00 | 36.03 | 40.00 | 40.00 | 40.00 | 40.00 | 27.64 |
| DT 18-01-46 | Non-Lesion | 21.21 | 21.76 | 29.64 | 40.00 | 40.00 | 40.00 | 40.00 | 40.00 | 40.00 | 30.54 |
| DT 18-01-47 | Non-Lesion | 21.81 | 21.42 | 31.92 | 40.00 | 40.00 | 40.00 | 40.00 | 40.00 | 40.00 | 26.53 |
| DT 18-01-48 | Non-Lesion | 22.36 | 23.28 | 25.99 | 40.00 | 36.02 | 40.00 | 34.33 | 40.00 | 40.00 | 40.00 |
| DT 18-01-49 | Non-Lesion | 23.34 | 24.05 | 28.41 | 40.00 | 40.00 | 40.00 | 40.00 | 40.00 | 40.00 | 40.00 |
| DT 18-01-50 | Non-Lesion | 22.42 | 23.13 | 27.11 | 40.00 | 40.00 | 40.00 | 40.00 | 40.00 | 40.00 | 35.53 |
| DT 18-01-51 | Non-Lesion | 22.54 | 22.82 | 26.96 | 40.00 | 40.00 | 40.00 | 36.32 | 40.00 | 40.00 | 40.00 |
| DT 18-01-52 | Non-Lesion | 20.19 | 20.57 | 28.84 | 40.00 | 35.49 | 40.00 | 40.00 | 40.00 | 34.90 | 29.38 |
| DT 18-01-53 | Non-Lesion | 22.46 | 22.41 | 26.20 | 40.00 | 33.16 | 40.00 | 36.71 | 40.00 | 35.66 | 35.62 |
| DT 18-01-54 | Non-Lesion | 22.93 | 22.79 | 27.41 | 40.00 | 35.21 | 40.00 | 35.57 | 40.00 | 40.00 | 34.79 |
| DT 18-01-55 | Non-Lesion | 23.09 | 23.51 | 25.97 | 40.00 | 34.31 | 40.00 | 32.54 | 40.00 | 40.00 | 35.88 |
| DT 18-01-56 | Non-Lesion | 22.65 | 23.03 | 25.76 | 40.00 | 40.00 | 40.00 | 32.35 | 40.00 | 40.00 | 40.00 |
| DT 18-01-57 | Non-Lesion | 23.29 | 23.29 | 24.62 | 40.00 | 40.00 | 40.00 | 32.77 | 40.00 | 40.00 | 40.00 |
| DT 18-01-58 | NS_Normal Skin | 23.34 | 24.09 | 32.36 | 40.00 | 40.00 | 40.00 | 40.00 | 40.00 | 40.00 | 34.53 |
| DT 18-01-59 | NS_Normal Skin | 25.63 | 26.19 | 29.38 | 40.00 | 40.00 | 40.00 | 40.00 | 40.00 | 40.00 | 40.00 |
| DT 18-01-60 | NS_Normal Skin | 25.89 | 26.48 | 29.02 | 40.00 | 40.00 | 40.00 | 40.00 | 40.00 | 40.00 | 40.00 |
| DT 18-01-61 | NS_Normal Skin | 22.58 | 23.24 | 38.02 | 40.00 | 40.00 | 40.00 | 40.00 | 40.00 | 40.00 | 28.43 |
| DT 18-01-62 | NS_Normal Skin | 23.24 | 23.92 | 36.74 | 40.00 | 40.00 | 40.00 | 40.00 | 40.00 | 40.00 | 29.67 |
| DT 18-01-63 | NS_Normal Skin | 23.59 | 24.04 | 31.37 | 40.00 | 40.00 | 40.00 | 40.00 | 40.00 | 40.00 | 28.59 |
| DT 18-01-64 | NS_Normal Skin | 23.39 | 24.26 | 33.72 | 40.00 | 40.00 | 40.00 | 36.87 | 40.00 | 40.00 | 28.75 |
| DT 18-01-65 | NS_Normal Skin | 24.41 | 24.53 | 36.23 | 40.00 | 40.00 | 40.00 | 40.00 | 40.00 | 40.00 | 31.40 |
| DT 18-01-66 | NS_Normal Skin | 23.21 | 23.62 | 32.55 | 40.00 | 40.00 | 40.00 | 40.00 | 40.00 | 40.00 | 29.69 |
| DT 18-01-67 | NS_Normal Skin | 23.65 | 23.84 | 40.00 | 40.00 | 40.00 | 40.00 | 40.00 | 40.00 | 40.00 | 29.40 |

TABLE 3B

| Sample Name | Pathology | TSLP_FAM Ct | IL-23A (p19)_FAM Ct | IL-4R_VIC Ct | CCL22_VIC Ct | IL-33_VIC Ct | IL-13RA1_VIC Ct | IL-5_Vic Ct | IL31RA 166 Ct |
|---|---|---|---|---|---|---|---|---|---|
| DT 18-01-35 | Lesion | 40.00 | 34.11 | 29.06 | 40.00 | 40.00 | 31.23 | 40.00 | 40.00 |
| DT 18-01-36 | Lesion | 40.00 | 32.61 | 29.91 | 40.00 | 40.00 | 30.51 | 40.00 | 40.00 |
| DT 18-01-37 | Lesion | 40.00 | 40.00 | 31.05 | 40.00 | 40.00 | 31.27 | 40.00 | 34.60 |
| DT 18-01-38 | Lesion | 40.00 | 36.59 | 30.23 | 40.00 | 40.00 | 28.73 | 40.00 | 36.20 |
| DT 18-01-39 | Lesion | 40.00 | 33.40 | 30.46 | 40.00 | 40.00 | 30.53 | 40.00 | 40.00 |
| DT 18-01-40 | Lesion | 35.06 | 31.18 | 27.91 | 40.00 | 40.00 | 28.68 | 40.00 | 40.00 |
| DT 18-01-41 | Non-Lesion | | 32.46 | | | | | | |
| DT 18-01-42 | Non-Lesion | | 31.38 | | | | | | |
| DT 18-01-43 | Non-Lesion | 40.00 | 31.33 | | | | | | |
| DT 18-01-44 | Non-Lesion | 40.00 | 36.19 | 31.42 | 40.00 | 40.00 | 28.85 | 40.00 | |
| DT 18-01-45 | Non-Lesion | 34.66 | 32.90 | 28.36 | 40.00 | 40.00 | 28.83 | 40.00 | 32.30 |
| DT 18-01-46 | Non-Lesion | 34.01 | 36.30 | 28.80 | 40.00 | 40.00 | 28.59 | 40.00 | 33.55 |
| DT 18-01-47 | Non-Lesion | 35.50 | 40.00 | 28.89 | 40.00 | 40.00 | 30.45 | 40.00 | 29.37 |
| DT 18-01-48 | Non-Lesion | 40.00 | 33.05 | 29.42 | 40.00 | 40.00 | 31.20 | 40.00 | 40.00 |
| DT 18-01-49 | Non-Lesion | 40.00 | 34.71 | 30.95 | 40.00 | 40.00 | 30.47 | 40.00 | 40.00 |
| DT 18-01-50 | Non-Lesion | 40.00 | 32.76 | 30.11 | 40.00 | 40.00 | 30.42 | 40.00 | 40.00 |
| DT 18-01-51 | Non-Lesion | 40.00 | 33.51 | 30.28 | 40.00 | 40.00 | 29.96 | 40.00 | 40.00 |
| DT 18-01-52 | Non-Lesion | 40.00 | 31.71 | 26.90 | 40.00 | 40.00 | 27.84 | 40.00 | 32.81 |
| DT 18-01-53 | Non-Lesion | 40.00 | 34.61 | 29.15 | 40.00 | 40.00 | 29.94 | 40.00 | 40.00 |
| DT 18-01-54 | Non-Lesion | 40.00 | 31.17 | 27.41 | 40.00 | 40.00 | 28.66 | 40.00 | 37.40 |
| DT 18-01-55 | Non-Lesion | 40.00 | 30.65 | 28.92 | 40.00 | 40.00 | 30.82 | 40.00 | 40.00 |
| DT 18-01-56 | Non-Lesion | 40.00 | 33.47 | 28.83 | 40.00 | 40.00 | 30.71 | 40.00 | 37.34 |
| DT 18-01-57 | Non-Lesion | 40.00 | 32.32 | 30.45 | 40.00 | 40.00 | 30.83 | 40.00 | 40.00 |
| DT 18-01-58 | NS_Normal Skin | 40.00 | 40.00 | 30.92 | 40.00 | 40.00 | 30.01 | 40.00 | 36.57 |
| DT 18-01-59 | NS_Normal Skin | 40.00 | 35.35 | 30.79 | 40.00 | 40.00 | 34.00 | 40.00 | 25.44 |
| DT 18-01-60 | NS_Normal Skin | 40.00 | 40.00 | 33.89 | 40.00 | 40.00 | 37.44 | 40.00 | 40.00 |
| DT 18-01-61 | NS_Normal Skin | 36.29 | 40.00 | 30.69 | 40.00 | 40.00 | 30.20 | 40.00 | 32.30 |
| DT 18-01-62 | NS_Normal Skin | 40.00 | 40.00 | 30.58 | 40.00 | 40.00 | 30.92 | 40.00 | 32.17 |
| DT 18-01-63 | NS_Normal Skin | 35.28 | 36.31 | 29.67 | 40.00 | 40.00 | 29.45 | 40.00 | 31.68 |
| DT 18-01-64 | NS_Normal Skin | 35.70 | 40.00 | 30.76 | 40.00 | 40.00 | 30.68 | 40.00 | 31.16 |
| DT 18-01-65 | NS_Normal Skin | 37.85 | 40.00 | 32.07 | 40.00 | 40.00 | 30.08 | 40.00 | 33.78 |
| DT 18-01-66 | NS_Normal Skin | 40.00 | 40.00 | 31.00 | 40.00 | 40.00 | 29.40 | 40.00 | 32.32 |
| DT 18-01-67 | NS_Normal Skin | 40.00 | 40.00 | 30.80 | 40.00 | 40.00 | 29.85 | 40.00 | 32.35 |

TABLE 4A

| Sample Name | Pathology | ACTB-FAM Ct | ACTB-VIC Ct | CCL17_FAM Ct | CCL18_FAM Ct | IL-13_FAM Ct | IL-17A_FAM Ct | IL-22_FAM Ct | IL-4_Vic Ct | IL31_FAM Ct | IL-31RA_1172 FAM Ct |
|---|---|---|---|---|---|---|---|---|---|---|---|
| DT 18-01-68 | NS_Normal Skin | 23.91 | 24.18 | 29.50 | 40.00 | 36.46 | 40.00 | 35.63 | 40.00 | 36.61 | 32.79 |
| DT 18-01-69 | NS_Normal Skin | 23.54 | 24.03 | 35.00 | 40.00 | 40.00 | 40.00 | 36.62 | 40.00 | 40.00 | 29.97 |
| DT 18-01-70 | NS_Normal Skin | 23.94 | 24.35 | 35.37 | 40.00 | 40.00 | 40.00 | 40.00 | 40.00 | 40.00 | 30.76 |
| DT 18-01-71 | NS_Normal Skin | 23.57 | 24.31 | 32.01 | 40.00 | 36.02 | 40.00 | 40.00 | 40.00 | 40.00 | 30.88 |
| DT 18-01-72 | NS_Normal Skin | 23.19 | 23.86 | 27.83 | 40.00 | 40.00 | 40.00 | 40.00 | 40.00 | 40.00 | 29.97 |
| DT 18-01-73 | NS_Normal Skin | 23.33 | 23.88 | 32.67 | 40.00 | 40.00 | 40.00 | 40.00 | 40.00 | 40.00 | 30.00 |
| DT 18-01-74 | NS_Normal Skin | 23.91 | 24.45 | 40.00 | 40.00 | 40.00 | 40.00 | 40.00 | 40.00 | 40.00 | 40.00 |
| DT 18-01-75 | NS_Normal Skin | 23.30 | 24.22 | 33.59 | 40.00 | 40.00 | 40.00 | 40.00 | 40.00 | 40.00 | 30.57 |
| DT 18-01-76 | NS_Normal Skin | 23.37 | 23.79 | 30.57 | 40.00 | 40.00 | 40.00 | 36.31 | 40.00 | 40.00 | 29.34 |

TABLE 4A-continued

| Sample Name | Pathology | | ACTB-FAM Ct | ACTB-VIC Ct | CCL17_FAM Ct | CCL18_FAM Ct | IL-13_FAM Ct | IL-17A_FAM Ct | IL-22_FAM Ct | IL-4_Vic Ct | IL31_FAM Ct | IL-31RA_1172 FAM Ct |
|---|---|---|---|---|---|---|---|---|---|---|---|---|
| DT 18-01-77 | NS_Normal Skin | | 23.63 | 24.16 | 33.21 | 40.00 | 40.00 | 40.00 | 40.00 | 40.00 | 40.00 | 28.71 |
| NTC | | | 40.00 | 40.00 | 40.00 | 40.00 | 40.00 | 40.00 | 40.00 | 40.00 | 40.00 | 40.00 |
| NTC | | | 40.00 | 40.00 | 40.00 | 40.00 | 40.00 | 40.00 | 40.00 | 40.00 | 40.00 | 40.00 |
| | Np. Cases | | | | | | | | | | | |
| Lesion | 40 | Median | 22.44 | 22.82 | 26.87 | 40.00 | 35.84 | 40.00 | 36.17 | 40.00 | 40.00 | 40.00 |
| Non-Lesion | 17 | | 22.42 | 22.79 | 27.11 | 40.00 | 36.03 | 40.00 | 36.51 | 40.00 | 40.00 | 35.62 |
| NS | 0 | | 23.56 | 24.13 | 32.94 | 40.00 | 40.00 | 40.00 | 40.00 | 40.00 | 40.00 | 29.99 |
| Δ (LS-NL) | | | 0.02 | 0.03 | −0.24 | 0.00 | −0.18 | 0.00 | −0.35 | 0.00 | 0.00 | 4.38 |
| Δ (LS-NS) | | | −1.12 | −1.31 | −6.07 | 0.00 | −4.16 | 0.00 | −3.83 | 0.00 | 0.00 | 10.01 |
| Δ (NL-NS) | | | −1.13 | −1.34 | −5.83 | 0.00 | −3.97 | 0.00 | −3.49 | 0.00 | 0.00 | 5.64 |
| | | Ct Bins | Ct Distribution count | | | | | | | | | |
| Lesion | | 25 | 36 | | 10 | | 0 | | 0 | | | 0 |
| | | 27 | 0 | | 11 | | 0 | | 0 | | | 0 |
| | | 29 | 1 | | 8 | | 0 | | 0 | | | 0 |
| | | 31 | 1 | | 4 | | 0 | | 1 | | | 4 |
| | | 33 | 0 | | 3 | | 9 | | 4 | | | 6 |
| | | 35 | 0 | | 2 | | 7 | | 11 | | | 4 |
| | | 37 | 0 | | 0 | | 6 | | 7 | | | 4 |
| | | 40 | 0 | | 2 | | 17 | | 17 | | | 22 |
| Non-Lesion | | 25 | 15 | | 3 | | 0 | | 0 | | | 0 |

TABLE 4B

| Sample Name | Pathology | | TSLP_FAM Ct | IL-23A (p19)_FAM Ct | IL-4R_VIC Ct | CCL22_VIC Ct | IL-33_VIC Ct | IL-13RA1_VIC Ct | IL-5_Vic Ct | IL31RA 166 Ct |
|---|---|---|---|---|---|---|---|---|---|---|
| DT 18-01-68 | NS_Normal Skin | | 40.00 | 35.22 | 31.09 | 40.00 | 40.00 | 30.73 | 40.00 | 33.87 |
| DT 18-01-69 | NS_Normal Skin | | 40.00 | 36.25 | 31.49 | 40.00 | 40.00 | 29.76 | 40.00 | 32.92 |
| DT 18-01-70 | NS_Normal Skin | | 40.00 | 36.18 | 30.65 | 40.00 | 40.00 | 30.62 | 40.00 | 33.45 |
| DT 18-01-71 | NS_Normal Skin | | 40.00 | 40.00 | 31.41 | 40.00 | 40.00 | 30.46 | 40.00 | 32.68 |
| DT 18-01-72 | NS_Normal Skin | | 40.00 | 40.00 | 31.21 | 40.00 | 40.00 | 30.20 | 40.00 | 32.54 |
| DT 18-01-73 | NS_Normal Skin | | 40.00 | 36.31 | 30.43 | 40.00 | 40.00 | 29.77 | 40.00 | 32.00 |
| DT 18-01-74 | NS_Normal Skin | | 40.00 | 34.93 | 31.47 | 40.00 | 40.00 | 29.76 | 40.00 | 40.00 |
| DT 18-01-75 | NS_Normal Skin | | 34.17 | 35.87 | 31.47 | 40.00 | 40.00 | 29.55 | 40.00 | 32.89 |
| DT 18-01-76 | NS_Normal Skin | | 33.74 | 32.83 | 29.57 | 40.00 | 40.00 | 30.23 | 40.00 | 32.04 |
| DT 18-01-77 | NS_Normal Skin | | 34.51 | 33.88 | 29.99 | 40.00 | 40.00 | 30.76 | 40.00 | 32.07 |
| NTC | | | 40.00 | 40.00 | 40.00 | 40.00 | 40.00 | 40.00 | 40.00 | 40.00 |
| NTC | | | 40.00 | 40.00 | 40.00 | 40.00 | 40.00 | 40.00 | 40.00 | 40.00 |
| | Np. Cases | | | | | | | | | |
| Lesion | 40 | Median | 40.00 | 33.02 | 29.39 | 40.00 | 40.00 | 30.92 | 40.00 | 40.00 |
| Non-Lesion | 17 | | 40.00 | 32.90 | 29.04 | 40.00 | 40.00 | 30.19 | 40.00 | 40.00 |
| NS | 0 | | 40.00 | 38.16 | 30.86 | 40.00 | 40.00 | 30.20 | 40.00 | 32.45 |
| Δ (LS-NL) | | | 0.00 | 0.13 | 0.35 | 0.00 | 0.00 | 0.74 | 0.00 | 0.00 |
| Δ (LS-NS) | | | 0.00 | −5.13 | −1.47 | 0.00 | 0.00 | 0.73 | 0.00 | 7.55 |
| Δ (NL-NS) | | | 0.00 | −5.26 | −1.82 | 0.00 | 0.00 | −0.01 | 0.00 | 7.55 |
| | | Ct Bins | | | | | | | | |
| Lesion | | 25 | 0 | 1 | | | 0 | | 0 | |
| | | 27 | 0 | 0 | | | 0 | | 0 | |
| | | 29 | 2 | 9 | | | 3 | | 0 | |

TABLE 4B-continued

| Sample Name | Pathology | TSLP_FAM Ct | IL-23A (p19)_FAM Ct | IL-4R_VIC Ct | CCL22_VIC Ct | IL-33_VIC Ct | IL-13RA1_VIC Ct | IL-5_Vic Ct | IL31RA 166 Ct |
|---|---|---|---|---|---|---|---|---|---|
| | 31 | | 5 | 17 | | | 13 | | 0 |
| | 33 | | 13 | 3 | | | 14 | | 3 |
| | 35 | | 10 | 0 | | | 0 | | 3 |
| | 37 | | 4 | 1 | | | 1 | | 7 |
| | 40 | | 6 | 0 | | | 0 | | 18 |
| Non-Lesion | 25 | | 0 | 0 | | | 0 | | 0 |

TABLE 5A

| Sample Name | Pathology | ACTB-FAM Ct | ACTB-VIC Ct | CCL17_FAM Ct | CCL18_FAM Ct | IL-13_FAM Ct | IL-17A_FAM Ct | IL-22_FAM Ct | IL-4_Vic Ct | IL31_FAM Ct | IL-31RA_1172 FAM Ct |
|---|---|---|---|---|---|---|---|---|---|---|---|
| | 27 | 0 | | 5 | | 0 | | 0 | | | 1 |
| | 29 | 0 | | 6 | | 0 | | 0 | | | 1 |
| | 31 | 0 | | 2 | | 0 | | 0 | | | 2 |
| | 33 | 0 | | 1 | | 0 | | 3 | | | 1 |
| | 35 | 0 | | 0 | | 4 | | 3 | | | 1 |
| | 37 | 0 | | 0 | | 4 | | 3 | | | 3 |
| | 40 | 0 | | 0 | | 7 | | 7 | | | 6 |
| NS | 25 | 18 | | 0 | | 0 | | 0 | | | 0 |
| | 27 | 2 | | 0 | | 0 | | 0 | | | 0 |
| | 29 | 0 | | 1 | | 0 | | 0 | | | 4 |
| | 31 | 0 | | 4 | | 0 | | 0 | | | 10 |
| | 33 | 0 | | 5 | | 0 | | 0 | | | 2 |
| | 35 | 0 | | 4 | | 0 | | 0 | | | 1 |
| | 37 | 0 | | 3 | | 2 | | 4 | | | 0 |
| | 40 | 0 | | 3 | | 18 | | 18 | | | 3 |

TABLE 5B

| Sample Name | Pathology | TSLP_FAM Ct | IL-23A (p19)_FAM Ct | IL-4R_VIC Ct | CCL22_VIC Ct | IL-33_VIC Ct | IL-13RA1_VIC Ct | IL-5_Vic Ct | IL31RA 166 Ct |
|---|---|---|---|---|---|---|---|---|---|
| | 27 | | 0 | 1 | | | 0 | | 0 |
| | 29 | | 0 | 6 | | | 5 | | 0 |
| | 31 | | 1 | 6 | | | 8 | | 1 |
| | 33 | | 8 | 1 | | | 1 | | 2 |
| | 35 | | 5 | 0 | | | 0 | | 1 |
| | 37 | | 2 | 0 | | | 0 | | 0 |
| | 40 | | 1 | 0 | | | 0 | | 9 |
| NS | 25 | | 0 | 0 | | | 0 | | 0 |
| | 27 | | 0 | 0 | | | 0 | | 1 |
| | 29 | | 0 | 0 | | | 0 | | 0 |
| | 31 | | 0 | 11 | | | 18 | | 0 |
| | 33 | | 1 | 8 | | | 0 | | 13 |
| | 35 | | 2 | 1 | | | 1 | | 3 |
| | 37 | | 7 | 0 | | | 0 | | 1 |
| | 40 | | 10 | 0 | | | 1 | | 2 |

Example 8—IL-13/4 Receptor Blocking with Dupilumab

AD subjects were treated with 300 mg dupilumab with subcutaneous administration every other week for 16 weeks. Samples were collected as described in Example 5.

Figure 8:
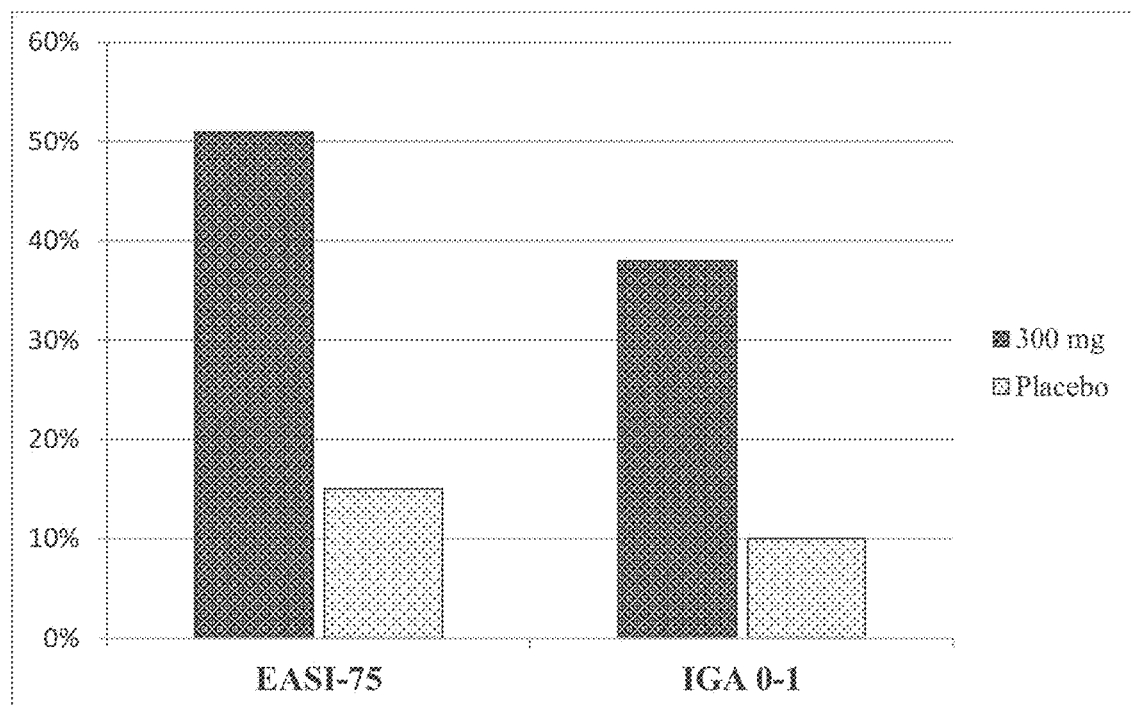
FIG. 8 shows the percentage of subjects achieving an 75% reduction from baseline in the Eczema Area and Severity Index (EASI-75) or IGA score of cleared (0) or minimal (1) (IGA 0-1) score after 16 weeks treatment with 300 mg dupilumab or placebo.

About 50% of test subjects achieved 75% reduction in symptoms (EASI-75) compared to about 15% of placebo subjects achieving EASI-75 (FIG. 8). Additionally, about 38% of subjects achieved an IGA score of cleared (0) or minimal (1) (IGA 0-1) compared to about 10% of placebo subjects.

Example 9—IL-13 Blocking with Lebrikizumab

AD subjects were treated with 125 mg lebrikizumab, an IL-13 blocking monoclonal antibody, and corticosteroids weekly for 12 weeks. Samples were collected as described in Example 5.

Figure 9:
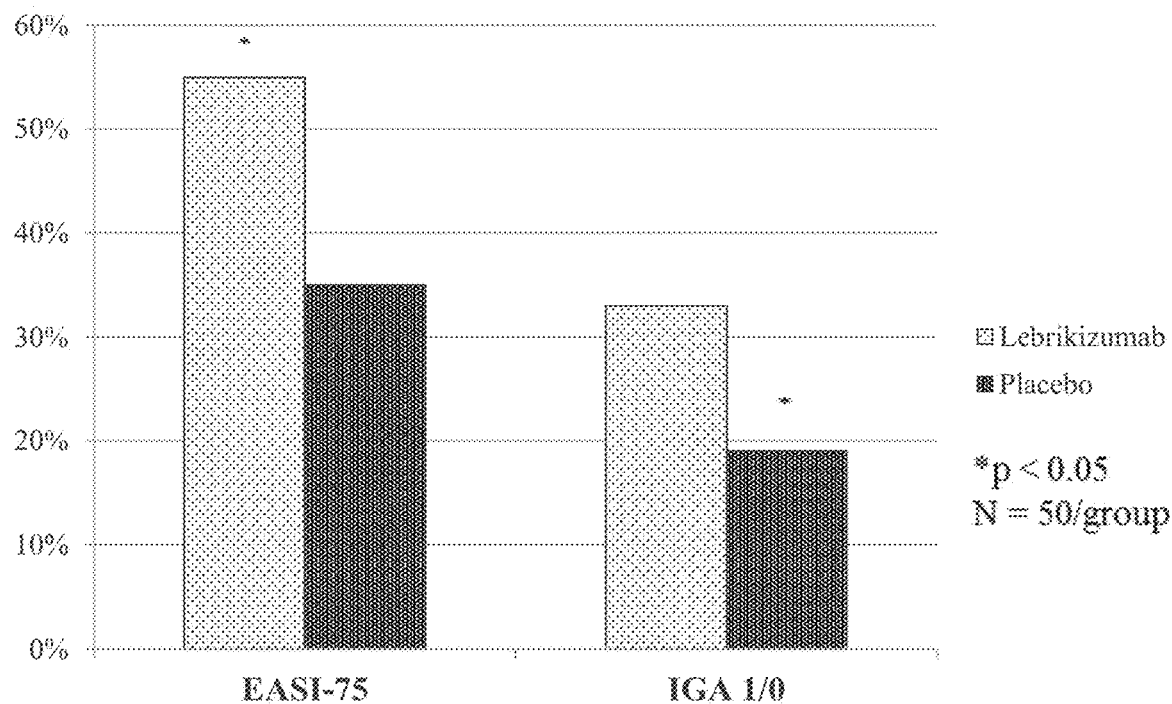
FIG. 9 shows the percentage of subjects achieving EASI-75 or IGA I/O after 125 mg/week for 12 weeks treatment with Lebrikizumab or placebo.

About 55% of test subjects achieved EASI-75 compared to about 34% of placebo subjects (n-50/group, p=0.05) (see FIG. 9)

Example 10—IL-13 Blocking with Tralokinumab

AD subjects were tested for DPP-4 levels in the blood. Treatment and placebo groups were further selected for elevated DPP-4 levels. Treatment groups received tralokinumab, an IL-13 blocking monoclonal antibody, and topical steroids for 12 weeks. Samples were collected as described in Example 5.

Figure 10:
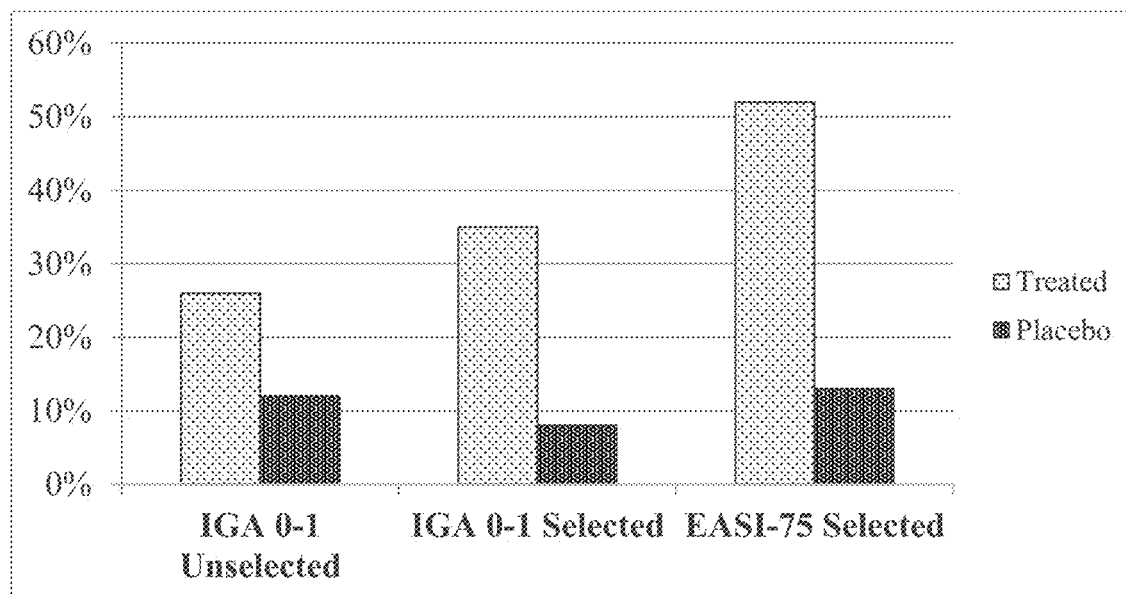
FIG. 10 shows the percentage of subjects achieving EASI-75 or IGA 0/1 in and unselected population and subjects selected for elevated DPP-4 levels following 12 weeks treatment with Tralokinumab or placebo.

As shown in FIG. 10, groups not selected for elevated DPP-4 levels, about 26% of treatment subjects achieved IGA 0-1 compared to about 12% of placebo subjects. In groups selected for elevated DPP-4 levels, about 35% of test subjects achieved IGA 0-1 compared to IGA 0-18% of placebo subjects. In groups selected for elevated DPP-4 levels, about 52% of treatment subjects achieved EASI-75 as compared to about 13% of placebo subjects.

Results show tralokinumab resolves AD symptoms in subject and resolves symptoms to a higher degree in subjects exhibiting elevated DPP-4 levels in the blood.

Example 11—Expression of CCL17 in AD Lesion and Non-Lesion Areas

Figure 12A:
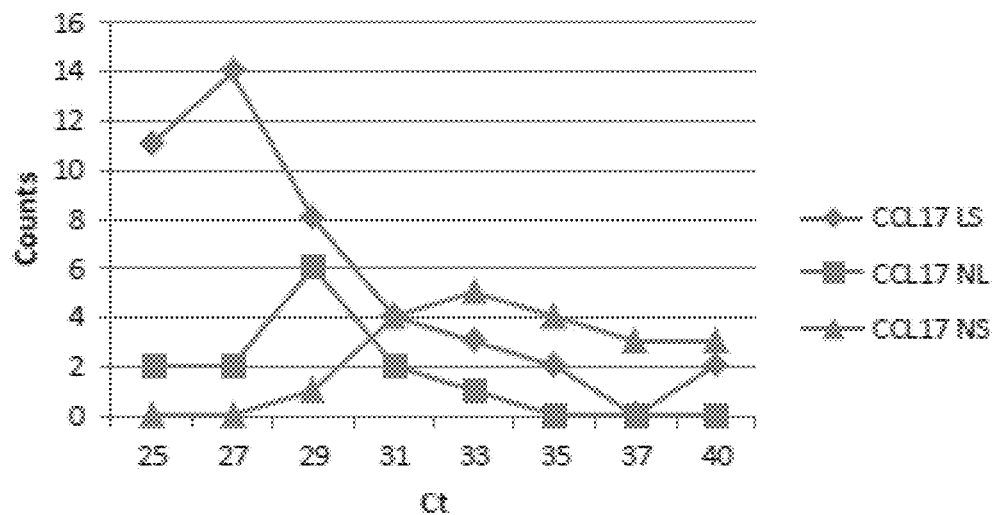
FIG. 12A shows expression of CCL17 in lesion and non-lesion skins compared to healthy normal skin.
Figure 12B:
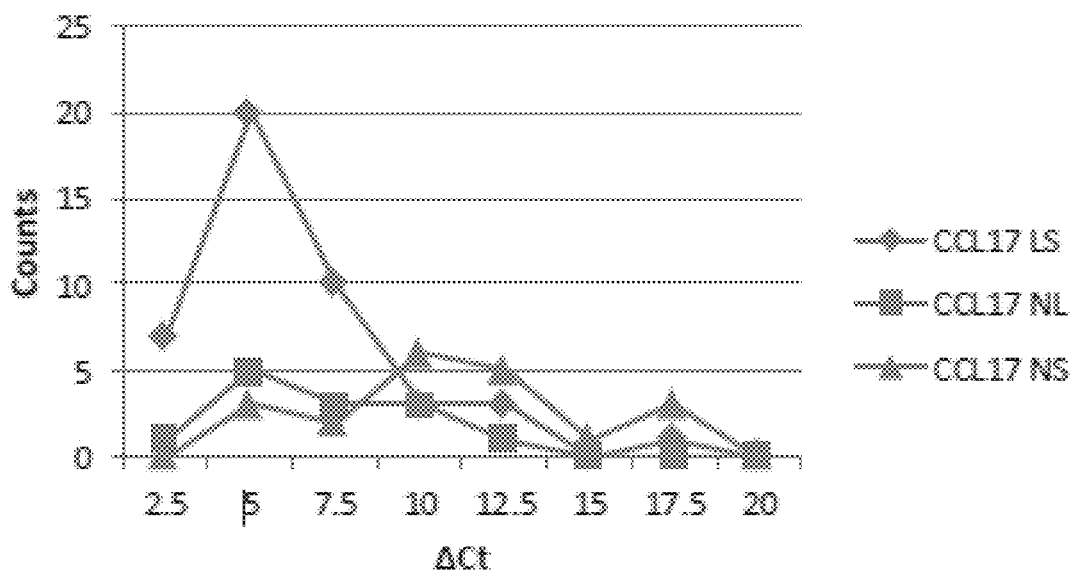
FIG. 12B shows the normalized gene expression change of CCL17 in lesion and non-lesion skins compared to healthy normal skin.
Figure 13A:
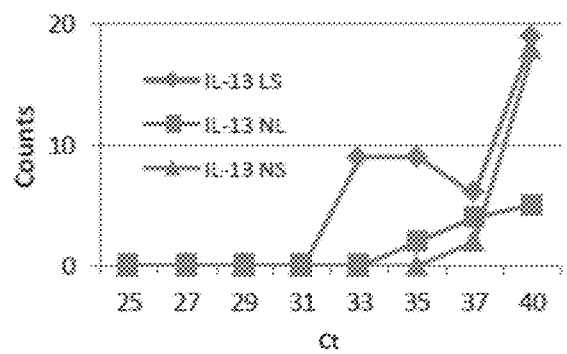
FIG. 13A shows expression of IL-13 in lesion and non-lesion skins compared to healthy normal skin.
Figure 13B:
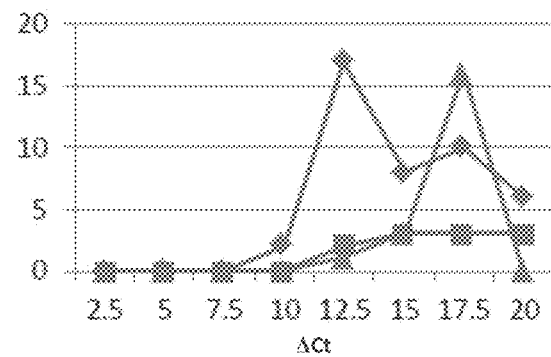
FIG. 13B shows the normalized gene expression change of IL-13 in lesion and non-lesion skins compared to healthy normal skin.
Figure 14A:
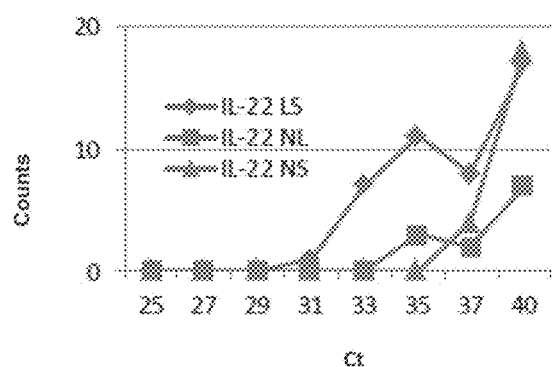
FIG. 14A shows expression of IL-22 in lesion and non-lesion skins compared to healthy normal skin.
Figure 14B:
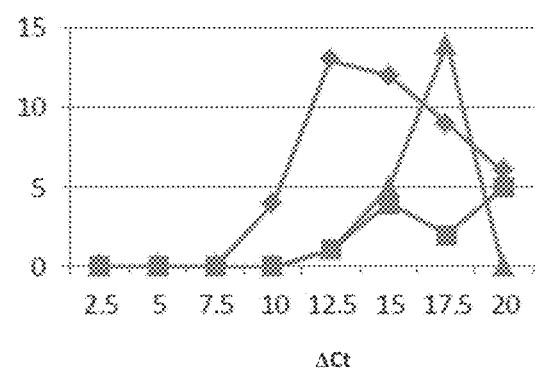
FIG. 14B shows the normalized gene expression change of IL-22 in lesion and non-lesion skins compared to healthy normal skin.
Figure 15A:
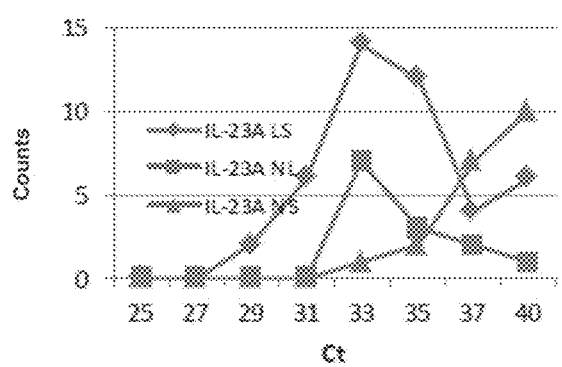
FIG. 15A shows expression of IL-23A (p19) in lesion and non-lesion skins compared to healthy normal skin.
Figure 15B:
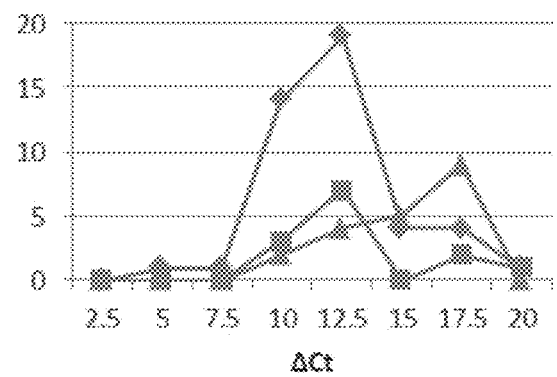
FIG. 15B shows the normalized gene expression change of IL-23A (p19) in lesion and non-lesion skins compared to healthy normal skin.

AD samples were collected from using the adhesive patch-based skin biopsy platform described herein and assayed. Lesional and non-lesional areas as well as normal skin were tested for CCL17 expression (FIG. 12A and FIG. 12B). ΔCt analysis shows that although changes are more severe in lesional skin samples, the changing patterns are similar in both the lesional and non-lesional samples from AD subjects, suggesting non-lesional samples may be used as a mode of disease diagnosis. ΔCt=normalized gene expression change (=$CT_{target\ gene}-Ct_{ACTB}$). A larger ΔCt value means less expression of the target gene. A smaller ΔCt value means more expression of the target gene.

Example 12—Expression Levels of IL-13, IL-22, and IL-23A in AD Samples

AD samples were collected from using the adhesive patch-based skin biopsy platform described herein and assayed. Lesional and non-lesional areas as well as normal skin were tested for IL-13, IL-22, and IL-23A expression levels (FIGS. 13A, 13B, 14A, 14B, 15A, and 15B). ΔCt analysis shows all three cytokines have very low gene expression levels in healthy skin samples (triangles), but show different gene expression patterns in different AD samples (diamonds). Expression levels were either remarkably increased, as indicated by a reduced Ct, or remained unchanged, as shown by a high Ct. It is considered that differential gene expression may be related to "responders" or "non-responders" of the disease and as such, IL-13, IL-22, and IL-23A expression is a potential for screening responders from non-responders.

Example 13—Expression Levels of IL-31 and IL-31R in AD Samples

AD samples were collected from using the adhesive patch-based skin biopsy platform described herein and assayed. Lesional and non-lesional areas as well as normal skin were tested for IL-31 and IL-31R expression levels (FIGS. 16A, 16B, 17A, 17B, 18A, and 18B). Similar to cytokine IL-4, IL-31 is another cytokine important in regulating AD disease. Some increase in IL-31 is detected in lesional samples. IL-31 receptor (IL-31R) shows reduced gene expression in lesional samples.

Example 14—Expression Levels of IL-13 and IL31RA1 in AD Samples

Figure 19:
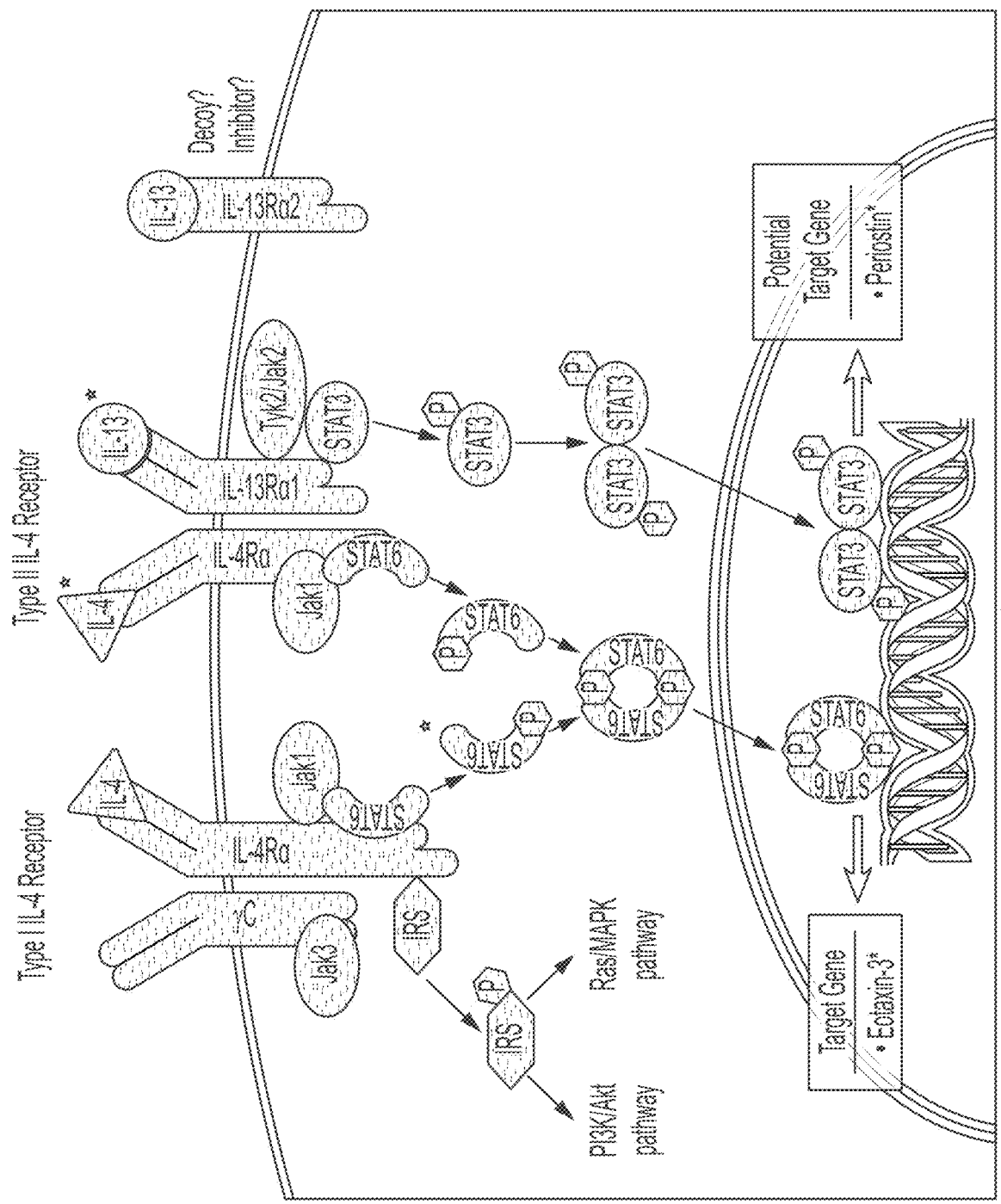
FIG. 19 shows IL-13 and IL-4 signaling pathways.
Figure 20A:
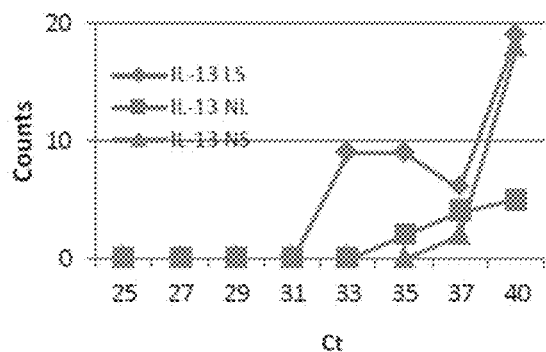
FIG. 20A shows expression of IL-13 in lesion and non-lesion skins compared to healthy normal skin.
Figure 20B:
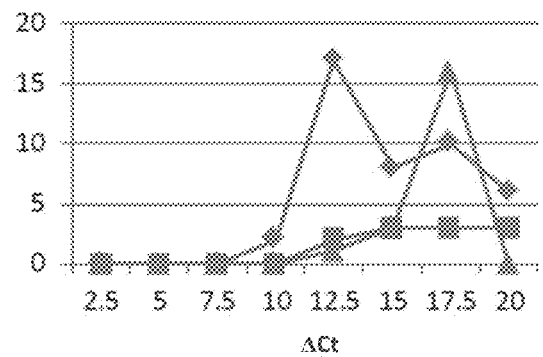
FIG. 20B shows normalized gene expression change of IL-13 in lesion and non-lesion skins compared to healthy normal skin.
Figure 21A:
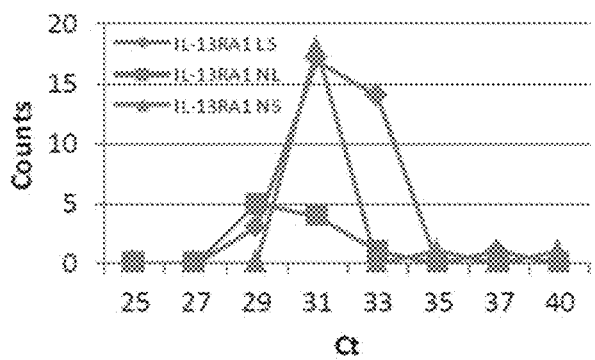
FIG. 21A shows expression of IL-13RA1 in lesion and non-lesion skins compared to healthy normal skin.
Figure 21B:
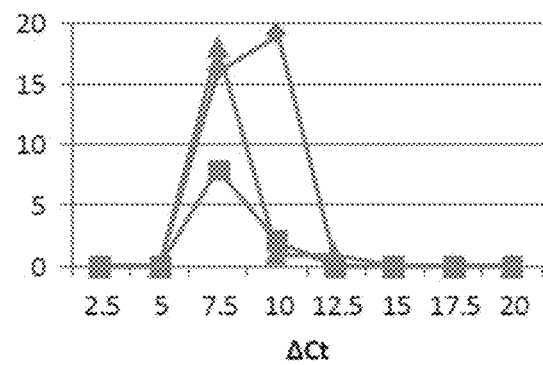
FIG. 21B shows normalized gene expression change of IL-13RA1 in lesion and non-lesion skins compared to healthy normal skin.
Figure 22A:
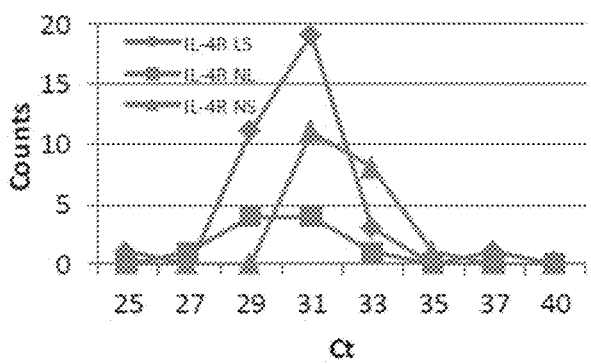
FIG. 22A shows expression of IL-4R in lesion and non-lesion skins compared to healthy normal skin.
Figure 22B:
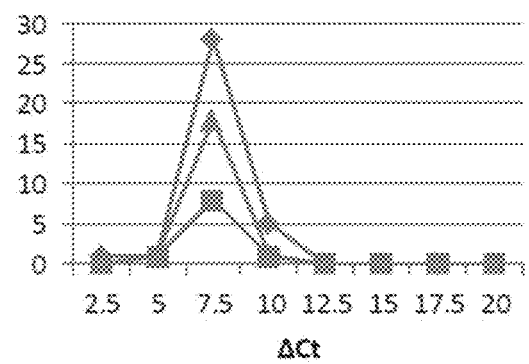
FIG. 22B shows normalized gene expression change of IL-4R in lesion and non-lesion skins compared to healthy normal skin.

IL-13 and IL-4 are proposed to work in AD according to the pathway depicted in FIG. 19. AD samples were collected from using the adhesive patch-based skin biopsy platform described herein and assayed. Lesional and non-lesional areas as well as normal skin were tested for IL-13, IL-13RA1, and IL4R expression. Results are shown in FIGS. 20A, 20B, 21A, 21B, 22A, and 22B. An increase in IL-13 expression was detected and accompanied by a decrease in the gene expression of its receptor, IL-13RA1. IL-4 gene expression was not detected in the samples, while IL-4R showed expression level that remained unchained in AD samples as compared to normal skin.

These results suggest that IL-13 plays a more significant role that IL-4 in AD disease regulation.

Example 15—Expression Levels of NOS2 in AD Samples

Figure 23:
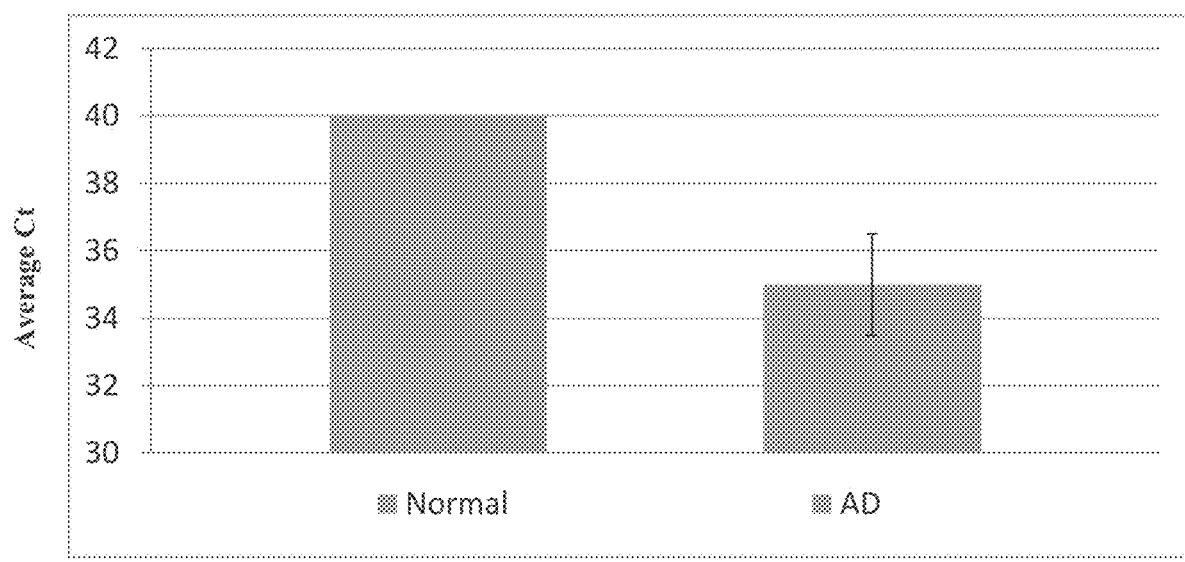
FIG. 23 shows exemplary gene expression changes in AD samples compared to normal, in this case expression of NOS2.

AD samples were collected from using the adhesive patch-based skin biopsy platform described herein and assayed for NOS2 expression levels. Results in FIG. 23 show AD samples with a lower average Ct compared to normal skin samples, indicating an increased expression level in AD samples.

Example 16—Expanded Interferon Response Gene Assay for Lupus

Figure 24:
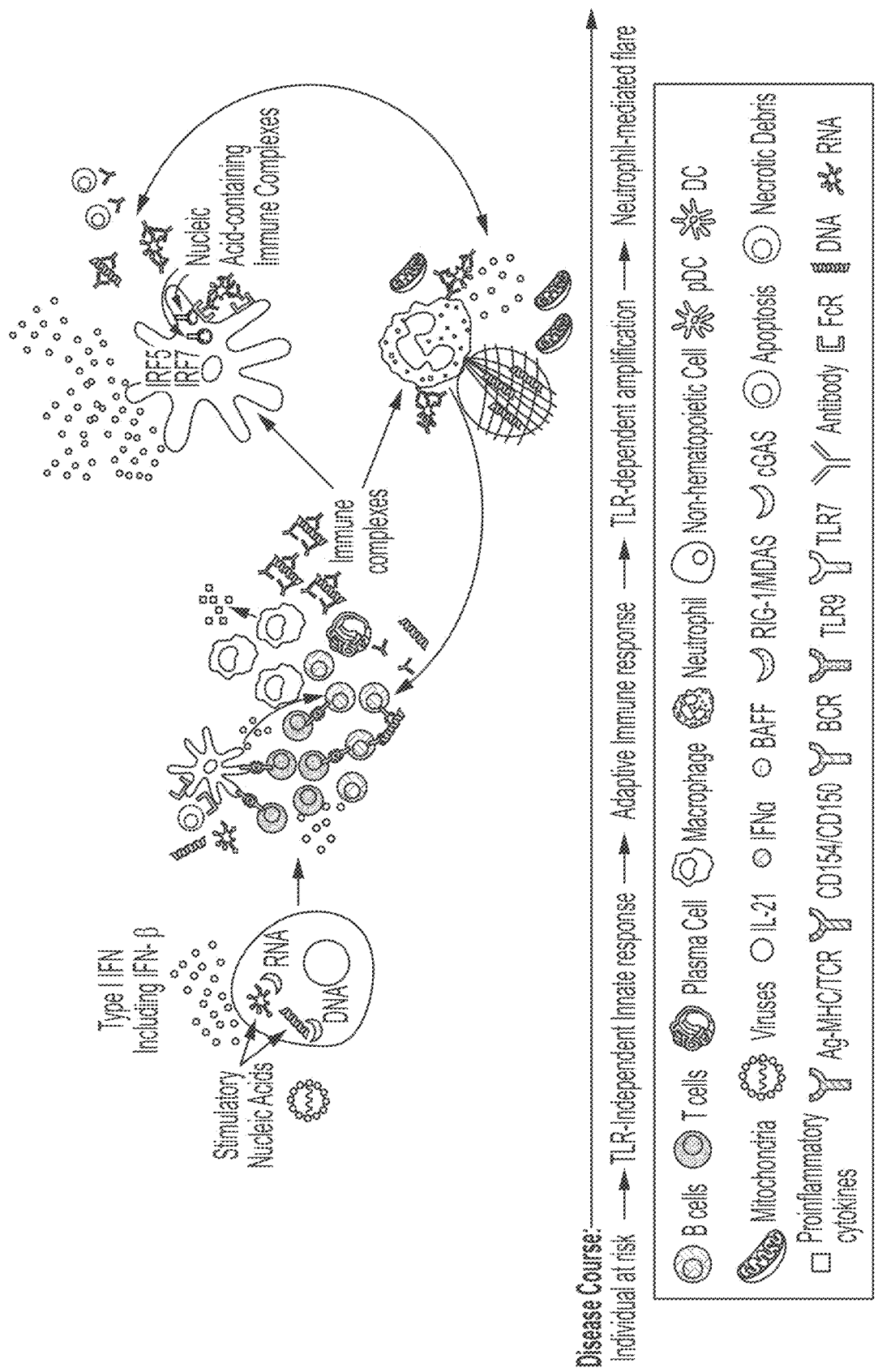
FIG. 24 shows the pathogenesis of Lupus.

Samples are collected using the adhesive patch-based skin biopsy platform described herein and assayed. The modular structure of the qRT-PCR assay allows it to be employed in a number of inflammatory skin conditions including psoriasis, atopic dermatitis or lupus. In lupus, the assay focused on 21 targets involved in a neutrophil-mediated flare (see FIG. 24). Targets include IFNA1, IFNA2, IFNA4, IFNAR1, IFNAR2, IFNB1, IFNE, IFNW1, ADAR, CCL5, IFIT's, IFI's, IRF's, OAS1, IRAK1, TNFAIP3, ATG5, TYK2, STAT4, OPN, and KRT's.

Lesional and non-lesional adhesive patch biopsy samples from patients with moderate to severe lupus are tested against 21 selected targets by qRT-PCR to show differences in gene expression signatures of lesional, non-lesional and non-lupus control skin.

Embodiment 1: A method of detecting gene expression levels of at least two of IL-17A, IL-17F, IL-8, CXCL5, S100A9, and DEFB4A in a subject suspected of having psoriasis, comprising: (a) isolating nucleic acids from a skin sample obtained from the subject, where the skin sample comprises cells from the stratum corneum; and (b) detecting the expression levels of at least two of IL-17A, IL-17F, IL-8, CXCL5, S100A9, and DEFB4A by contacting the isolated nucleic acids with a set of probes that recognizes at least two of IL-17A, IL-17F, IL-8, CXCL5, S100A9, and DEFB4A, and detect binding between at least two of IL-17A, IL-17F, IL-8, CXCL5, S100A9, and DEFB4A and the set of probes.

Embodiment 2: The method of embodiment 1, wherein the method comprises detecting the expression levels of at least three, at least four, or at least five of IL-17A, IL-17F, IL-8, CXCL5, S100A9, and DEFB4A.

Embodiment 3: The method of embodiment 1, wherein the method comprises detecting the expression levels of IL-17A, IL-17F, IL-8, CXCL5, S100A9, and DEFB4A.

Embodiment 4: The method of embodiment 1, wherein the method comprises detecting the expression levels of IL-17A, IL-17F, IL-8, CXCL5, and S100A9.

Embodiment 5: The method of embodiment 1, wherein the method comprises detecting the expression levels of IL-17A, IL-17F, IL-8, and CXCL5.

Embodiment 6: The method of embodiment 1, wherein the method comprises detecting the expression levels of IL-17A, IL-17F, and IL-8.

Embodiment 7: The method of embodiment 1, wherein the method comprises detecting the expression levels of IL-17A, and IL-17F.

Embodiment 8: The method of any one of the embodiments 1-7, wherein the expression level is an up-regulated gene expression level, compared to a gene expression level of an equivalent gene from a control sample.

Embodiment 9: The method of embodiment 8, wherein the gene expression levels of IL-17A, IL-17F, IL-8, CXCL5, S100A9, and DEFB4A are upregulated.

Embodiment 10: The method of any one of the embodiments 1-9, wherein the set of probes recognizes at least two but no more than six genes.

Embodiment 11: The method of embodiment 1, wherein the detecting comprises contacting the isolated nucleic acids with an additional set of probes that recognizes IL-17C, S100A7, IL-17RA, IL-17RC, IL-23A, IL-22, IL-26, IL-24, IL-6, CXCL1, TNFα, LCN2, CCL20, TNFRSF1A, or a combination thereof.

Embodiment 12: The method of embodiment 11, wherein the additional set of probes recognizes one but no more than fourteen genes.

Embodiment 13: A method of detecting gene expression levels from a first gene classifier and a second gene classifier in a subject suspected of having psoriasis, comprising: (a) isolating nucleic acids from a skin sample obtained from the subject, wherein the skin sample comprises cells from the stratum corneum; (b) detecting the expression levels of one or more genes from the first gene classifier: IL-17A, IL-17F, IL-8, CXCL5, S100A9, and DEFB4A, by contacting the isolated nucleic acids with a set of probes that recognizes one or more genes from the first gene classifier, and detects binding between one or more genes from the first gene classifier and the set of probes; and (c) detecting the expression levels of one or more genes from the second gene classifier: IL-17C, S100A7, IL-17RA, IL-17RC, IL-23A, IL-22, IL-26, IL-24, IL-6, CXCL1, IFN-gamma, IL-31, IL-33, TNFα, LCN2, CCL20, and TNFRSF1A, by contacting the isolated nucleic acids with an additional set of probes that recognizes one or more genes from the second gene classifier, and detects binding between one or more genes from the second gene classifier and the additional set of probes.

Embodiment 14: The method of embodiment 13, wherein the method comprises detecting the expression levels of IL-17A and IL-17F from the first gene classifier.

Embodiment 15: The method of embodiment 13, wherein the method comprises detecting the expression levels of IL-8, CXCL5, S100A9, and DEFB4A from the first gene classifier.

Embodiment 16: The method of embodiment 13, wherein the method comprises detecting the expression levels of IL-17A, IL-8, and DEFB4A from the first gene classifier.

Embodiment 17: The method of embodiment 13, wherein the method comprises detecting the expression levels of IL-17F, CXCL5, and S100A9 from the first gene classifier.

Embodiment 18: The method of embodiment 13, wherein the method comprises detecting the expression levels of IL-17A, IL-17F, IL-8, CXCL5, S100A9, and DEFB4A from the first gene classifier.

Embodiment 19: The method of any one of the embodiments 13-18, wherein the expression level is an up-regulated gene expression level, compared to a gene expression level of an equivalent gene from a control sample.

Embodiment 20: The method of embodiment 19, wherein the gene expression level of IL-17A, IL-17F, IL-8, CXCL5, S100A9, or DEFB4A is up-regulated.

Embodiment 21: The method of any one of the embodiments 13-20, wherein the set of probes recognizes at least one but no more than six genes.

Embodiment 22: The method of any one of the embodiments 13-20, wherein the additional set of probes recognizes at least one but no more than 17 genes.

Embodiment 23: The method of any one of the embodiments 13-22, wherein the method further comprises determining the expression level of one or more genes from the second classifier are upregulated.

Embodiment 24: The method of any one of the embodiments 1-23, further comprising administering to the subject an inhibitor of TNFα, IL-17A, or IL-23.

Embodiment 25: The method of embodiment 24, wherein if the subject has an altered gene expression level of at least two of IL-17A, IL-17F, IL-8, CXCL5, S100A9, and DEFB4A, the subject is administered with an inhibitor of TNFα, or the level of the treatment is increased.

Embodiment 26: The method of embodiment 24, wherein if the subject has an altered gene expression level of at least two of IL-17A, IL-17F, IL-8, CXCL5, S100A9, and DEFB4A, the subject is administered with an inhibitor of IL-17A, or the level of the treatment is increased.

Embodiment 27: The method of embodiment 24, wherein if the subject has an altered gene expression level of at least two of IL-17A, IL-17F, IL-8, CXCL5, S100A9, and DEFB4A, the subject is administered with an inhibitor of IL-23, or the level of the treatment is increased.

Embodiment 28: A method of treating a subject with an inhibitor of TNFα, IL-17A, or IL-23, wherein the subject has psoriasis, the method comprising the steps of:
 determining whether the subject has an altered gene expression level by:
  isolating nucleic acids from a skin sample comprising cells from the stratum corneum; and performing or having performed an expression analysis on the skin sample by contacting the isolated nucleic acids with a set of probes that recognizes at least two of IL-17A, IL-17F, IL-8, CXCL5, S100A9, and DEFB4A, and detect binding between at least two of IL-17A, IL-17F, IL-8, CXCL5, S100A9, and DEFB4A and the set of probes; and if the subject has an altered gene expression level of at least two of IL-17A, IL-17F, IL-8, CXCL5, S100A9, and DEFB4A, then administer to the subject an inhibitor of TNFα, IL-17A, or IL-23 or increase the level of the treatment with the inhibitor, and if the subject does not have an altered gene expression level of at least two of IL-17A, IL-17F, IL-8, CXCL5, S100A9, and DEFB4A, then does not administer the inhibitor or discontinue the treatment with the inhibitor.

Embodiment 29: The method of embodiment 28, wherein if the subject has an altered gene expression level of at least two of IL-17A, IL-17F, IL-8, CXCL5, S100A9, and DEFB4A, the subject is administered with an inhibitor of TNFα, or the level of the treatment is increased.

Embodiment 30: The method of embodiment 29, wherein the altered gene expression is an increase in expression.

Embodiment 31: The method of embodiment 28, wherein if the subject has an altered gene expression level of at least two of IL-17A, IL-17F, IL-8, CXCL5, S100A9, and DEFB4A, the subject is administered with an inhibitor of IL-17A, or the level of the treatment is increased.

Embodiment 32: The method of embodiment 31, wherein the altered gene expression is an increase in expression.

Embodiment 33: The method of embodiment 28, wherein if the subject has an altered gene expression level of at least two of IL-17A, IL-17F, IL-8, CXCL5, S100A9, and DEFB4A, the subject is administered with an inhibitor of IL-23, or the level of the treatment is increased.

Embodiment 34: The method of embodiment 33, wherein the altered gene expression is an increase in expression.

Embodiment 35: The method of embodiment 28, wherein the set of probes recognizes at least two of IL-17A, IL-17F, and IL-8.

Embodiment 36: The method of embodiment 28, wherein the set of probes recognizes CXCL5, S100A9, and DEFB4A.

Embodiment 37: A method of detecting gene expression levels of at least two of IL-13, IL-31, and TSLP in a subject suspected of having atopic dermatitis, comprising: (a) isolating nucleic acids from a skin sample obtained from the subject, where the skin sample comprises cells from the stratum corneum; and (b) detecting the expression levels of at least two of IL-13, IL-31, and TSLP by contacting the isolated nucleic acids with a set of probes that recognizes at least two of IL-13, IL-31, and TSLP, and detect binding between at least two of IL-13, IL-31, and TSLP and the set of probes.

Embodiment 38: The method of embodiment 37, wherein the method comprises detecting the expression levels of at least two or at least three of IL-13, IL-31, and TSLP.

Embodiment 39: The method of embodiment 37, wherein the method comprises detecting the expression levels of IL-13, IL-31, and TSLP.

Embodiment 40: The method of embodiment 37, wherein the method comprises detecting the expression levels of IL-13 and IL-31.

Embodiment 41: The method of embodiment 37, wherein the method comprises detecting the expression levels of IL-13 and TSLP.

Embodiment 42: The method of embodiment 37, wherein the expression level is an up-regulated gene expression level, compared to a gene expression level of an equivalent gene from a control sample.

Embodiment 43: The method of embodiment 42, wherein the gene expression levels of IL-13, IL-31, and TSLP are upregulated.

Embodiment 44: The method of embodiment 37, wherein the set of probes recognizes at least two but no more than three genes.

Embodiment 45: The method of embodiment 37, wherein the detecting comprises contacting the isolated nucleic acids with an additional set of probes that recognizes IL-13R, IL-4R, IL-17, IL-22, CXCL9, CXCL10, CXCL11, S100A7, S100A8, S100A9, CCL17, CCL18, CCL19, CCL26, CCL27, NOS2, or a combination thereof.

Embodiment 46: The method of embodiment 45, wherein the additional set of probes recognizes one but no more than sixteen genes.

Embodiment 47: A method of detecting gene expression levels from a first gene classifier and a second gene classifier in a subject suspected of having atopic dermatitis, comprising: (a) isolating nucleic acids from a skin sample obtained from the subject, wherein the skin sample comprises cells from the stratum corneum; (b) detecting the expression levels of one or more genes from the first gene classifier: IL-13, IL-31, and TSLP, by contacting the isolated nucleic acids with a set of probes that recognizes one or more genes from the first gene classifier, and detects binding between one or more genes from the first gene classifier and the set of probes; and (c) detecting the expression levels of one or more genes from the second gene classifier: IL-13R, IL-4R, IL-17, IL-22, CXCL9, CXCL10, CXCL11, S100A7, S100A8, S100A9, CCL17, CCL18, CCL19, CCL26, CCL27, and NOS2, by contacting the isolated nucleic acids with an additional set of probes that recognizes one or more genes from the second gene classifier, and detects binding between one or more genes from the second gene classifier and the additional set of probes.

Embodiment 48: The method of embodiment 47, wherein the method comprises detecting the expression levels of IL-13 and IL-31 from the first gene classifier.

Embodiment 49: The method of embodiment 47, wherein the method comprises detecting the expression levels of IL-31 and TSLP from the first gene classifier.

Embodiment 50: The method of embodiment 47, wherein the method comprises detecting the expression levels of IL-13 and TSLP from the first gene classifier.

Embodiment 51: The method of any one of the embodiments 47-50, wherein the expression level is an up-regulated gene expression level, compared to a gene expression level of an equivalent gene from a control sample.

Embodiment 52: The method of embodiment 51, wherein the gene expression level of IL-13, IL-31, or TSLP is up-regulated.

Embodiment 53: The method of any one of the embodiments 47-52, wherein the set of probes recognizes at least one but no more than three genes.

Embodiment 54: The method of any one of embodiments 47-52, wherein the additional set of probes recognizes at least one but no more than 16 genes.

Embodiment 55: The method of any one of the embodiments 47-54, wherein the method further comprises determining the expression level of one or more genes from the second classifier are upregulated.

Embodiment 56: The method of any one of embodiments 37-55, further comprising administering to the subject an inhibitor of IL-13, PDE4, or IL-31.

Embodiment 57: The method of embodiment 56, wherein if the subject has an altered gene expression level of at least two of IL-13, IL-31, or TSLP, the subject is administered with an inhibitor of IL-13, or the level of the treatment is increased.

Embodiment 58: The method of embodiment 57, wherein the inhibitor of IL-13 is lebrikizumab or tralokinumab.

Embodiment 59: The method of embodiment 56, wherein if the subject has an altered gene expression level of at least two of IL-13, IL-31, or TSLP, the subject is administered with an inhibitor of PDE4, or the level of the treatment is increased.

Embodiment 60: The method of embodiment 56, wherein if the subject has an altered gene expression level of at least two of IL-13, IL-31, or TSLP, the subject is administered with an inhibitor of IL-31, or the level of the treatment is increased.

Embodiment 61: A method of treating a subject with an antibody that specifically binds to interleukin-13 (IL-13) or interleukin-13 receptor (IL-13R), wherein the subject has atopic dermatitis, the method comprising the steps of:
  determining whether the subject has an altered gene expression level by:
    obtaining or having obtained isolating nucleic acids from a skin sample comprising cells from the stratum corneum; and
    performing or having performed an expression analysis on the skin sample by contacting the isolated nucleic acids with a set of probes that recognizes at least two of IL-13, IL-31, and TSLP, and detect binding between at least two of IL-13, IL-31, and TSLP, and the set of probes; and
  if the subject has an altered gene expression level of at least two of IL-13, IL-31, and TSLP, then administer to the subject an antibody that specifically binds to IL-13 or IL-13R, and
  if the subject does not have an altered gene expression level of at least two of IL-13, IL-31, and TSLP, then do not administer the antibody that specifically binds to IL-13 or IL-13R.

Embodiment 62: The method of embodiment 61, wherein if the subject has an altered gene expression of at least two of IL-13, IL-31, and TSLP, the subject is administered an inhibitor of IL-13 or IL-13R, or the level of treatment is increased.

Embodiment 63: The method of embodiment 62, wherein the altered gene expression is an increase in expression.

Embodiment 64: The method of embodiment 61, wherein the antibody that specifically binds to IL-13 is lebrikizumab or tralokinumab.

Embodiment 65: The method of embodiment 61, wherein the antibody that specifically binds to IL-13R is dupilumab.

Embodiment 66: The method of any one of the embodiments 1-65, wherein the nucleic acids comprise RNA, DNA, or a combination thereof.

Embodiment 67: The method of embodiment 66, wherein the RNA is mRNA.

Embodiment 68: The method of embodiment 66, wherein the RNA is cell-free circulating RNA.

Embodiment 69: The method of any one of the embodiments 1-68, wherein the cells from the stratum corneum comprises T cells or components of T cells.

Embodiment 70: The method of any one of the embodiments 1-68, wherein the cells from the stratum corneum comprises keratinocytes.

Embodiment 71: The method of any one of the embodiments 1-70, wherein the skin sample is obtained by applying an adhesive patch to a skin region of the subject in a manner sufficient to adhere cells to the adhesive patch, and removing the adhesive patch from the skin region in a manner sufficient to retain the adhered cells to the adhesive patch.

Embodiment 72: The method of any one of the embodiments 1-70, wherein the skin sample is obtained by applying a plurality of adhesive patches to a skin region of the subject in a manner sufficient to adhere cells to each of the adhesive patches, and removing each of the adhesive patches from the skin region in a manner sufficient to retain the adhered cells to each of the adhesive patches.

Embodiment 73: The method of embodiment 72, wherein the plurality of adhesive patches comprises at least 4 adhesive patches.

Embodiment 74: The method of any one of the embodiments 1-73, wherein the amount of nucleic acids isolated from the skin sample is from about 100 picograms to about 100 micrograms, from about 200 picograms to about 10 micrograms, or from about 500 picograms to about 1 microgram.

Embodiment 75: The method of any one of the embodiments 1-74, wherein the expression level of genes is monitored over the course of 1 week, 2 weeks, 3 weeks, 1 month, 2 months, 6 months, or more.

Embodiment 76: The method of any of the preceding embodiments, wherein the subject is a human.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for preparing nucleic acids from a skin sample useful for detecting atopic dermatitis in a human subject, comprising:
   a) isolating nucleic acids from a skin sample obtained from the subject, where the skin sample is obtained by applying an adhesive patch to the subject's skin;
   b) detecting gene expression levels of one or more target genes, comprising at least IL-31, by contacting the isolated nucleic acids with probes that recognize nucleic acids expressed by the target genes and detecting binding of the probes;
   c) identifying that expression levels of the one or more target genes are increased at least two-fold compared to a normal control sample,
   d) diagnosing the subject with the at least two-fold increase in gene expression as having atopic dermatitis; and
   e) administering an inhibitor of one or more of IL-13, PDE4 and IL-31 to the diagnosed subject.

2. The method of claim 1, wherein the one or more target genes are used in a gene classifier.

3. The method of claim 2, wherein the gene classifier comprises IL-13 or TSLP.

4. The method of claim 3, wherein the expression level comprises an upregulated expression level of IL-13 or TSLP, relative to one or more controls.

5. The method of claim 2, wherein the gene classifier comprises IL-13 and TSLP.

6. The method of claim 5, wherein the expression levels of IL-13, or TSLP is increased relative to one or more controls.

7. The method of claim 6, wherein b) comprises detecting the expression levels of IL-13, IL-31, and TSLP by contacting the isolated nucleic acids with a set of probes that recognizes IL-13, IL-31, and TSLP, and detecting binding between IL-13, IL-31, and TSLP and the set of probes.

8. The method of claim 1, further comprising:
detecting the expression level of IL-13R, IL-4R, IL-17, IL-22, IL-23A, CXCL9, CXCL10, CXCL11, S100A7, S100A8, S100A9, CCL17, CCL18, CCL19, CCL26, CCL27, or NOS2, by contacting the isolated nucleic acids with an additional probe that recognizes IL-13R, IL-4R, IL-17, IL-22, IL-23A, CXCL9, CXCL10, CXCL11, S100A7, S100A8, S100A9, CCL17, CCL18, CCL19, CCL26, CCL27, or NOS2, and detecting binding between IL-13R, IL-4R, IL-17, IL-22, IL-23A, CXCL9, CXCL10, CXCL11, S100A7, S100A8, S100A9, CCL17, CCL18, CCL19, CCL26, CCL27, or NOS2 and the additional probe.

9. The method of claim 8, wherein IL-13 is used in a first gene classifier, and one or more of the following genes is used in a second gene classifier: IL-13R, IL-4R, IL-17, IL-22, IL-23A, CXCL9, CXCL10, CXCL11, S100A7, S100A8, S100A9, CCL17, CCL18, CCL19, CCL26, CCL27, or NOS2.

10. The method of claim 9, wherein two or more of the following genes is used in the second gene classifier: IL-13R, IL-4R, IL-17, IL-22, IL-23A, CXCL9, CXCL10, CXCL11, S100A7, S100A8, S100A9, CCL17, CCL18, CCL19, CCL26, CCL27, or NOS2.

11. The method of claim 10, wherein b) comprises detecting the expression levels of the two or more genes from the second gene classifier by contacting the isolated nucleic acids with a set of probes that recognizes the two or more genes from the second gene classifier, and detecting binding between the two or more genes from the second gene classifier and the set of probes.

12. The method of claim 8, wherein IL-31 is used in a first gene classifier, and one or more of the following genes is used in a second gene classifier: IL-13R, IL-4R, IL-17, IL-22, CXCL9, CXCL10, CXCL11, S100A7, S100A8, S100A9, CCL17, CCL18, CCL19, CCL26, CCL27, or NOS2.

13. The method of claim 1, wherein the sample comprises cells from the stratum corneum.

14. The method of claim 1, wherein an amount of the nucleic acids isolated from the skin sample is from about 100 picograms to about 1 microgram.

15. The method of claim 1, wherein the inhibitor comprises an antibody.

16. The method of claim 1, wherein the inhibitor comprises one or more of lebrikizumab, tralokinumab, crisaborole, and nemolizumab.

* * * * *